(12) United States Patent
Wu et al.

(10) Patent No.: US 11,358,949 B2
(45) Date of Patent: Jun. 14, 2022

(54) CARBAMATE AND UREA COMPOUNDS AS MULTIKINASE INHIBITORS

(71) Applicant: ANGEX PHARMACEUTICAL, INC., North Brunswick, NJ (US)

(72) Inventors: Wen-Lian Wu, Green Brook, NJ (US); Zhiqiang Yang, Westfield, NJ (US); Francis Lee, Yardley, PA (US); John Qiang Tan, North Brunswick, NJ (US)

(73) Assignee: ANGEX PHARMACEUTICAL, INC., North Brunswick, NJ (US)

( * ) Notice: Subject to any disclaimer, the term of this patent is extended or adjusted under 35 U.S.C. 154(b) by 0 days.

(21) Appl. No.: 16/770,697

(22) PCT Filed: Dec. 10, 2018

(86) PCT No.: PCT/US2018/064677
§ 371 (c)(1),
(2) Date: Jun. 8, 2020

(87) PCT Pub. No.: WO2019/125798
PCT Pub. Date: Jun. 27, 2019

(65) Prior Publication Data
US 2021/0163445 A1     Jun. 3, 2021

Related U.S. Application Data

(60) Provisional application No. 62/608,375, filed on Dec. 20, 2017.

(51) Int. Cl.
| | |
|---|---|
| *C07D 239/70* | (2006.01) |
| *C07D 239/72* | (2006.01) |
| *C07D 239/88* | (2006.01) |
| *A61K 31/16* | (2006.01) |
| *A61K 31/50* | (2006.01) |
| *C07D 401/12* | (2006.01) |
| *C07D 215/22* | (2006.01) |
| *C07D 403/12* | (2006.01) |
| *C07D 487/04* | (2006.01) |
| *C07D 487/08* | (2006.01) |

(52) U.S. Cl.
CPC ......... *C07D 401/12* (2013.01); *C07D 215/22* (2013.01); *C07D 403/12* (2013.01); *C07D 487/04* (2013.01); *C07D 487/08* (2013.01)

(58) Field of Classification Search
CPC .. C07D 239/70; C07D 239/72; C07D 239/88; A61K 31/16; A61K 31/50; A61P 35/00
See application file for complete search history.

(56) References Cited

U.S. PATENT DOCUMENTS

| | | |
|---|---|---|
| 2009/0227556 A1 | 9/2009 | Obaishi |
| 2017/0342033 A1 | 11/2017 | Horn |

FOREIGN PATENT DOCUMENTS

| | | |
|---|---|---|
| WO | 2005030140 A2 | 4/2005 |
| WO | 2013032797 A2 | 3/2013 |
| WO | 2017029362 A1 | 2/2017 |

OTHER PUBLICATIONS

Cui, Targeting Receptor Tyrosine Kinase MET in Cancer: Small Molecule Inhibitors and Clinical Progress, J. Med. Chem. 57(11), 4427-4453, Jun. 2014.
Zeng et al., Discovery and Evaluation of Clinical Candidate AZD3759, a Potent, Oral Active, Central Nervous System—Penetrant, Epidermal Growth Factor Receptor Tyrosine Kinase Inhibitor, J. Med. Chem. 58(20), 8200-8215, Oct. 2015.

*Primary Examiner* — Bruck Kifle
(74) *Attorney, Agent, or Firm* — Maschoff Brennan; Brent A. Johnson; Yuefen Zhou

(57) ABSTRACT

The present disclosure describes carbamate and urea compounds as novel multikinase inhibitors and methods for preparing them. The pharmaceutical compositions comprising such multikinase inhibitors and methods of using them for treating cancer, infectious diseases, and other disorders associated with kinases are also described.

20 Claims, No Drawings

CARBAMATE AND UREA COMPOUNDS AS MULTIKINASE INHIBITORS

CROSS-REFERENCE TO RELATED APPLICATIONS

This application is a national phase of the International Patent Application No. PCT/US2018/064677, filed Dec. 10, 2018; which claims the benefit of U.S. Provisional Application No. 62/608,375, filed Dec. 20, 2017; all of which are incorporated by reference by their entirety.

FIELD

The present disclosure relates to heterocyclic compounds comprising carbamate or urea, such as 4-(4-(1-((4-fluorophenyl)carbamoyl)cyclopropane-1-carboxamido)phenoxy)-6-methoxyquinolin-7-yl (R)-2,4-dimethylpiperazine-1-carboxylate (1-11) as multikinase inhibitors, and pharmaceutical compositions containing such compounds. The present disclosure also relates to the use of these compounds and pharmaceutical compositions containing these compounds to treat cancer, infectious diseases and other disorders.

BACKGROUND

Cancer arises when normal cells lose their ability to control cell division and the cells begin to proliferate in an uncontrolled fashion. These alterations of cellular behavior (phenotype) originate in the genetic materials of the affected cancer cells. The genes that cause cancer are termed oncogenes: genes that are overexpressed or mutated so that they can no longer be regulated. Oncogenes exert their effects through proteins that they encode. Many of the oncogenic proteins are protein kinases. The abnormal oncogenic activation of kinases derives from multiple types of genetic and epigenetic changes. These alterations result in increased specific activity of the kinase itself, its overexpression, or the loss of negative regulation. Most frequently, tumor cells harbor somatic point mutations at structurally conserved residues, or mutation hotspots, which constitutively upregulate kinase activity. Examples of these hotspots include M918T in RET and M1268T in MET, which occur at a structurally equivalent position within the kinase domain. Another prevalent mutation hotspot conserved across several oncogenic kinases including KIT D816 and FLT3 D835. Recent efforts from large-scale consortia such as The Cancer Genome Atlas (TCGA) and the International Cancer Genome Consortium (ICGC) have uncovered many new mutations in kinases and enabled a robust delineation of the spectrum of activating kinase mutations in cancer through careful statistical analysis (Lawrence M S et. al. Nature. 2013; 499: 214-218). In addition, genomic instability, a hallmark of cancer cells, can also result in elevated kinase activity that enhances signaling through a number of distinct mechanisms. Defects in the surveillance pathways that maintain genomic integrity can produce amplifications of large chromosomal regions or complex chromosomal rearrangements, which in turn result in the mis-expression of a kinase or the expression of a constitutively activated chimeric form (kinase fusions). Some well-known activation mechanism of kinases in cancer include:

I. Point mutations, including DDR2, DDR1, FLT3, BRK, C-MER, C-MET, c-KIT, FMS, AXL, EPHA2, RET, EPHB4, MNK2, KDR, EPHA3, EPHB2, FLT1, LCK, EPHA4, EPHB1, FLT4, PDGFA, PDGFB, TIE2/TEK, KHS/MAP4K5, BLK, PLK4/SAK, RON/MST1R, EPHA1, FRK/PTK5, MEK1, CDK7/cyclin H, MEK5, and SLK/STK2.

II. Gene amplification, including DDR2, HPK4, DDR1, FLT3, BRK, C-MER, C-MET, c-KIT, FMS, AXL, EPHA2, RET, EPHB4, MNK2, KDR, EPHA3, LOK, EPHB2, FLT1, LCK, EPHA4, EPHB1, FLT4, PDGF, TIE2/TEK, KHS/MAP4K5, BLK, PLK4/SAK, RON/MST1R, EPHA1, FRK/PTK5, MEK1, CDK7/cyclin H, MEK5, and SLK/STK2.

III. Gene amplification or fusion of a kinase ligand, including HGF (MET), VEGFA (VEGFR).

IV. Gene fusions, including ALK, FGR, MET, NTRK, PDGFA, PDGFB, RET, and ROS1.

In addition to cancer, kinase activity has been demonstrated to be responsible for other diseases and disorders. Accordingly, the identification and development of small-molecules that inhibit activity of multiple kinases such as these listed above can potentially provide new therapeutic approaches for successful treatment of related diseases or disorders, such as cancers.

SUMMARY

The present disclosure relates to heterocyclic compounds comprising carbamate or urea groups, such as certain optionally substituted 4-(4-(1-(phenylcarbamoyl)cyclopropane-1-carboxamido)phenoxy)quinolin-7-yl piperazine-1-carboxylate, optionally substituted 4-(4-(1-(phenylcarbamoyl)cyclopropane-1-carboxamido)phenoxy)quinolin-7-yl piperidine-1-carboxylate, optionally substituted 4-(4-(1-(phenylcarbamoyl)cyclopropane-1-carboxamido)phenoxy)quinolin-7-yl pyrrolidine-1-carboxylate, optionally substituted 4-(4-(1-(phenylcarbamoyl)cyclopropane-1-carboxamido)phenoxy)quinolin-7-yl carbamate, optionally substituted 4-(4-(1-(phenylcarbamoyl)cyclopropane-1-carboxamido)phenoxy)quinolin-7-yl 2,6-dihydropyrrolo[3,4-c]pyrazole-5(4H)-carboxylate, optionally substituted 4-(4-(1-(phenylcarbamoyl)cyclopropane-1-carboxamido)phenoxy)quinolin-7-yl morpholine-4-carboxylate, optionally substituted 4-(4-(1-(phenylcarbamoyl)cyclopropane-1-carboxamido)phenoxy)quinolin-7-yl (1R,4R)-2,5-diazabicyclo[2.2.1]heptane-2-carboxylate, optionally substituted 4-(4-(1-(phenylcarbamoyl)cyclopropane-1-carboxamido)phenoxy)quinolin-7-yl (1S,4S)-2,5-diazabicyclo[2.2.1]heptane-2-carboxylate, optionally substituted 4-(4-(1-(phenylcarbamoyl)cyclopropane-1-carboxamido)phenoxy)quinolin-7-yl (1R,5S)-3,8-diazabicyclo[3.2.1]octane-8-carboxylate, optionally substituted 4-(4-(1-(phenylcarbamoyl)cyclopropane-1-carboxamido)phenoxy)quinolin-6-yl piperazine-1-carboxylate, optionally substituted 4-(4-(1-(phenylcarbamoyl)cyclopropane-1-carboxamido)phenoxy)quinazolin-7-yl piperazine-1-carboxylate, or any one of the compounds represented by Formula 1, or any one of other novel compounds described herein, or a pharmaceutically acceptable salt thereof, (referred to collectively herein as a "subject compound") in the manufacture of a medicament for the treatment of cancer, infectious diseases, and other disorders associated with kinases.

Some embodiments include a compound represented by Formula 1:

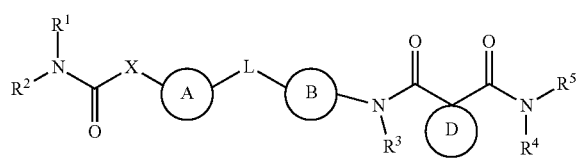

or a pharmaceutically acceptable salt thereof; wherein Ring A is an optionally substituted 10-membered heteroarylene having at least one ring nitrogen atom; Ring B is an optionally substituted 6-membered arylene or an optionally substituted 6-membered heteroarylene containing at least one ring nitrogen atom; Ring D is an optionally substituted 3, 4, 5, or 6-membered carbocycle or an optionally substituted 3, 4, 5, or 6-membered heterocycle; L is —O—, —N($R^A$)—, or —S(O)$_{0-2}$—; X is —O—, or —N($R^B$)—; $R^A$, $R^B$ and $R^3$ are independently H or $C_{1-6}$ hydrocarbyl; $R^1$ and $R^2$ are independently H, optionally substituted $C_{1-12}$ alkyl, optionally substituted $C_{6-10}$ aryl, optionally substituted $C_{3-9}$ heteroaryl, or optionally substituted $C_{1-6}$ cycloalkyl, wherein $R^1$ and $R^2$, together with the N atom to which they are attached, may form an optionally substituted cyclic ring, an optionally substituted bicyclic ring, or an optionally substituted bridged cyclic ring system; and when X is —N($R^B$)—, $R^1$ and $R^B$ may be linked, and together with the N atom to which $R^1$ is attached and the carbonyl group to which X is attached, may form an optionally substituted cyclic ring; and $R^4$ and $R^5$ are independently H, an optionally substituted $C_{1-12}$ hydrocarbyl, an optionally substituted $C_{3-9}$ heteroaryl, or an optionally substituted $C_{3-12}$ heterocycloalkyl, wherein $R^4$ and $R^5$, together with the nitrogen atom to which they are attached, may form an optionally substituted 4, 5, 6, or 7-membered heterocyclyl.

Some embodiments include use of a compound described herein, such as a compound of Formula 1, optionally substituted 4-(4-(1-(phenylcarbamoyl)cyclopropane-1-carboxamido)phenoxy)quinolin-7-yl piperazine-1-carboxylate, optionally substituted 4-(4-(1-(phenylcarbamoyl)cyclopropane-1-carboxamido)phenoxy)quinolin-7-yl piperidine-1-carboxylate, optionally substituted 4-(4-(1-(phenylcarbamoyl)cyclopropane-1-carboxamido)phenoxy)quinolin-7-yl pyrrolidine-1-carboxylate, optionally substituted 4-(4-(1-(phenylcarbamoyl)cyclopropane-1-carboxamido)phenoxy)quinolin-7-ylcarbamate, optionally substituted 4-(4-(1-(phenylcarbamoyl)cyclopropane-1-carboxamido)phenoxy)quinolin-7-yl 2,6-dihydropyrrolo[3,4-c]pyrazole-5(4H)-carboxylate, optionally substituted 4-(4-(1-(phenylcarbamoyl)cyclopropane-1-carboxamido)phenoxy)quinolin-7-yl morpholine-4-carboxylate, optionally substituted 4-(4-(1-(phenylcarbamoyl)cyclopropane-1-carboxamido)phenoxy)quinolin-7-yl(1R,4R)-2,5-diazabicyclo[2.2.1]heptane-2-carboxylate, or optionally substituted 4-(4-(1-(phenylcarbamoyl)cyclopropane-1-carboxamido)phenoxy)quinolin-7-yl(1S,4S)-2,5-diazabicyclo[2.2.1]heptane-2-carboxylate, or a pharmaceutically acceptable salt thereof, (referred to collectively herein as a "subject compound") in the manufacture of a medicament for the treatment of cancer, infectious diseases and other disorders associated with kinases.

Some embodiments include a pharmaceutical composition, a dosage form, and/or a medicament comprising a therapeutically effective amount of a subject compound in combination with at least one pharmaceutically acceptable carrier, referred to herein as a subject pharmaceutical composition. A subject pharmaceutical composition can optionally contain additional excipients.

Some embodiments include a product kit comprising a subject pharmaceutical composition, optionally in the form of a dosage form, and a label describing how to administer the subject pharmaceutical composition to a mammal or a human being for the treatment of cancer, an infectious disease, or another disorder associated with a kinase.

Some embodiments include a process for making a pharmaceutical composition comprising combining a subject compound and at least one pharmaceutically acceptable carrier.

DETAILED DESCRIPTION

Unless otherwise indicated, any reference to a compound herein by structure, name, or any other means, includes pharmaceutically acceptable salts, such as sodium, potassium, and ammonium salts; prodrugs, such as ester prodrugs; alternate solid forms, such as polymorphs, solvates, hydrates, etc.; tautomers; or any other chemical species that may rapidly convert to a compound described herein under conditions in which the compounds are used as described herein.

If stereochemistry is not indicated, a name or structural depiction includes any stereoisomer or any mixture of stereoisomers.

In some embodiments, a compound of Formula 1 is a single enantiomer.

Unless otherwise indicated, when a compound or chemical structural feature such as aryl is referred to as being "optionally substituted," it includes a feature that has no substituents (i.e. unsubstituted), or a feature that is "substituted," meaning that the feature has one or more substituents. The term "substituent" is broad, and includes a moiety that occupies a position normally occupied by one or more hydrogen atoms attached to a parent compound or structural feature. In some embodiments, a substituent may be an ordinary organic moiety known in the art, which may have a molecular weight (e.g. the sum of the atomic masses of the atoms of the substituent) of 15 g/mol to 50 g/mol, 15 g/mol to 100 g/mol, 15 g/mol to 150 g/mol, 15 g/mol to 200 g/mol, 15 g/mol to 300 g/mol, or 15 g/mol to 500 g/mol. In some embodiments, a substituent comprises, or consists of: 0-30, 0-20, 0-10, or 0-5 carbon atoms; and 0-30, 0-20, 0-10, or 0-5 heteroatoms, wherein each heteroatom may independently be: N, O, S, P, Si, F, Cl, Br, or I, and N, S and P can be optionally oxidized; provided that the substituent includes one C, N, O, S, P, Si, F, Cl, Br, or I atom. Examples of substituents include, but are not limited to, deuterium, tritium, alkyl, alkenyl, alkynyl, heteroalkyl, heteroalkenyl, heteroalkynyl, aryl, heteroaryl, hydroxy, alkoxy, aryloxy, acyl, acyloxy, alkylcarboxylate, thiol, alkylthio, cyano, halo, thiocarbonyl, O-carbamyl, N-carbamyl, O-thiocarbamyl, N-thiocarbamyl, C-amido, N-amido, S-sulfonamido, N-sulfonamido, isocyanato, thiocyanato, isothiocyanato, nitro, silyl, sulfenyl, sulfinyl, sulfonyl, haloalkyl, haloalkoxyl, trihalomethanesulfonyl, trihalomethanesulfonamido, amino, phosphonic acid, etc.

For convenience, the term "molecular weight" is used with respect to a moiety or part of a molecule to indicate the sum of the atomic masses of the atoms in the moiety or part of a molecule, even though it may not be a complete molecule.

Unless otherwise indicated, when a ring size is referred to as being "6-membered" as described herein, the ring has a total ring atoms of 6. For example, the term "6-membered carbocycle" has a total of 6 ring carbon atoms, and the term "6-membered heterocycle" contains a total of 6 ring atoms (including ring carbon atoms and ring heteroatoms). Other ring sizes referred to herein should be interpreted in same way.

The structures associated with some of the chemical names referred to herein are depicted below. These structures may be unsubstituted, as shown below, or substituted with a substituent that may independently be in any position normally occupied by a hydrogen atom when the structure is unsubstituted. Unless a point of attachment is indicated by

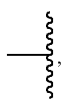

attachment may occur at any position normally occupied by a hydrogen atom.

Structures for Some Examples of Ring A

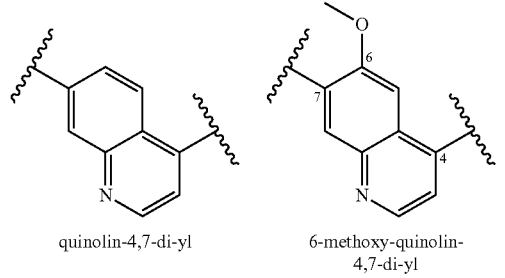

quinolin-4,7-di-yl     6-methoxy-quinolin-4,7-di-yl

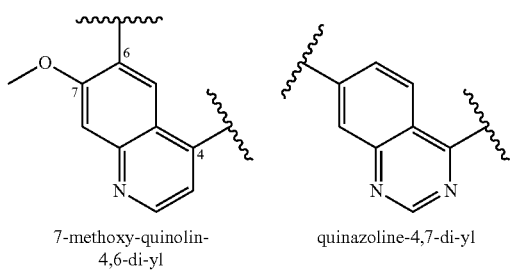

7-methoxy-quinolin-4,6-di-yl     quinazoline-4,7-di-yl

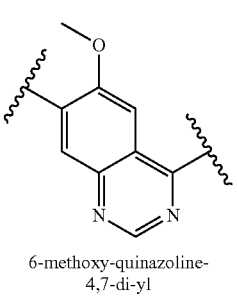

6-methoxy-quinazoline-4,7-di-yl

Structures for Some Examples of Ring B

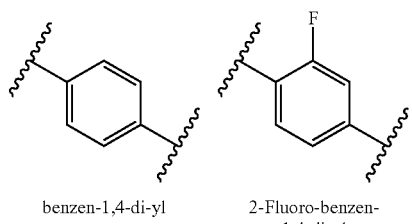

benzen-1,4-di-yl     2-Fluoro-benzen-1,4-di-yl

Structures for Some Examples of Ring D

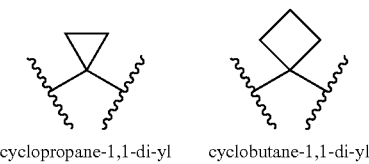 [SMILES: *C1(*)CC1 ; *C1(*)CCC1]

cyclopropane-1,1-di-yl     cyclobutane-1,1-di-yl

Structures for Some Examples of $R^1$ and $R^2$ Together with N to which they are Attached

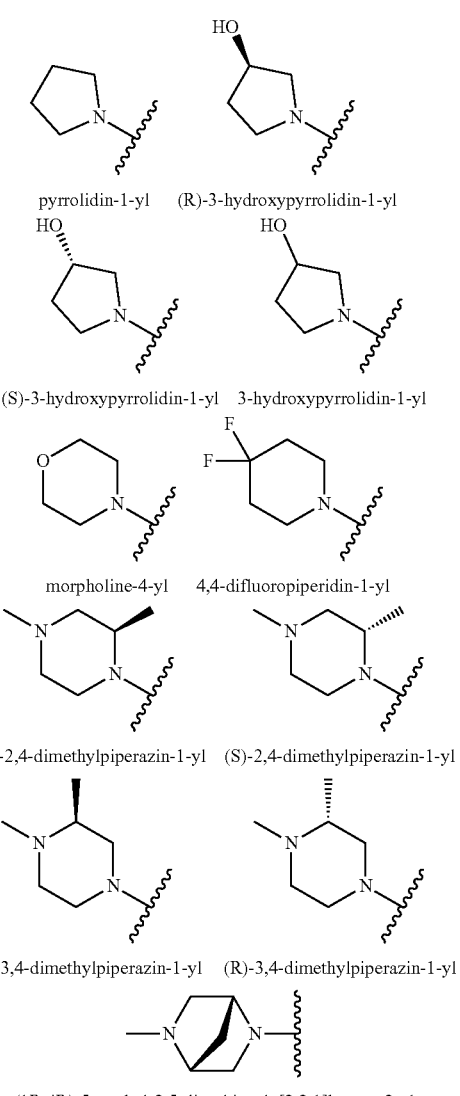

pyrrolidin-1-yl     (R)-3-hydroxypyrrolidin-1-yl (S)-3-hydroxypyrrolidin-1-yl     3-hydroxypyrrolidin-1-yl morpholine-4-yl     4,4-difluoropiperidin-1-yl (R)-2,4-dimethylpiperazin-1-yl     (S)-2,4-dimethylpiperazin-1-yl (S)-3,4-dimethylpiperazin-1-yl     (R)-3,4-dimethylpiperazin-1-yl (1R,4R)-5-methyl-2,5-diazabicyclo[2.2.1]heptan-2-yl (1S,4S)-5-methyl-2,5-diazabicyclo[2.2.1]heptan-2-yl

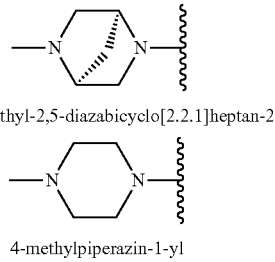

4-methylpiperazin-1-yl

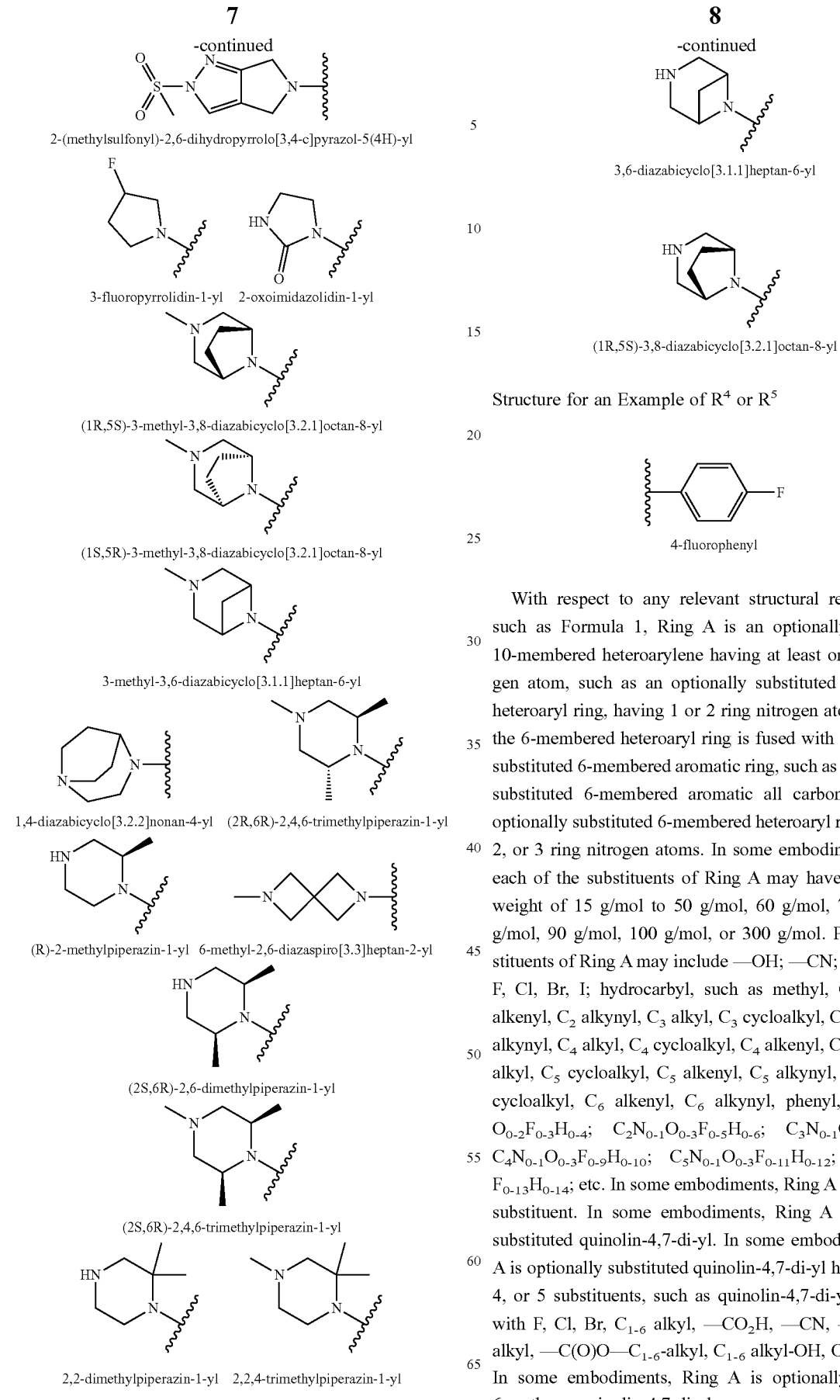

Structure for an Example of $R^4$ or $R^5$ 4-fluorophenyl

With respect to any relevant structural representation, such as Formula 1, Ring A is an optionally substituted 10-membered heteroarylene having at least one ring nitrogen atom, such as an optionally substituted 6-membered heteroaryl ring, having 1 or 2 ring nitrogen atoms, wherein the 6-membered heteroaryl ring is fused with an optionally substituted 6-membered aromatic ring, such as an optionally substituted 6-membered aromatic all carbon ring or an optionally substituted 6-membered heteroaryl ring having 1, 2, or 3 ring nitrogen atoms. In some embodiments, any or each of the substituents of Ring A may have a molecular weight of 15 g/mol to 50 g/mol, 60 g/mol, 70 g/mol, 80 g/mol, 90 g/mol, 100 g/mol, or 300 g/mol. Potential substituents of Ring A may include —OH; —CN; halo, such as F, Cl, Br, I; hydrocarbyl, such as methyl, $C_2$ alkyl, $C_2$ alkenyl, $C_2$ alkynyl, $C_3$ alkyl, $C_3$ cycloalkyl, $C_3$ alkenyl, $C_3$ alkynyl, $C_4$ alkyl, $C_4$ cycloalkyl, $C_4$ alkenyl, $C_4$ alkynyl, $C_5$ alkyl, $C_5$ cycloalkyl, $C_5$ alkenyl, $C_5$ alkynyl, $C_6$ alkyl, $C_6$ cycloalkyl, $C_6$ alkenyl, $C_6$ alkynyl, phenyl, etc.; $CN_{0-1}O_{0-2}F_{0-3}H_{0-4}$; $C_2N_{0-1}O_{0-3}F_{0-5}H_{0-6}$; $C_3N_{0-1}O_{0-3}F_{0-7}H_{0-8}$; $C_4N_{0-1}O_{0-3}F_{0-9}H_{0-10}$; $C_5N_{0-1}O_{0-3}F_{0-11}H_{0-12}$; $C_6N_{0-1}O_{0-3}F_{0-13}H_{0-14}$; etc. In some embodiments, Ring A has an $OCH_3$ substituent. In some embodiments, Ring A is optionally substituted quinolin-4,7-di-yl. In some embodiments, Ring A is optionally substituted quinolin-4,7-di-yl having 1, 2, 3, 4, or 5 substituents, such as quinolin-4,7-di-yl substituted with F, Cl, Br, $C_{1-6}$ alkyl, —$CO_2H$, —CN, —CO—$C_{1-6}$-alkyl, —C(O)O—$C_{1-6}$-alkyl, $C_{1-6}$ alkyl-OH, OH, $NH_2$, etc. In some embodiments, Ring A is optionally substituted 6-methoxy-quinolin-4,7-di-yl.

With respect to Formula 1, in some embodiments, Ring A is represented by Formula A1, A2, or A3:

Formula A1

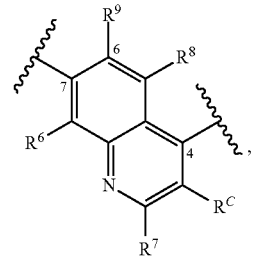

Formula A2

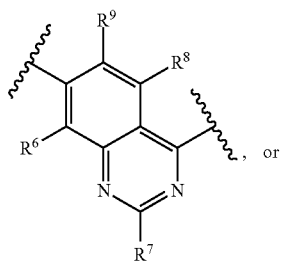

, or

Formula A3

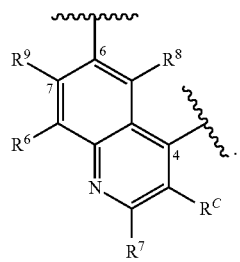

.

With respect to any relevant structural representation, such as Formula A1, A2, or A3, $R^6$ is H or any substituent, such as $R^A$, F, Cl, CN, —$OR^A$, $CF_3$, —$NO_2$, —$NR^AR^B$, —$COR^A$, $O_2R^A$, —$OCOR^A$, —$NR^ACOR^B$, or —$CONR^AR^B$, etc. Some of the structures with attachment points are shown below. In some embodiments, $R^6$ may be H; F; Cl; —CN; $CF_3$; OH; $NH_2$; $C_{1-6}$ alkyl, such as methyl, ethyl, any one of the propyl isomers (e.g. n-propyl and isopropyl), cyclopropyl, any one of the butyl isomers, any one of the cyclobutyl isomers (e.g. cyclobutyl and methylcyclopropyl), any one of the pentyl isomers, any one of the cyclopentyl isomers, any one of the hexyl isomers, and any one of the cyclohexyl isomers, etc.; or $C_{1-6}$ alkoxy, such as —O-methyl, —O-ethyl, any one of the isomers of —O-propyl, —O-cyclopropyl, any one of the isomers of —O-butyl, any one of the isomers of —O-cyclobutyl, any one of the isomers of —O-pentyl, any one of the isomers of —O-cyclopentyl, any one of the isomers of —O-hexyl, any one of the isomers of —O-cyclohexyl, etc. In some embodiments, $R^6$ may be H, F, Cl, or $NH_2$. In some embodiments, $R^6$ may be —$OCH_3$. In some embodiments, $R^6$ may be H.

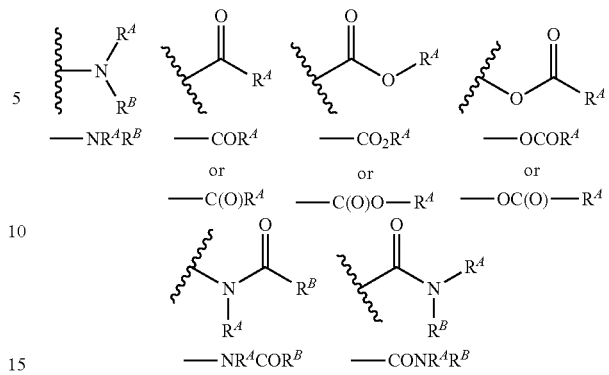

—$NR^AR^B$  —$COR^A$  —$CO_2R^A$  —$OCOR^A$ or  or  or

—$C(O)R^A$  —$C(O)O$—$R^A$  —$OC(O)$—$R^A$

—$NR^ACOR^B$  —$CONR^AR^B$

With respect to any relevant structural representation, each $R^A$ may independently be H, or $C_{1-12}$ hydrocarbyl, such as $C_{1-12}$ alkyl, $C_{1-12}$ alkenyl, $C_{1-12}$ alkynyl, phenyl, etc., including: linear or branched alkyl having a formula $C_aH_{2a+1}$, or cycloalkyl having a formula $C_aH_{2a-1}$, wherein a is 1, 2, 3, 4, 5, 6, 7, 8, 9, 10, 11, or 12, such as linear or branched alkyl with a formula: $CH_3$, $C_2H_5$, $C_3H_7$, $C_4H_9$, $C_5H_{11}$, $C_6H_{13}$, $C_7H_{15}$, $C_8H_{17}$, $C_9H_{19}$, $C_{10}H_{21}$, etc., or cycloalkyl with a formula: $C_3H_5$, $C_4H_7$, $C_5H_9$, $C_6H_{11}$, $C_7H_{13}$, $CH_{15}$, $C_9H_{17}$, $C_{10}H_{19}$, etc. In some embodiments, $R^A$ may be H or $C_{1-6}$ alkyl. In some embodiments, $R^A$ may be H or $C_{1-3}$ alkyl. In some embodiments, $R^A$ may be H or $CH_3$. In some embodiments, $R^A$ may be H.

With respect to any relevant structural representation, each $R^B$ may independently be H, or $C_{1-12}$ hydrocarbyl, such as $C_{1-12}$ alkyl, $C_{1-12}$ alkenyl, $C_{1-12}$ alkynyl, phenyl, etc., including: linear or branched alkyl having a formula $C_aH_{2a+1}$, or cycloalkyl having a formula $C_aH_{2a-1}$, wherein a is 1, 2, 3, 4, 5, 6, 7, 8, 9, 10, 11, or 12, such as linear or branched alkyl with a formula: $CH_3$, $C_2H_5$, $C_3H_7$, $C_4H_9$, $C_5H_{11}$, $C_6H_{13}$, $C_7H_{15}$, $C_8H_{17}$, $C_9H_{19}$, $C_{10}H_{21}$, etc., or cycloalkyl with a formula: $C_3H_5$, $C_4H_7$, $C_5H_9$, $C_6H_{11}$, $C_7H_{13}$, $C_8H_{15}$, $C_9H_{17}$, $C_{10}H_{19}$, etc. In some embodiments, $R^B$ may be H or $C_{1-3}$ alkyl. In some embodiments, $R^B$ may be H or $CH_3$. In some embodiments, $R^B$ may be H.

With respect to any relevant structural representation, such as Formula A1, A2, or A3, $R^7$ is H or any substituent, such as $R^A$, F, Cl, CN, —$OR^A$, $CF_3$, —$NO_2$, —$NR^AR^B$, —$COR^A$, $O_2R^A$, —$OCOR^A$, —$NR^ACOR^B$, or —$CONR^AR^B$, etc. In some embodiments, $R^7$ may be H, F, Cl, CN, $CF_3$, OH, $NH_2$, $C_{1-6}$ alkyl, or $C_{1-6}$ alkoxy. In some embodiments, $R^7$ may be H, F, Cl, or $NH_2$. In some embodiments, $R^7$ may be —$OCH_3$. In some embodiments, $R^7$ may be H.

With respect to any relevant structural representation, such as Formula A1, A2, or A3, $R^8$ is H or any substituent, such as $R^A$, F, Cl, CN, —$OR^A$, $CF_3$, —$NO_2$, —$NR^AR^B$, —$COR^A$, $CO_2R^A$, —$OCOR^A$, —$NR^ACOR^B$, or —$CONR^AR^B$, etc. In some embodiments, $R^8$ may be H, F, Cl, CN, $CF_3$, OH, $NH_2$, $C_{1-6}$ alkyl, or $C_{1-6}$ alkoxy. In some embodiments, $R^8$ may be H, F, Cl, or $NH_2$. In some embodiments, $R^8$ may be —$OCH_3$. In some embodiments, $R^8$ may be H.

With respect to any relevant structural representation, such as Formula A1, A2, or A3, $R^9$ is H or any substituent, such as $R^A$, F, Cl, CN, —$OR^A$, $CF_3$, —$NO_2$, —$NR^AR^B$, —$COR^A$, $O_2R^A$, —$OCOR^A$, —$NR^ACOR^B$, or —$CONR^AR^B$, etc. In some embodiments, $R^9$ may be H, F, Cl, CN, $CF_3$, OH, $NH_2$, $C_{1-6}$ alkyl, or $C_{1-6}$ alkoxy. In some embodiments, $R^9$ may be H, F, Cl, or $NH_2$. In some embodiments, $R^9$ may be H. In some embodiments, $R^9$ may be —$OCH_3$.

With respect to any relevant structural representation, such as Formula A1 or A3, $R^C$ is H or any substituent, such as $R^A$, F, Cl, CN, —OH, —$OR^A$, $CF_3$, —$NO_2$, —$NR^AR^B$, —$COR^A$, $O_2R^A$, —$OCOR^A$, —$NR^ACOR^B$, —$CONR^AR^B$, or $SO_2N(R^A)(R^B)$. In some embodiments, $R^C$ is H. In some embodiments, $R^C$ is CN.

With respect to any relevant structural representation, such as Formula A1 or A3, in some embodiments, $R^C$, $R^6$, $R^7$, and $R^8$ are all H. In some embodiments, $R^C$, $R^6$, $R^7$, and $R^8$ are all H, and $R^9$ is —$OCH_3$.

With respect to any relevant structural representation, such as Formula 1, Ring B is an optionally substituted 6-membered arylene or an optionally substituted 6-membered heteroarylene containing at least one ring nitrogen atom. In some embodiments, any or each of the substituents of Ring B may have a molecular weight of 15 g/mol to 50 g/mol, 100 g/mol, or 300 g/mol. Potential substituents of Ring B may include halo, such as F, Cl, Br, or I; hydrocarbyl, such as methyl, $C_2$ alkyl, $C_2$ alkenyl, $C_2$ alkynyl, $C_3$ alkyl, $C_3$ cycloalkyl, $C_3$ alkenyl, $C_3$ alkynyl, $C_4$ alkyl, $C_4$ cycloalkyl, $C_4$ alkenyl, $C_4$ alkynyl, $C_5$ alkyl, $C_5$ cycloalkyl, $C_5$ alkenyl, $C_5$ alkynyl, $C_6$ alkyl, $C_6$ cycloalkyl, $C_6$ alkenyl, $C_6$ alkynyl, or phenyl, etc.; $CN_{0-1}O_{0-2}F_{0-3}H_{0-4}$; $C_2N_{0-1}O_{0-3}F_{0-5}H_{0-6}$; $C_3N_{0-1}O_{0-3}F_{0-7}H_{0-8}$; $C_4N_{0-1}O_{0-3}F_{0-9}H_{0-10}$; $C_5N_{0-1}O_{0-3}F_{0-11}H_{0-12}$; $C_6N_{0-1}O_{0-3}F_{0-13}H_{0-14}$; etc. In some embodiments, Ring B is optionally substituted phenylene having 0, 1, 2, 3, or 4 substituents, such as phenylene substituted with F, Cl, Br, $C_{1-6}$ alkyl, —$CO_2H$, —CN, —CO—$C_{1-6}$-alkyl, —C(O)O—$C_{1-6}$-alkyl, —$C_{1-6}$ alkyl-OH, OH, $NH_2$, etc. In some embodiments, Ring B is phenylene having 2 substituents. In some embodiments, Ring B is phenylene having 1 substituent. In some embodiments, Ring B is phenylene having an F substituent. In some embodiments, Ring B is unsubstituted phenylene.

In some embodiments, Ring B is represented by formula B1 or B2:

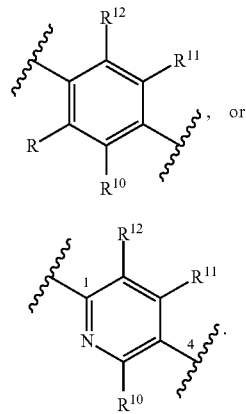

Formula B1

Formula B2

With respect to any relevant structural representation, such as Formula B1 or B2, $R^{10}$ is H or any substituent, such as $R^A$, F, Cl, CN, —$OR^A$, $CF_3$, —$NO_2$, —$NR^AR^B$, —$COR^A$, $CO_2R^A$, —$OCOR^A$, —$NR^ACOR^B$, or —$CONR^AR^B$, etc. In some embodiments, $R^{10}$ may be H, F, Cl, CN, $CF_3$, OH, $NH_2$, $C_{1-6}$ alkyl, or $C_{1-6}$ alkoxy. In some embodiments, $R^{10}$ may be H, F, or Cl. In some embodiments, $R^{10}$ may be H. In some embodiments, $R^{10}$ may be F.

With respect to any relevant structural representation, such as Formula B1 or B2, $R^{11}$ is H or any substituent, such as $R^A$, F, Cl, CN, —$OR^A$, $CF_3$, —$NO_2$, —$NR^AR^B$, —$COR^A$, $CO_2R^A$, —$OCOR^A$, —$NR^ACOR^B$, or —$CONR^AR^B$, etc. In some embodiments, $R^{11}$ may be H, F, Cl, CN, $CF_3$, OH, $NH_2$, $C_{1-6}$ alkyl, or $C_{1-6}$ alkoxy. In some embodiments, $R^{11}$ may be H, F, or Cl. In some embodiments, $R^{11}$ may be H. In some embodiments, $R^{11}$ may be F.

With respect to any relevant structural representation, such as Formula B1 or B2, $R^{12}$ is H or any substituent, such as $R^A$, F, Cl, CN, —$OR^A$, $CF_3$, —$NO_2$, —$NR^AR^B$, —$COR^A$, $CO_2R^A$, —$OCOR^A$, —$NR^ACOR^B$, or —$CONR^AR^B$, etc. In some embodiments, $R^{12}$ may be H, F, Cl, CN, $CF_3$, OH, $NH_2$, $C_{1-6}$ alkyl, or $C_{1-6}$ alkoxy. In some embodiments, $R^{12}$ may be H, F, or Cl. In some embodiments, $R^{12}$ may be H. In some embodiments, $R^{12}$ may be F.

With respect to any relevant structural representation, such as Formula B1, R is H or any substituent, such as $R^A$, F, Cl, CN, —OH, —$OR^A$, $CF_3$, —$NO_2$, —$NR^AR^B$, —$COR^A$, $CO_2R^A$, —$OCOR^A$, —$NR^ACOR^B$, —$CONR^AR^B$, or $SO_2N(R^A)(R^B)$. In some embodiments, R is optionally substituted $C_{1-3}$ alkyl. In some embodiments, R is H. In some embodiments, R is F. In some embodiments, R, $R^{10}$, $R^{11}$, and $R^{12}$ are all H. In some embodiments, $R^{10}$, $R^{11}$, and $R^{12}$ are all H, and R is F.

In some embodiments, Ring A of Formula 1 comprises:

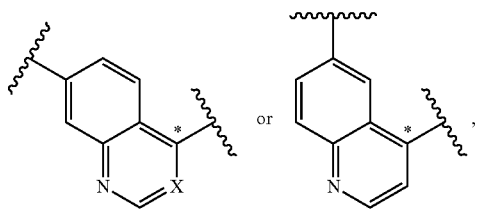

Ring B comprises:

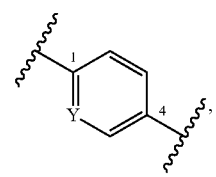

wherein each structure is optionally substituted; X is N or C(R); the asterisk indicates the point of attachment of C atom of Ring A to L; Y is N or C(R); the ring carbon atom at position 1 of Ring B is directly attached to L; wherein each R is independently H, F, Cl, Br, I, —CN, —OH, optionally substituted $C_{1-6}$ hydrocarbyl, optionally substituted O—$C_{1-6}$ hydrocarbyl, —CO—$C_{1-6}$-hydrocarbyl, —C(O)OH, —C(O)O—$C_{1-6}$ hydrocarbyl, —$CON(R^A)(R^B)$, —$N(R^A)(R^B)$, or $SO_2N(R^A)(R^B)$.

With respect to any relevant structural representation, such as Formula 1, Ring D is an optionally substituted 3, 4, 5, or 6-membered carbocycle or an optionally substituted 3, 4, 5, or 6-membered heterocycle. In some embodiments, any or each of the substituents of Ring D may have a molecular weight of 15 g/mol to 50 g/mol, 100 g/mol, or 300 g/mol. Potential substituents of Ring D may include halo, such as F, Cl, Br, or I; hydrocarbyl, such as methyl, $C_2$ alkyl, $C_2$ alkenyl, $C_2$ alkynyl, $C_3$ alkyl, $C_3$ cycloalkyl, $C_3$ alkenyl, $C_3$ alkynyl, $C_4$ alkyl, $C_4$ cycloalkyl, $C_4$ alkenyl, $C_4$ alkynyl, $C_5$ alkyl, $C_5$ cycloalkyl, $C_5$ alkenyl, $C_5$ alkynyl, $C_6$ alkyl, $C_6$ cycloalkyl, $C_6$ alkenyl, $C_6$ alkynyl, or phenyl, etc.; $CN_{0-1}O_{0-2}F_{0-3}H_{0-4}$; $C_2N_{0-1}O_{0-3}F_{0-5}H_{0-6}$; $C_3N_{0-1}O_{0-3}F_{0-7}H_{0-8}$;

$C_4N_{0-1}O_{0-3}F_{0-9}H_{0-10}$; $C_5N_{0-1}O_{0-3}F_{0-11}H_{0-12}$; $C_6N_{0-1}O_{0-3}F_{0-13}H_{0-14}$; etc. In some embodiments, Ring D is optionally substituted cyclopropane-1,1-di-yl having 0, 1, 2, 3, or 4 substituents, such as cyclopropane-1,1-di-yl substituted with F, Cl, Br, $C_{1-6}$ alkyl, —$CO_2H$, —CN, —CO—$C_{1-6}$-alkyl, —C(O)O—$C_{1-6}$-alkyl, —$C_{1-6}$ alkyl-OH, OH, $NH_2$, etc. In some embodiments, Ring D is cyclopropane-1,1-di-yl having 2 substituents. In some embodiments, Ring D is cyclopropane-1,1-di-yl having 2 substituents. In some embodiments, Ring D is cyclopropane-1,1-di-yl having 1 substituent. In some embodiments, Ring D is cyclopropane-1,1-di-yl having 2 $CH_3$ substituents. In some embodiments, Ring D is cyclopropane-1,1-di-yl having a $CH_3$ substituent. In some embodiments, Ring D is unsubstituted cyclopropane-1,1-di-yl.

In some embodiments, Ring D is represented by formula D1, D2 or D3:

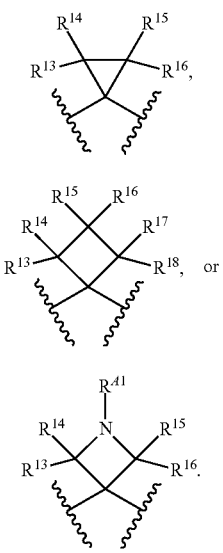

Formula D1

Formula D2

Formula D3

With respect to any relevant structural representation, such as Formula D1, D2, or D3, $R^{13}$ is H or any substituent, such as $R^A$, F, Cl, CN, —$OR^A$, $CF_3$, —$NR^AR^B$, —$COR^A$, $CO_2R^A$, —$OCOR^A$, —$NR^ACOR^B$, or —$CONR^AR^B$, etc. In some embodiments, $R^{13}$ may be H, F, Cl, CN, $CF_3$, OH, $NH_2$, $C_{1-6}$ alkyl, or $C_{1-6}$ alkoxy. In some embodiments, $R^{13}$ may be H, F, Cl, OH, or $CH_3$. In some embodiments, $R^{13}$ may be $CH_3$. In some embodiments, $R^{13}$ may be H.

With respect to any relevant structural representation, such as Formula D1, D2, or D3, $R^{14}$ is H or any substituent, such as $R^A$, F, Cl, CN, —$OR^A$, $CF_3$, —$NR^AR^B$, —$COR^A$, $CO_2R^A$, —$OCOR^A$, —$NR^ACOR^B$, or —$CONR^AR^B$, etc. In some embodiments, $R^{14}$ may be H, F, Cl, CN, $CF_3$, OH, $NH_2$, $C_{1-6}$ alkyl, or $C_{1-6}$ alkoxy. In some embodiments, $R^{14}$ may be H, F, Cl, OH, or $CH_3$. In some embodiments, $R^{14}$ may be $CH_3$. In some embodiments, $R^{14}$ may be H.

With respect to any relevant structural representation, such as Formula D1, D2, or D3, $R^{15}$ is H or any substituent, such as $R^A$, F, Cl, CN, —$OR^A$, $CF_3$, —$NR^AR^B$, —$COR^A$, $CO_2R^A$, —$OCOR^A$, —$NR^ACOR^B$, or —$CONR^AR^B$, etc. In some embodiments, $R^{15}$ may be H, F, Cl, CN, $CF_3$, OH, $NH_2$, $C_{1-6}$ alkyl, or $C_{1-6}$ alkoxy. In some embodiments, $R^{15}$ may be H, F, Cl, OH, or $CH_3$. In some embodiments, $R^{15}$ may be $CH_3$. In some embodiments, $R^{15}$ may be H.

With respect to any relevant structural representation, such as Formula D1, D2, or D3, $R^{16}$ is H or any substituent, such as $R^A$, F, Cl, CN, —$OR^A$, $CF_3$, —$NR^AR^B$, —$COR^A$, $CO_2R^A$, —$OCOR^A$, —$NR^ACOR^B$, or —$CONR^AR^B$, etc. In some embodiments, $R^{16}$ may be H, F, Cl, CN, $CF_3$, OH, $NH_2$, $C_{1-6}$ alkyl, or $C_{1-6}$ alkoxy. In some embodiments, $R^{16}$ may be H, F, Cl, OH, or $CH_3$. In some embodiments, $R^{16}$ may be $CH_3$. In some embodiments, $R^{16}$ may be H.

With respect to any relevant structural representation, such as Formula D2, $R^{17}$ is H or any substituent, such as $R^A$, F, Cl, CN, —$OR^A$, $CF_3$, —$NR^AR^B$, —$COR^A$, $CO_2R^A$, —$OCOR^A$, —$NR^ACOR^B$, or —$CONR^AR^B$, etc. In some embodiments, $R^{17}$ may be H, F, Cl, CN, $CF_3$, OH, $NH_2$, $C_{1-6}$ alkyl, or $C_{1-6}$ alkoxy. In some embodiments, $R^{17}$ may be H, F, Cl, OH, or $CH_3$. In some embodiments, $R^{17}$ may be $CH_3$. In some embodiments, $R^{17}$ may be H.

With respect to any relevant structural representation, such as Formula D2, $R^{18}$ is H or any substituent, such as $R^A$, F, Cl, CN, —$OR^A$, $CF_3$, —$NR^AR^B$, —$COR^A$, $CO_2R^A$, —$OCOR^A$, —$NR^ACOR^B$, or —$CONR^AR^B$, etc. In some embodiments, $R^{18}$ may be H, F, Cl, CN, $CF_3$, OH, $NH_2$, $C_{1-6}$ alkyl, or $C_{1-6}$ alkoxy. In some embodiments, $R^{18}$ may be H, F, Cl, OH, or $CH_3$. In some embodiments, $R^{18}$ may be $CH_3$. In some embodiments, $R^{18}$ may be H.

With respect to any relevant structural representation, such as Formula D2, $R^{41}$ may independently be H, or $C_{1-12}$ hydrocarbyl as described above for $R^A$. In some embodiments, $R^{41}$ may be H or $C_{1-6}$ alkyl. In some embodiments, $R^{41}$ may be H or $C_{1-3}$ alkyl. In some embodiments, $R^{41}$ may be H or $CH_3$. In some embodiments, $R^{41}$ may be H. In some embodiments, $R^{41}$ may be benzyl.

With respect to any relevant structural representation, such as Formula 1, L is —O—, —$N(R^A)$—, or —$S(O)_{0-2}$—. In some embodiments, L is —O—. In some embodiments, L is —$N(R^A)$—. In some embodiments, L is —$S(O)_{0-2}$—. In some embodiments, L is —$N(R^A)$—, wherein $R^A$ is H. In some embodiments, L is —$N(R^A)$—, wherein $R^A$ is $CH_3$.

With respect to any relevant structural representation, such as Formula 1, X is —O—, or —$N(R^B)$—. In some embodiments, X is —O—. In some embodiments, X is —$N(R^B)$—. In some embodiments, X and L are both —O—.

With respect to any relevant structural representation, such as Formula 1, $R^3$ is H or $C_{1-6}$ hydrocarbyl. In some embodiments, $R^3$ is H.

With respect to any relevant structural representation, such as Formula 1, in some embodiments, $R^1$ is H; an optionally substituted hydrocarbyl, including $C_{1-12}$, $C_{1-6}$, or $C_{1-3}$ hydrocarbyl (such as $C_{1-12}$, $C_{1-6}$, or $C_{1-3}$ alkyl; $C_{6-10}$ aryl, or $C_{3-6}$ cycloalkyl); or an optionally substituted heteroaryl, such as substituted $C_{3-9}$ heteroaryl or unsubstituted $C_{3-9}$ heteroaryl. In some embodiments, $R^1$ is $CH_3$.

With respect to any relevant structural representation, such as Formula 1, in some embodiments, $R^2$ is H; an optionally substituted hydrocarbyl, including $C_{1-12}$, $C_{1-6}$, or $C_{1-3}$ hydrocarbyl (such as $C_{1-12}$, $C_{1-6}$, or $C_{1-3}$ alkyl; $C_{6-10}$ aryl, or $C_{3-6}$ cycloalkyl); or an optionally substituted heteroaryl, such as substituted $C_{3-9}$ heteroaryl or unsubstituted $C_{3-9}$ heteroaryl. In some embodiments, $R^2$ is $CH_3$.

With respect to any relevant structural representation, such as Formula 1, in some embodiments, $R^1$ and $R^2$ together with the N atom to which they attached may form an optionally substituted cyclic ring, an optionally substituted bicyclic ring, or an optionally substituted bridged cyclic ring system; and when X is —$N(R^B)$—, $R^1$ and $R^B$ may be linked, and together with the N atom to which $R^1$ is attached and the carbonyl group to which X is attached, may form an optionally substituted cyclic ring. In some embodiments, $R^1$ and $R^2$ are both H. In some embodiments, $R^1$ and $R^2$ are both CHs.

With respect to any relevant structural representation, such as Formula 1, in some embodiments, —$N(R^1)(R^2)$ is optionally substituted pyrrolidin-1-yl. In some embodiments, —$N(R^1)(R^2)$ is optionally substituted (R)-3-hydroxypyrrolidin-1-yl. In some embodiments, —$N(R^1)(R^2)$ is optionally substituted (S)-3-hydroxypyrrolidin-1-yl. In some embodiments, —N(R¹)(R²) is optionally substituted 3-hydroxypyrrolidin-1-yl. In some embodiments, —N(R¹)(R²) is optionally substituted morpholine-4-yl. In some embodiments, —N(R¹)(R²) is optionally substituted piperidin-1-yl. In some embodiments, —N(R¹)(R²) is optionally substituted 4,4-difluoropiperidin-1-yl. In some embodiments, —N(R¹)(R²) is optionally substituted piperazin-1-yl. In some embodiments, —N(R¹)(R²) is optionally substituted (R)-2,4-dimethylpiperazin-1-yl. In some embodiments, —N(R¹)(R²) is optionally substituted (S)-2,4-dimethylpiperazin-1-yl. In some embodiments, —N(R¹)(R²) is optionally substituted (S)-3,4-dimethylpiperazin-1-yl. In some embodiments, —N(R¹)(R²) is optionally substituted (R)-3,4-dimethylpiperazin-1-yl. In some embodiments, —N(R¹)(R²) is optionally substituted 2,5-diazabicyclo[2.2.1]heptan-2-yl. In some embodiments, —N(R¹)(R²) is optionally substituted (1R,4R)-5-methyl-2,5-diazabicyclo[2.2.1]heptan-2-yl. In some embodiments, —N(R¹)(R²) is optionally substituted (1S,4S)-5-methyl-2,5-diazabicyclo[2.2.1]heptan-2-yl. In some embodiments, —N(R¹)(R²) is optionally substituted 4-methylpiperazin-1-yl. In some embodiments, —N(R¹)(R²) is optionally substituted 2,6-dihydropyrrolo[3,4-c]pyrazol-5(4H)-yl. In some embodiments, —N(R¹)(R²) is optionally substituted 2-(methylsulfonyl)-2,6-dihydropyrrolo[3,4-c]pyrazol-5(4H)-yl. In some embodiments, —N(R¹)(R²) is optionally substituted 3-fluoropyrrolidin-1-yl. In some embodiments, —N(R¹)(R²) is optionally substituted (1R,5S)-3-methyl-3,8-diazabicyclo[3.2.1]octan-8-yl. In some embodiments, —N(R¹)(R²) is optionally substituted (1S,5R)-3-methyl-3,8-diazabicyclo[3.2.1]octan-8-yl. In some embodiments, —N(R¹)(R²) is optionally substituted 3-methyl-3,8-diazabicyclo[3.2.1]octan-8-yl. In some embodiments, —N(R¹)(R²) is optionally substituted 3-methyl-3,6-diazabicyclo[3.1.1]heptan-6-yl. In some embodiments, —N(R¹)(R²) is optionally substituted 1,4-diazabicyclo[3.2.2]nonan-4-yl. In some embodiments, —N(R¹)(R²) is optionally substituted (2R,6R)-2,4,6-trimethylpiperazin-1-yl. In some embodiments, —N(R¹)(R²) is optionally substituted (R)-2-methylpiperazin-1-yl. In some embodiments, —N(R¹)(R²) is optionally substituted 6-methyl-2,6-diazaspiro[3.3]heptan-2-yl. In some embodiments, —N(R¹)(R²) is optionally substituted (2S,6R)-2,6-dimethylpiperazin-1-yl. In some embodiments, —N(R¹)(R²) is optionally substituted (2S,6R)-2,4,6-trimethylpiperazin-1-yl. In some embodiments, —N(R¹)(R²) is optionally substituted 2,2-dimethylpiperazin-1-yl. In some embodiments, —N(R¹)(R²) is optionally substituted 2,2,4-trimethylpiperazin-1-yl. In some embodiments, —N(R¹)(R²) is optionally substituted 3,6-diazabicyclo[3.1.1]heptan-6-yl. In some embodiments, —N(R¹)(R²) is optionally substituted (1R,5S)-3,8-diazabicyclo[3.2.1]octan-8-yl.

With respect of any relevant structural representation, such as Formula 1, in some embodiments, R⁴ is H, an optionally substituted $C_{1-12}$ hydrocarbyl, an optionally substituted heteroaryl, such as an optionally substituted $C_{3-9}$ heteroaryl, or an optionally substituted $C_{3-12}$ heterocycloalkyl. In some embodiments, R⁴ is H.

With respect of any relevant structural representation, such as Formula 1, in some embodiments, R⁵ is H, an optionally substituted $C_{1-12}$ hydrocarbyl, an optionally substituted heteroaryl, such as an optionally substituted $C_{3-9}$ heteroaryl, or an optionally substituted $C_{3-12}$ heterocycloalkyl. In some embodiments, R⁵ is optionally substituted phenyl. In some embodiments, R⁵ is 4-fluorophenyl.

With respect of any relevant structural representation, such as Formula 1, in some embodiments, R⁴ and R⁵ together with the nitrogen atom to which they are attached, may form an optionally substituted 4, 5, 6, or 7-membered heterocyclyl.

Some embodiments include optionally substituted 4-(4-(1-(phenylcarbamoyl)cyclopropane-1-carboxamido)phenoxy)quinolin-7-yl piperazine-1-carboxylate, optionally substituted 4-(4-(1-(phenylcarbamoyl)cyclopropane-1-carboxamido)phenoxy)quinolin-7-yl piperidine-1-carboxylate, optionally substituted 4-(4-(1-(phenylcarbamoyl)cyclopropane-1-carboxamido)phenoxy)quinolin-7-yl pyrrolidine-1-carboxylate, optionally substituted 4-(4-(1-(phenylcarbamoyl)cyclopropane-1-carboxamido)phenoxy)quinolin-7-yl carbamate, optionally substituted 4-(4-(1-(phenylcarbamoyl)cyclopropane-1-carboxamido)phenoxy)quinolin-7-yl 2,6-dihydropyrrolo[3,4-c]pyrazole-5(4H)-carboxylate, optionally substituted 4-(4-(1-(phenylcarbamoyl)cyclopropane-1-carboxamido)phenoxy)quinolin-7-yl morpholine-4-carboxylate, optionally substituted 4-(4-(1-(phenylcarbamoyl)cyclopropane-1-carboxamido)phenoxy)quinolin-7-yl (1R,4R)-2,5-diazabicyclo[2.2.1]heptane-2-carboxylate, optionally substituted 4-(4-(1-(phenylcarbamoyl)cyclopropane-1-carboxamido)phenoxy)quinolin-7-yl (1S,4S)-2,5-diazabicyclo[2.2.1]heptane-2-carboxylate, optionally substituted N-(4-((7-(2-oxoimidazolidin-1-yl)quinolin-4-yl)oxy)phenyl)-N-phenylcyclopropane-1,1-dicarboxamide, optionally substituted 4-(4-(1-(phenylcarbamoyl)cyclopropane-1-carboxamido)phenoxy)quinolin-7-yl (1R,5S)-3,8-diazabicyclo[3.2.1]octane-8-carboxylate, optionally substituted 4-(4-(1-(phenylcarbamoyl)cyclopropane-1-carboxamido)phenoxy)quinolin-6-yl piperazine-1-carboxylate, optionally substituted 4-(4-(1-(phenylcarbamoyl)cyclopropane-1-carboxamido)phenoxy)quinazolin-7-yl piperazine-1-carboxylate, or 4-(4-(1-(phenylcarbamoyl)cyclopropane-1-carboxamido)phenoxy)quinolin-7-yl (1R,5S)-3,6-diazabicyclo[3.1.1]heptane-6-carboxylate.

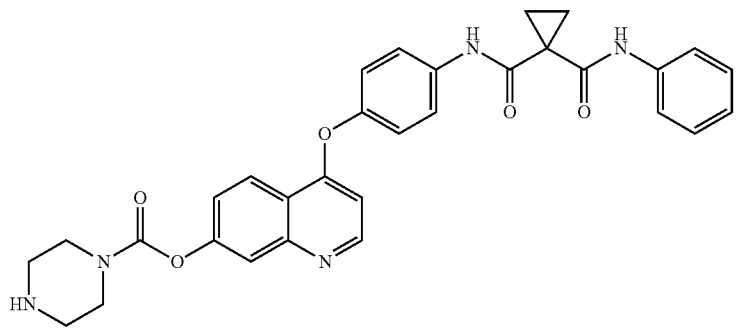

4-(4-(1-phenylcarbamoyl)cyclopropane-1-carboxamido)phenoxy)quinolin-7-yl piperazine-1-carboxylate -continued

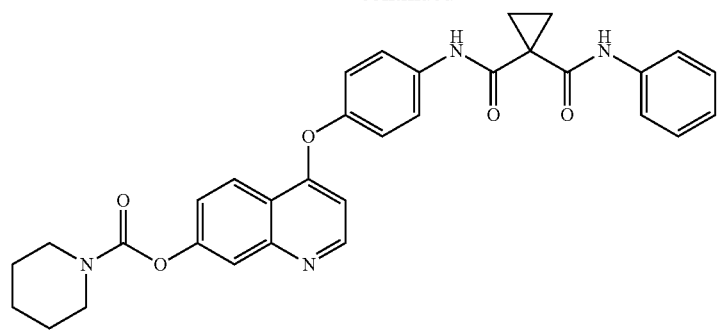

4-(4-(1-phenylcarbamoyl)cyclopropane-1-carboxamido)phenoxy)quinolin-7-yl piperidine-1-carboxylate

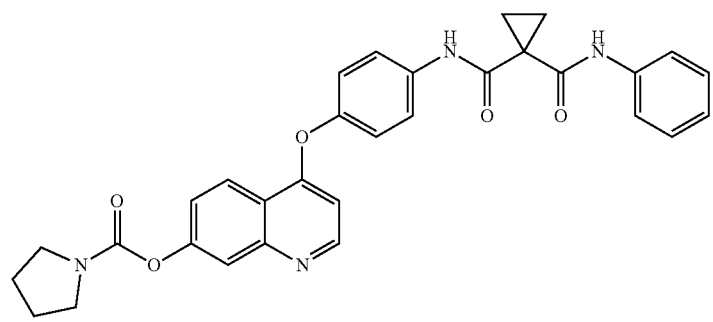

4-(4-(1-phenylcarbamoyl)cyclopropane-1-carboxamido)phenoxy)quinolin-7-yl pyrrolidine-1-carboxylate

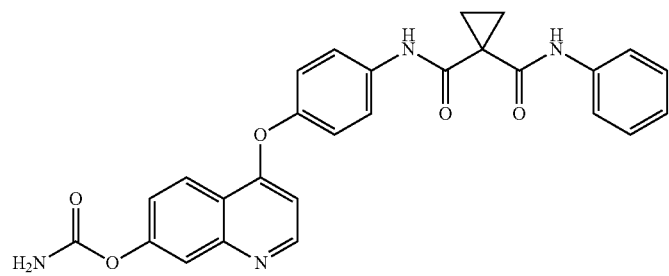

4-(4-(1-phenylcarbamoyl)cyclopropane-1-carboxamido)phenoxy)quinolin-7-yl carbamate

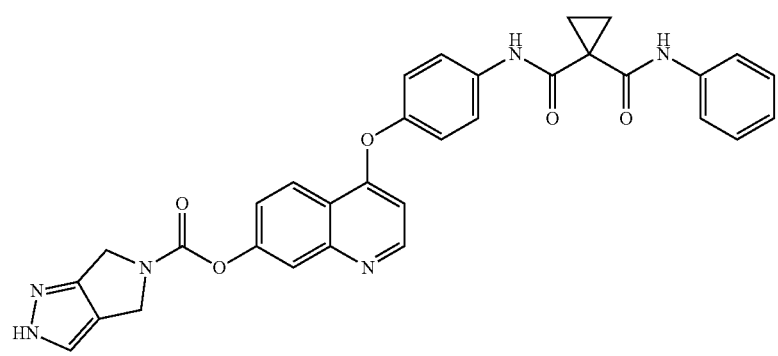

4-(4-(1-phenylcarbamoyl)cyclopropane-1-carboxamido)phenoxy)quinolin-7-yl 2,6-dihydropyrrolo[3,4-c]pyrazole-5(4H)-carboxylate

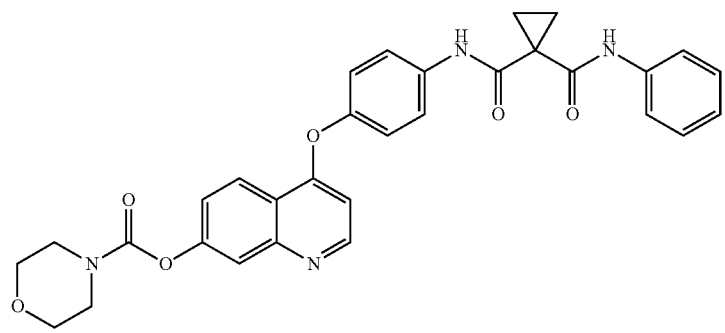

4-(4-(1-phenylcarbamoyl)cyclopropane-1-carboxamido)phenoxy)quinolin-7-yl morpholine-4-carboxylate

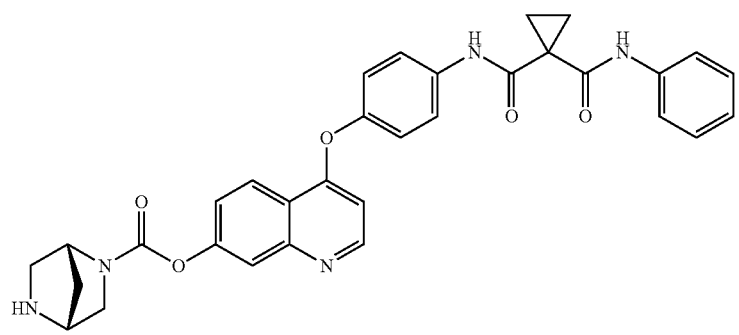

4-(4-(1-phenylcarbamoyl)cyclopropane-1-carboxamido)phenoxy)quinolin-7-yl (1R,4R)-2,5 diazabicyclo[2.2.1]heptane-2-carboxylate

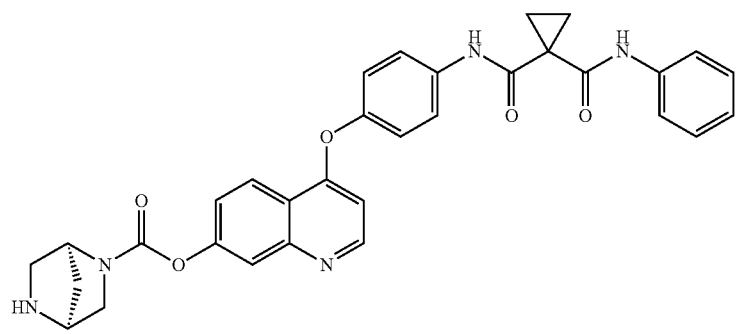

4-(4-(1-phenylcarbamoyl)cyclopropane-1-carboxamido)phenoxy)quinolin-7-yl (1S,4S)-2,5 diazabicyclo[2.2.1]heptane-2-carboxylate

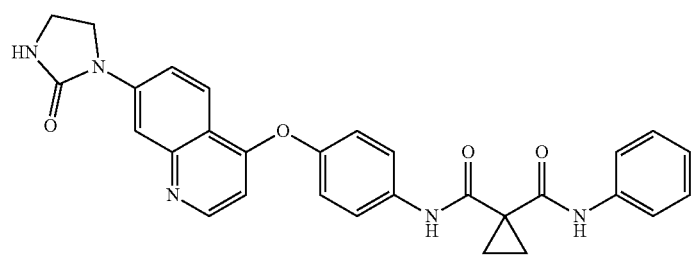

N-(4-((7-(2-oxoimidazolidin-1-yl)quinolin-4-yl)oxy)phenyl)-N-phenylcyclopropane-1,1-dicarboxamide -continued

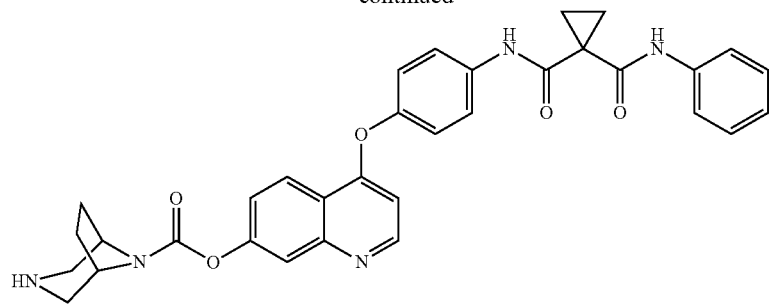

4-(4-(1-phenylcarbamoyl)cyclopropane-1-carboxamido)phenoxy)quinolin-7-yl
(1R,5S)-3,8-diazabicyclo[3.2.1]octane-8-carboxylate

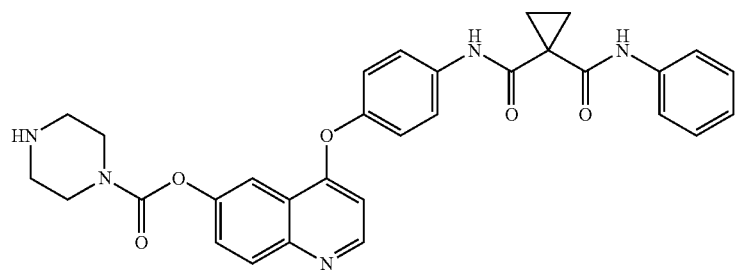

4-(4-(1-phenylcarbamoyl)cyclopropane-1-carboxamido)phenoxy)quinolin-6-yl piperazine-
1-carboxylate

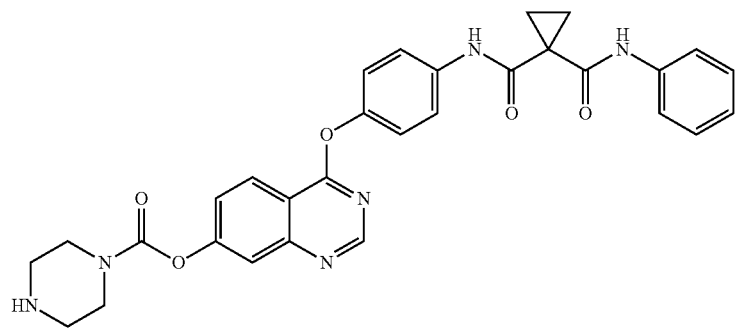

4-(4-(1-phenylcarbamoyl)cyclopropane-1-carboxamido)phenoxy)quinazolin-7-yl
piperazine-1-carboxylate

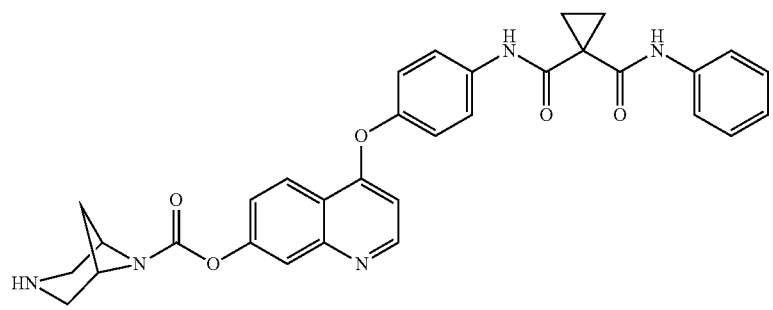

4-(4-(1-phenylcarbamoyl)cyclopropane-1-carboxamido)phenoxy)quinolin-7-yl
(1R,5S)-3,6-diazabicyclo[3.1.1]heptane-6-carboxylate Some embodiments include one of the compounds below:

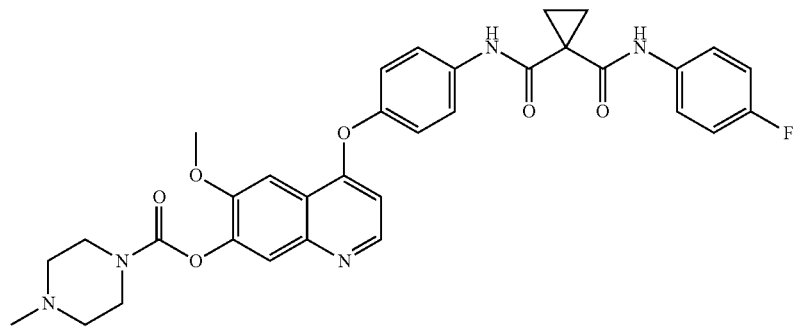

4-(4-(1-((4-fluorophenyl)carbamoyl)cyclopropane-1-carboxamido)phenoxy)-6-methoxyquinolin-7-yl 4-methylpiperazine-1-carboxylate

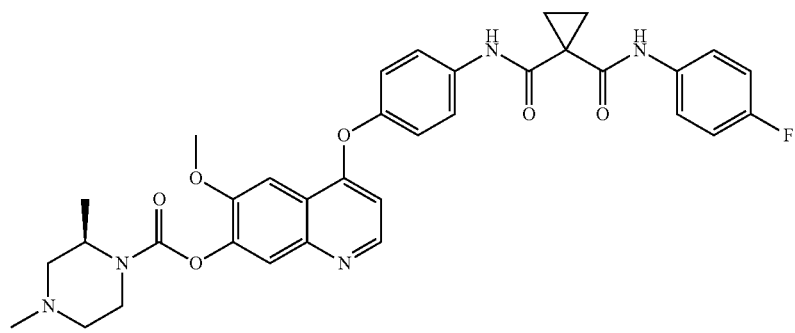

4-(4-(1-((4-fluorophenyl)carbamoyl)cyclopropane-1-carboxamido)phenoxy)-6-methoxyquinolin-7-yl (R)-2,4-dimethylpiperazine-1-carboxylate

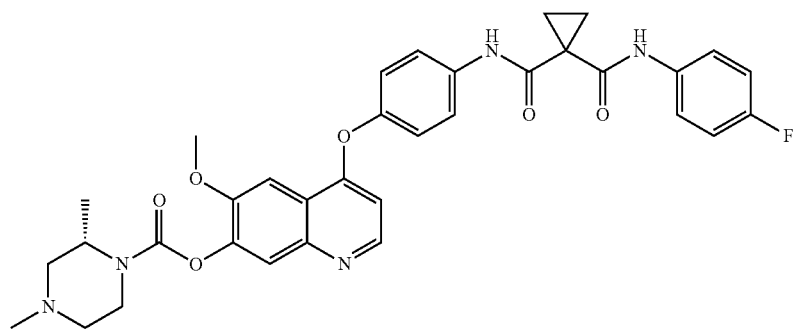

4-(4-(1-((4-fluorophenyl)carbamoyl)cyclopropane-1-carboxamido)phenoxy)-6-methoxyquinolin-7-yl (S)-2,4-dimethylpiperazine-1-carboxylate

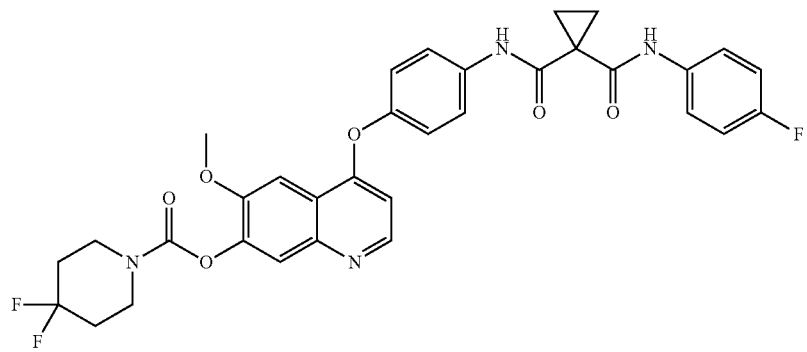

4-(4-(1-((4-fluorophenyl)carbamoyl)cyclopropane-1-carboxamido)phenoxy)-6-methoxyquinolin-7-yl 4,4-difluoropiperidine-1-carboxylate

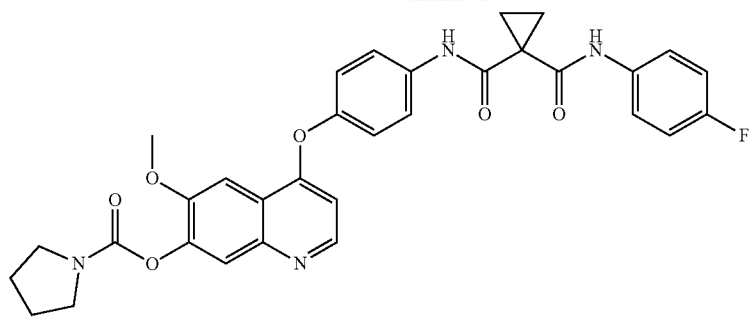

4-(4-(1-((4-fluorophenyl)carbamoyl)cyclopropane-1-carboxamido)phenoxy)-6-methoxyquinolin-7-yl pyrrolidine-1-carboxylate

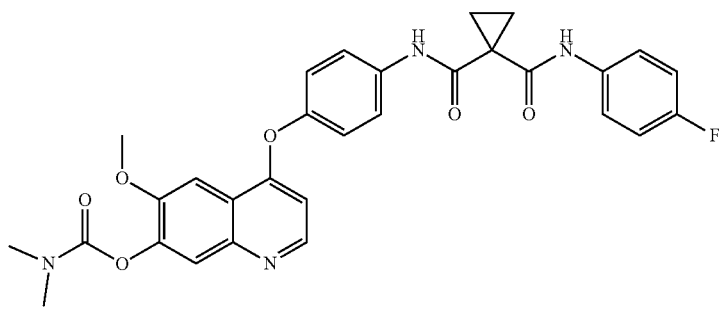

4-(4-(1-((4-fluorophenyl)carbamoyl)cyclopropane-1-carboxamido)phenoxy)-6-methoxyquinolin-7-yl dimethylcarbamate

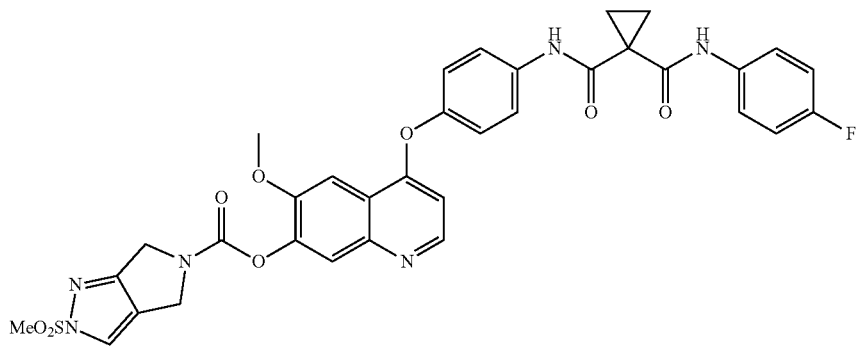

4-(4-(1-((4-fluorophenyl)carbamoyl)cyclopropane-1-carboxamido)phenoxy)-6-methoxyquinolin-7-yl 2-(methylsulfonyl)-2,6-dihydropyrrolo[3,4-c]pyrazole-5(4H)-carboxylate

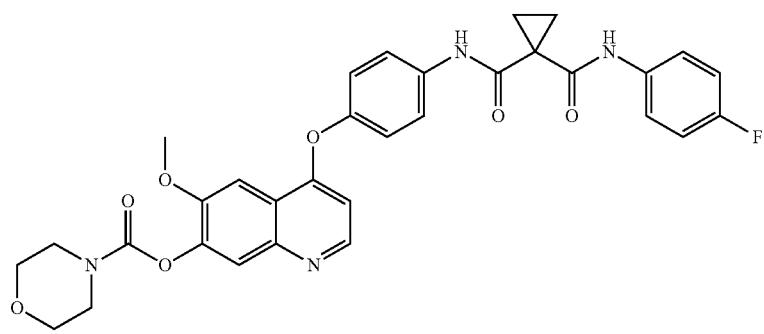

4-(4-(1-((4-fluorophenyl)carbamoyl)cyclopropane-1-carboxamido)phenoxy)-6-methoxyquinolin-7-yl morpholine-4-carboxylate

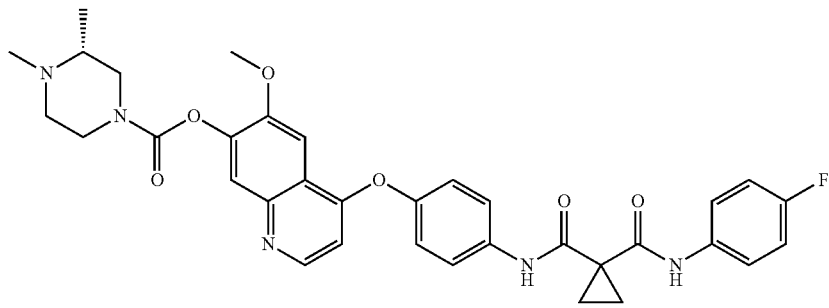

4-(4-(1-((4-fluorophenyl)carbamoyl)cyclopropane-1-carboxamido)phenoxy)-6-methoxyquinolin-7-yl
(R)-3,4-dimethylpiperazine-1-carboxylate

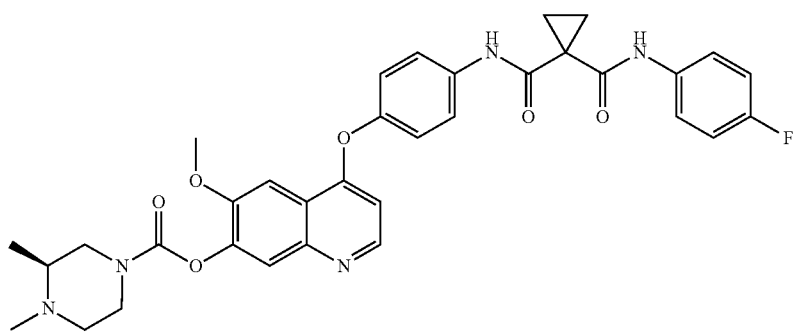

4-(4-(1-((4-fluorophenyl)carbamoyl)cyclopropane-1-carboxamido)phenoxy)-6-methoxyquinolin-7-yl
(S)-3,4-dimethylpiperazine-1-carboxylate

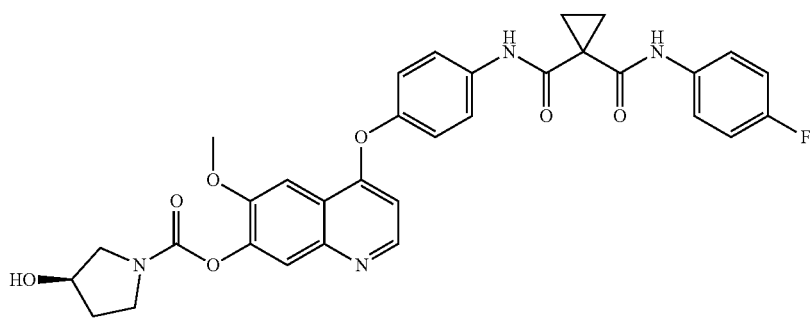

4-(4-(1-((4-fluorophenyl)carbamoyl)cyclopropane-1-carboxamido)phenoxy)-6-methoxyquinolin-7-yl
(R)-3-hydroxypyrrolidine-1-carboxylate

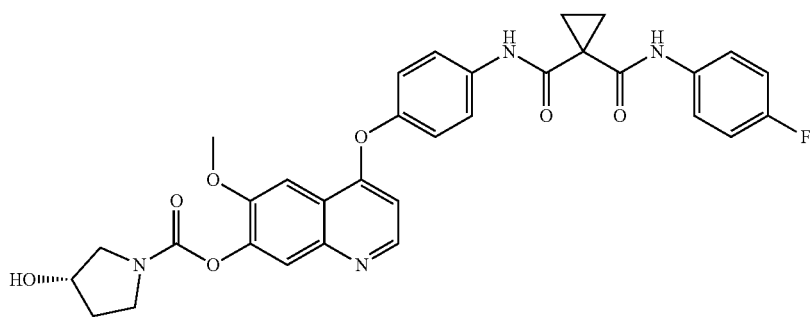

4-(4-(1-((4-fluorophenyl)carbamoyl)cyclopropane-1-carboxamido)phenoxy)-6-methoxyquinolin-7-yl
(S)-3-hydroxypyrrolidine-1-carboxylate

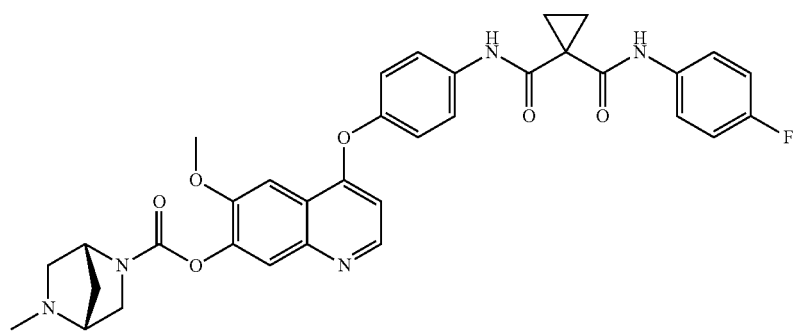

4-(4-(1-((4-fluorophenyl)carbamoyl)cyclopropane-1-carboxamido)phenoxy)-6-methoxyquinolin-7-yl
(1R,4R)-5-methyl-2,5-diazabicyclo[2.2.1]heptane-2-carboxylate

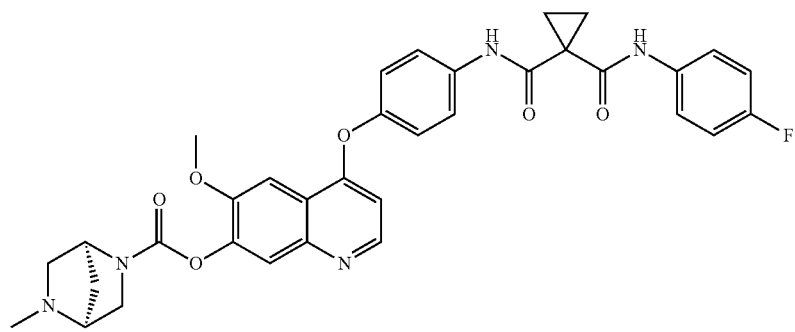

4-(4-(1-((4-fluorophenyl)carbamoyl)cyclopropane-1-carboxamido)phenoxy)-6-methoxyquinolin-7-yl
(1S,4S)-5-methyl-2,5-diazabicyclo[2.2.1]heptane-2-carboxylate-carboxylate

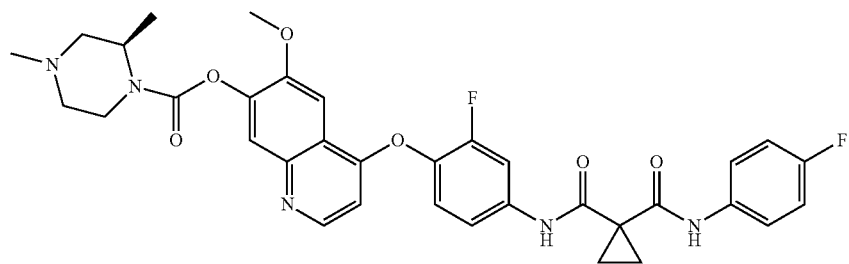

4-(2-fluoro-4-(1-((4-fluorophenyl)carbamoyl)cyclopropane-1-carboxamido)phenoxy)-6-methoxyquinolin-7-yl
(R)-2,4-dimethylpiperazine-1-carboxylate

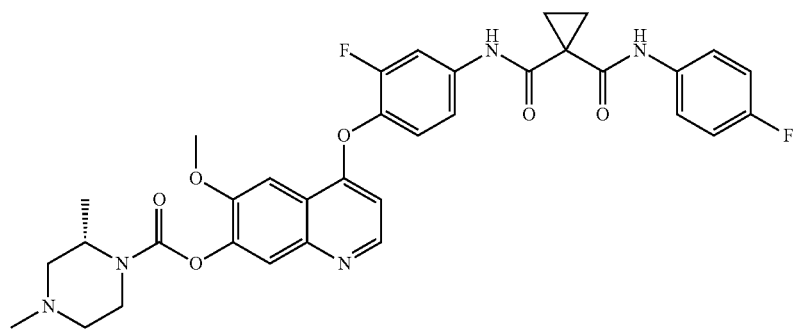

4-(2-fluoro-4-(1-((4-fluorophenyl)carbamoyl)cyclopropane-1-carboxamido)phenoxy)-6-
methoxyquinolin-7-yl (S)-2,4-dimethylpiperazine-1-carboxylate -continued

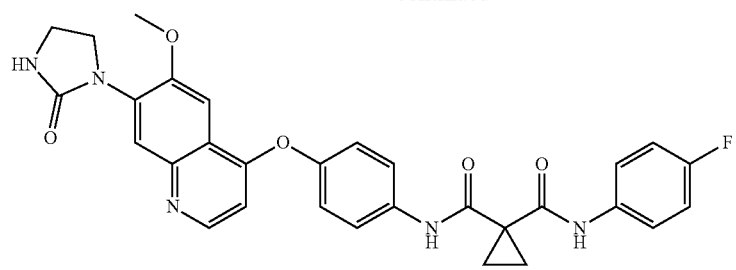

N-(4-fluorophenyl)-N-(4-((6-methoxy-7-(2-oxoimidazolidin-1-yl)quinolin-4-yl)oxy)phenyl) cyclopropane-1,1-dicarboxamide

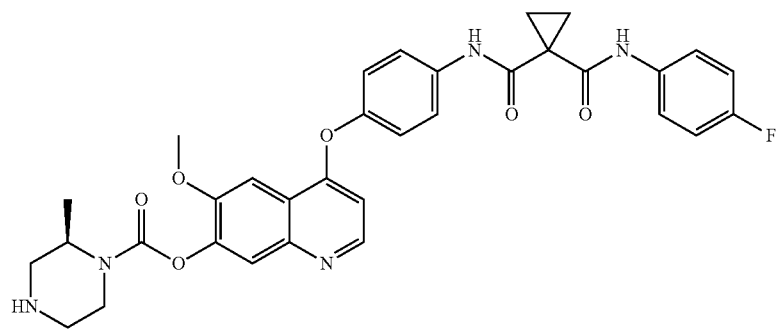

4-(4-(1-((4-fluorophenyl)carbamoyl)cyclopropane-1-carboxamido)phenoxy)-6-methoxyquinolin-7-yl (R)-2-methylpiperazine-1-carboxylate

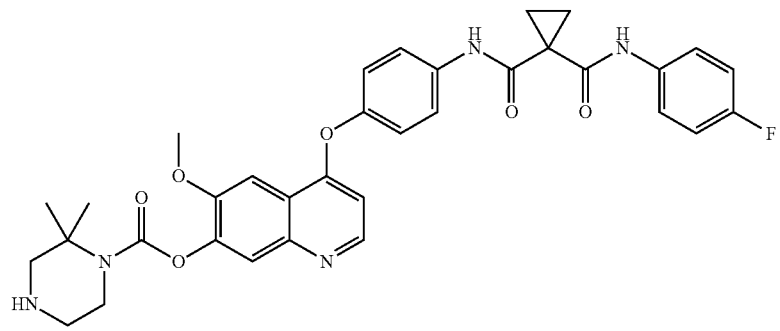

4-(4-(1-((4-fluorophenyl)carbamoyl)cyclopropane-1-carboxamido)phenoxy)-6-methoxyquinolin-7-yl 2,2-dimethylpiperazine-1-carboxylate

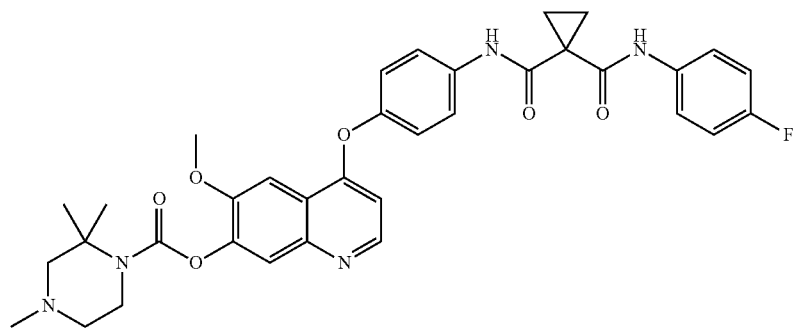

4-(4-(1-((4-fluorophenyl)carbamoyl)cyclopropane-1-carboxamido)phenoxy)-6-methoxyquinolin-7-yl 2,2,4-trimethylpiperazine-1-carboxylate -continued

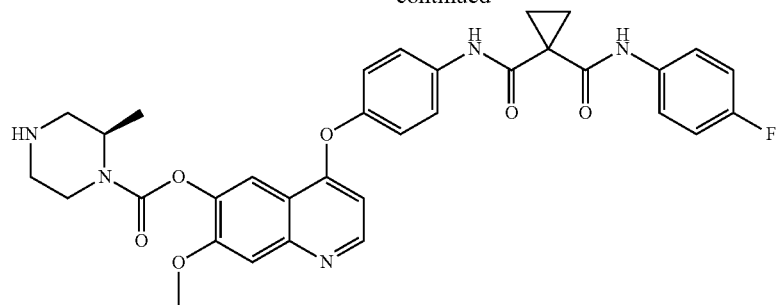

4-(4-(1-((4-fluorophenyl)carbamoyl)cyclopropane-1-carboxamido)phenoxy)-7-methoxyquinolin-
6-yl (R)-2-methylpiperazine-1-carboxylate

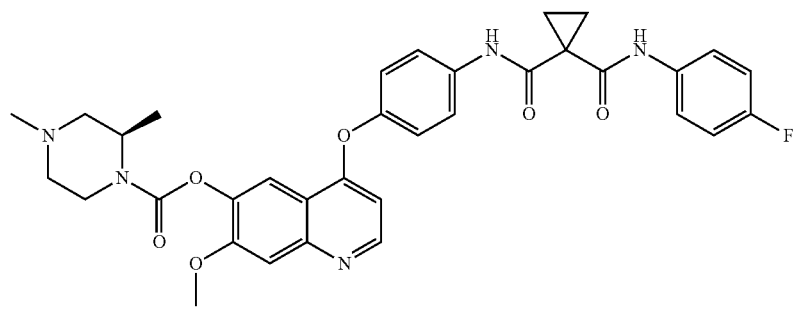

4-(4-(1-((4-fluorophenyl)carbamoyl)cyclopropane-1-carboxamido)phenoxy)-7-methoxyquinolin-
6-yl (R)-2,4-dimethylpiperazine-1-carboxylate

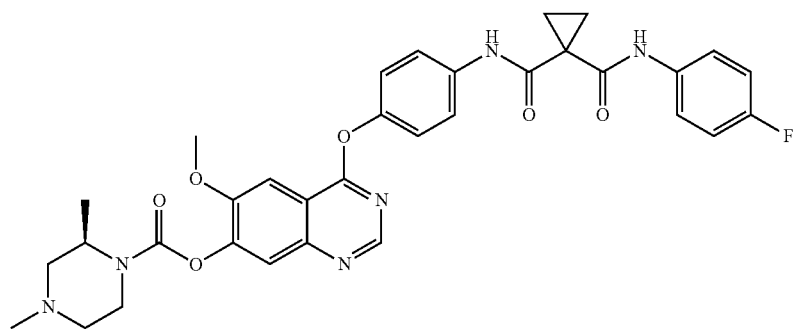

4-(4-(1-((4-fluorophenyl)carbamoyl)cyclopropane-1-carboxamido)phenoxy)-6-methoxyquinazolin-
7-yl (R)-2,4-dimethylpiperazine-1-carboxylate

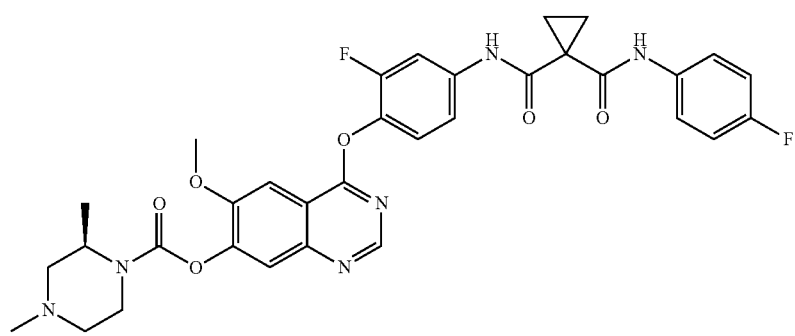

4-(2-fluoro-4-(1-((4-fluorophenyl)carbamoyl)cyclopropane-1-carboxamido)phenoxy)-6-
methoxyquinazolin-7-yl (R)-2,4-dimethylpiperazine-1-carboxylate Some embodiments include one of the compounds listed in Table A below, wherein each structure can be optionally substituted.
TABLE A
Compound structures and their ID numbers
Compound Structure and ID Number
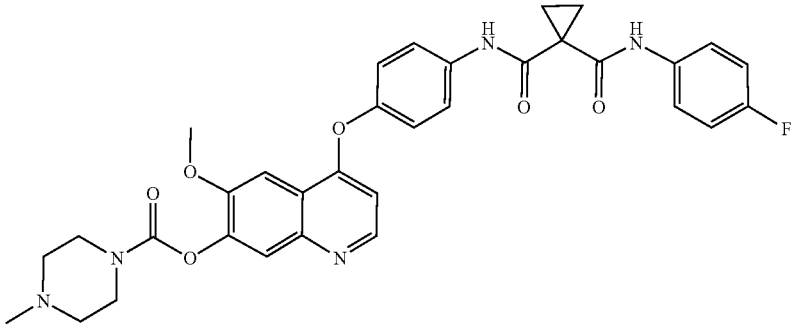 [SMILES: COc1cc2c(Oc3ccc(NC(=O)C4(C(=O)Nc5ccc(F)cc5)CC4)cc3)ccnc2cc1OC(=O)N1CCN(C)CC1]
1-10
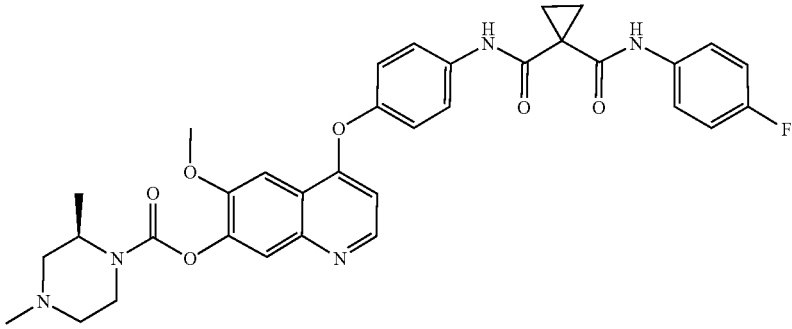 [SMILES: COc1cc2c(Oc3ccc(NC(=O)C4(C(=O)Nc5ccc(F)cc5)CC4)cc3)ccnc2cc1OC(=O)N1CCN(C)C[C@H]1C]
1-11
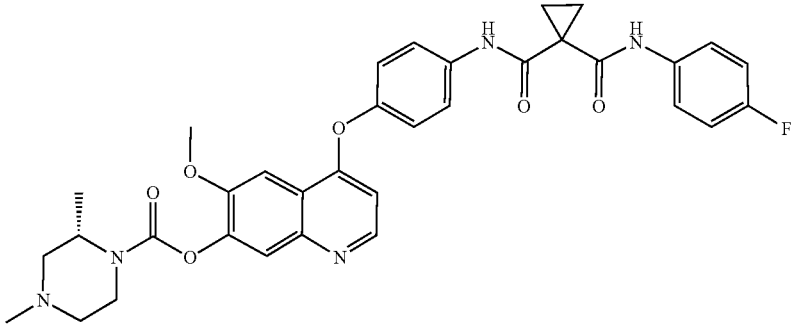 [SMILES: COc1cc2c(Oc3ccc(NC(=O)C4(C(=O)Nc5ccc(F)cc5)CC4)cc3)ccnc2cc1OC(=O)N1CCN(C)C[C@@H]1C]
1-12
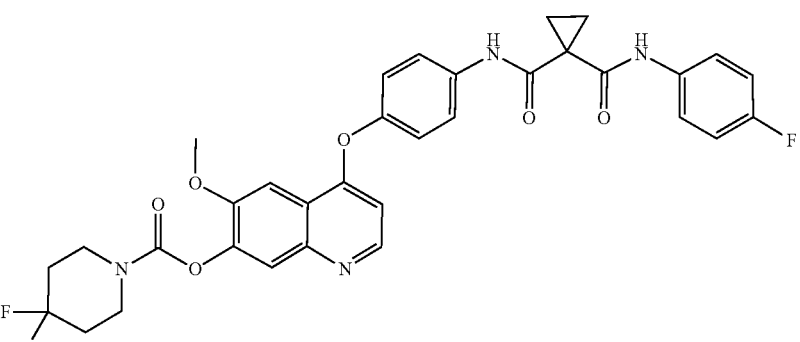
1-13

TABLE A-continued
Compound structures and their ID numbers
Compound Structure and ID Number
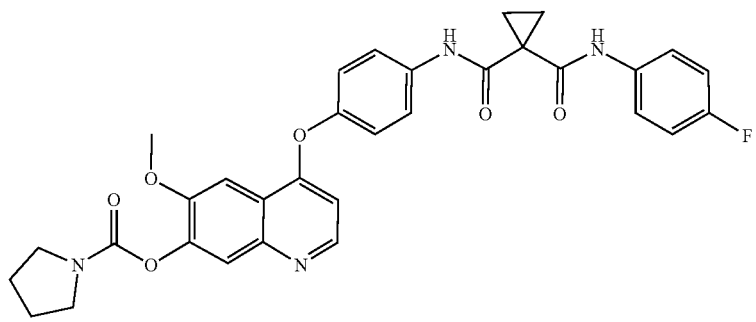 [SMILES: COc1cc2c(Oc3ccc(NC(=O)C4(C(=O)Nc5ccc(F)cc5)CC4)cc3)ccnc2cc1OC(=O)N1CCCC1]
1-14
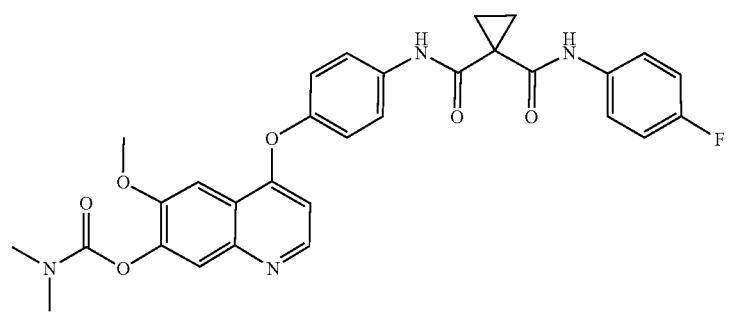 [SMILES: COc1cc2c(Oc3ccc(NC(=O)C4(C(=O)Nc5ccc(F)cc5)CC4)cc3)ccnc2cc1OC(=O)N(C)C]
1-15
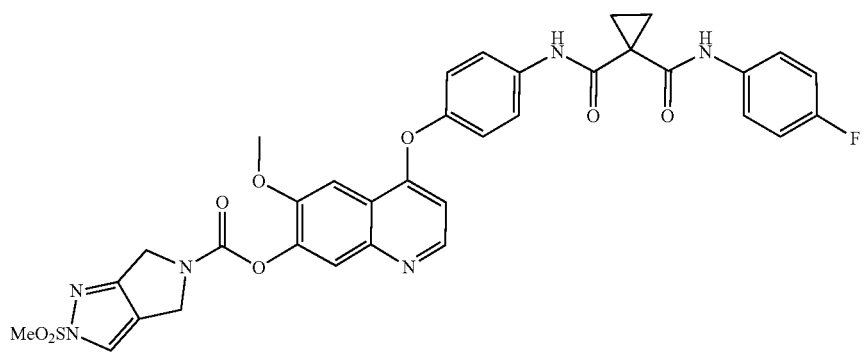
1-16
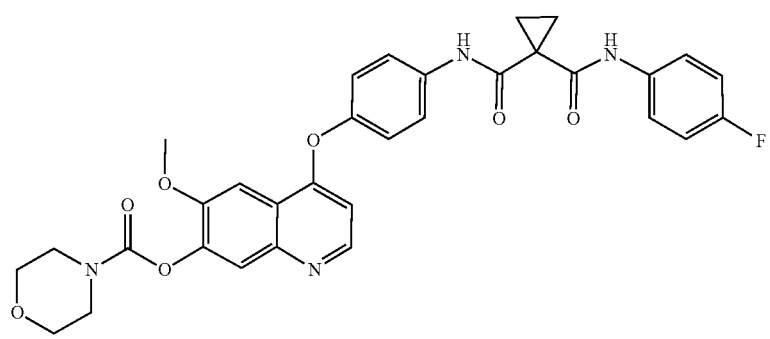 [SMILES: COc1cc2c(Oc3ccc(NC(=O)C4(C(=O)Nc5ccc(F)cc5)CC4)cc3)ccnc2cc1OC(=O)N1CCOCC1]
1-17

TABLE A-continued
Compound structures and their ID numbers
Compound Structure and ID Number
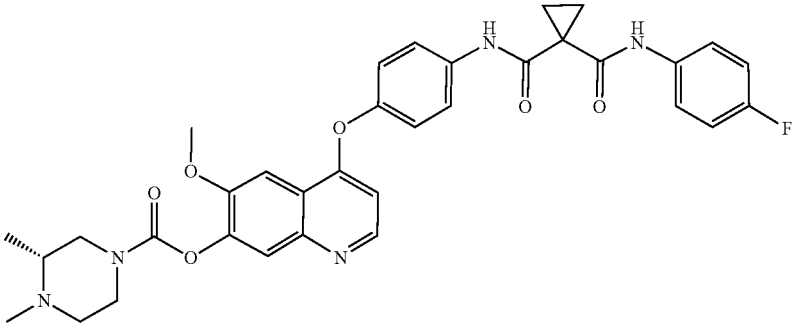 [SMILES: COc1cc2c(Oc3ccc(NC(=O)C4(C(=O)Nc5ccc(F)cc5)CC4)cc3)ccnc2cc1OC(=O)N1CCN(C)[C@H](C)C1]
2-2
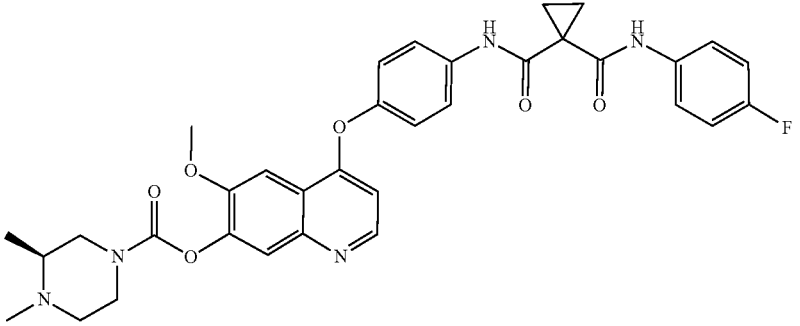 [SMILES: COc1cc2c(Oc3ccc(NC(=O)C4(C(=O)Nc5ccc(F)cc5)CC4)cc3)ccnc2cc1OC(=O)N1CCN(C)[C@@H](C)C1]
2-3
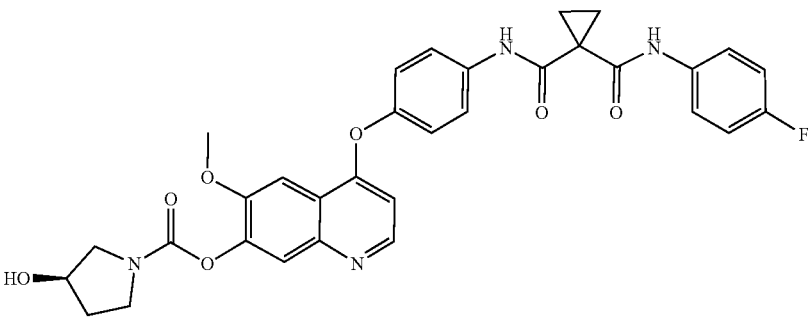 [SMILES: COc1cc2c(Oc3ccc(NC(=O)C4(C(=O)Nc5ccc(F)cc5)CC4)cc3)ccnc2cc1OC(=O)N1CC[C@@H](O)C1]
2-4
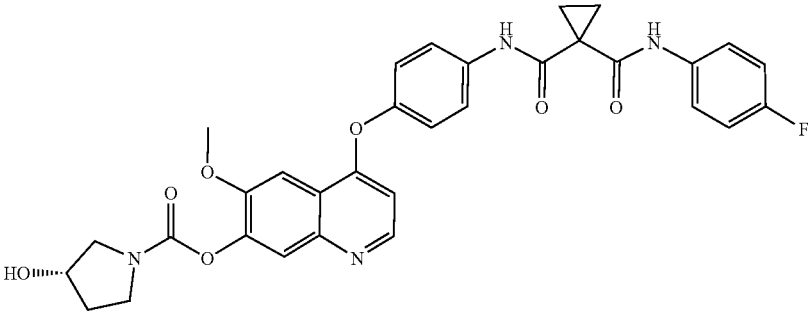 [SMILES: COc1cc2c(Oc3ccc(NC(=O)C4(C(=O)Nc5ccc(F)cc5)CC4)cc3)ccnc2cc1OC(=O)N1CC[C@H](O)C1]
2-5

TABLE A-continued

Compound structures and their ID numbers
Compound Structure and ID Number 2-6

2-7

3-5

3-6

TABLE A-continued

Compound structures and their ID numbers
Compound Structure and ID Number 10-2

4-2

4-3

4-4

TABLE A-continued

Compound structures and their ID numbers
Compound Structure and ID Number 4-5

4-6

5-10

6-2

TABLE A-continued

Compound structures and their ID numbers
Compound Structure and ID Number 6-3

6-4

6-5

6-6

TABLE A-continued
Compound structures and their ID numbers
Compound Structure and ID Number
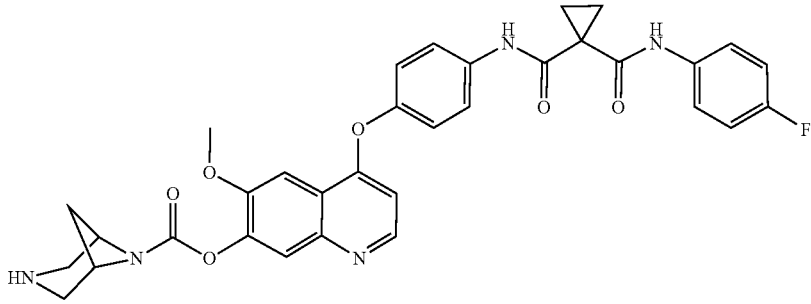 [SMILES: COc1cc2c(Oc3ccc(NC(=O)C4(C(=O)Nc5ccc(F)cc5)CC4)cc3)ccnc2cc1OC(=O)N1C2CNCC1C2]
6-7
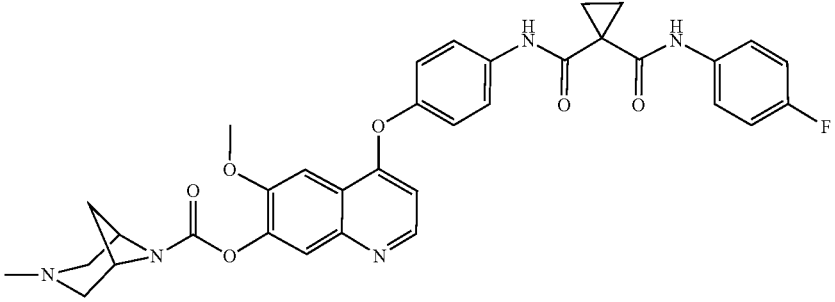 [SMILES: COc1cc2c(Oc3ccc(NC(=O)C4(C(=O)Nc5ccc(F)cc5)CC4)cc3)ccnc2cc1OC(=O)N1C2CC1CN(C)C2]
6-8
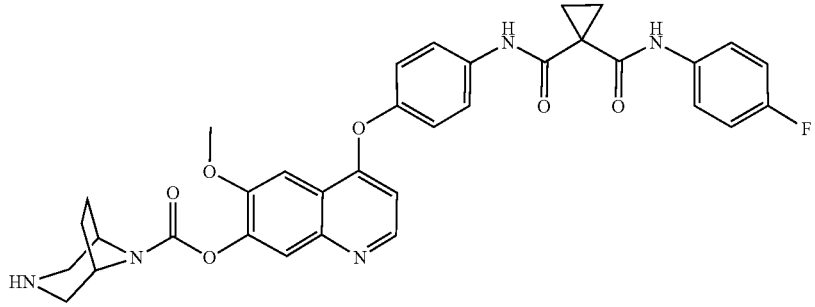 [SMILES: COc1cc2c(Oc3ccc(NC(=O)C4(C(=O)Nc5ccc(F)cc5)CC4)cc3)ccnc2cc1OC(=O)N1C2CCC1CNC2]
6-9
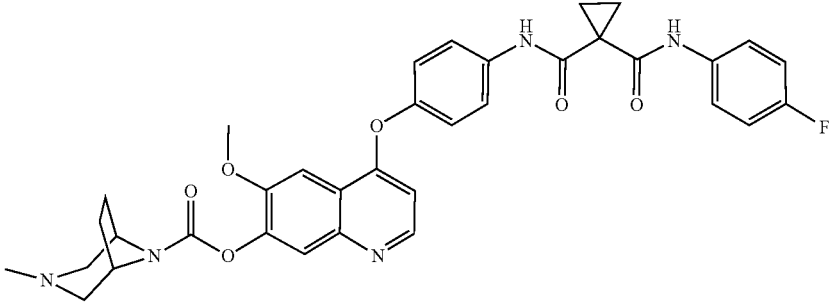 [SMILES: COc1cc2c(Oc3ccc(NC(=O)C4(C(=O)Nc5ccc(F)cc5)CC4)cc3)ccnc2cc1OC(=O)N1C2CCC1CN(C)C2]
6-10
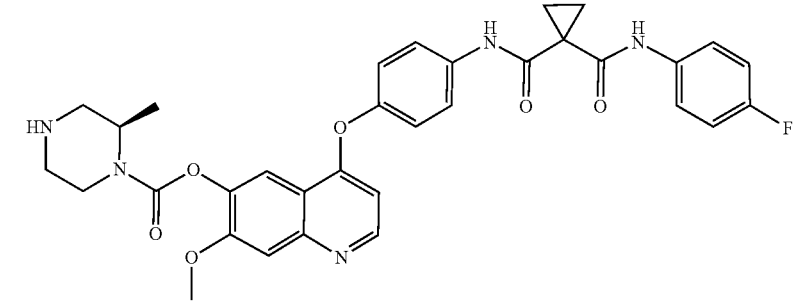 [SMILES: COc1cc2nccc(Oc3ccc(NC(=O)C4(C(=O)Nc5ccc(F)cc5)CC4)cc3)c2cc1OC(=O)N1CCNC[C@H]1C]
7-2

TABLE A-continued
Compound structures and their ID numbers
Compound Structure and ID Number
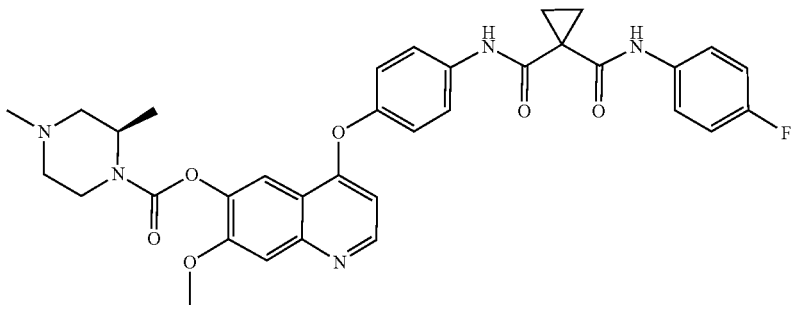 [SMILES: COc1cc2nccc(Oc3ccc(NC(=O)C4(C(=O)Nc5ccc(F)cc5)CC4)cc3)c2cc1OC(=O)N1CCN(C)C[C@H]1C]
7-3
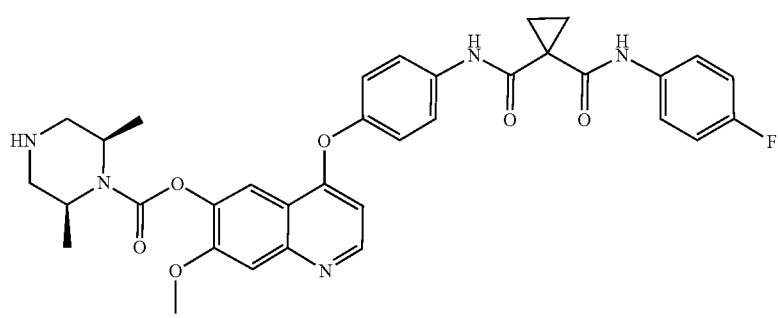 [SMILES: COc1cc2nccc(Oc3ccc(NC(=O)C4(C(=O)Nc5ccc(F)cc5)CC4)cc3)c2cc1OC(=O)N1[C@H](C)CNC[C@@H]1C]
7-4
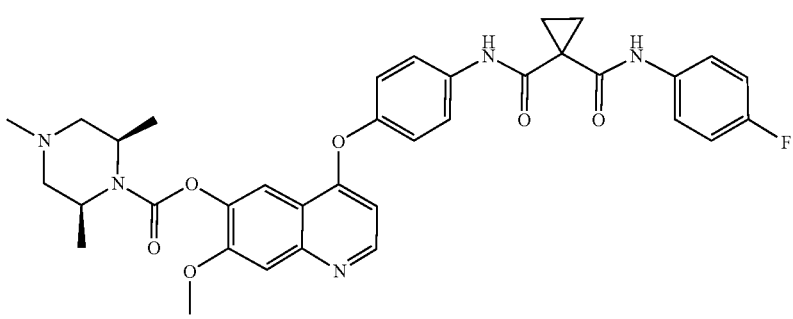 [SMILES: COc1cc2nccc(Oc3ccc(NC(=O)C4(C(=O)Nc5ccc(F)cc5)CC4)cc3)c2cc1OC(=O)N1[C@H](C)CN(C)C[C@@H]1C]
7-5
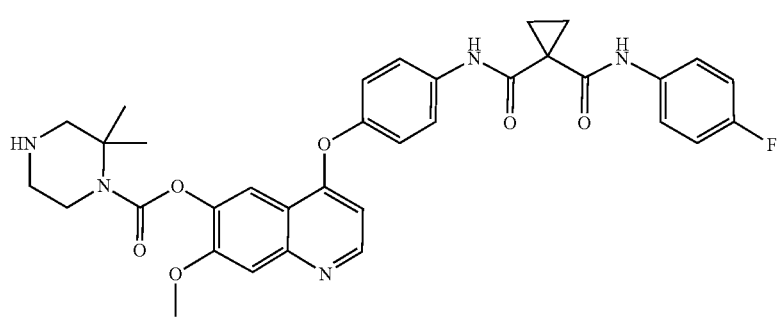 [SMILES: COc1cc2nccc(Oc3ccc(NC(=O)C4(C(=O)Nc5ccc(F)cc5)CC4)cc3)c2cc1OC(=O)N1CCNCC1(C)C]
7-6
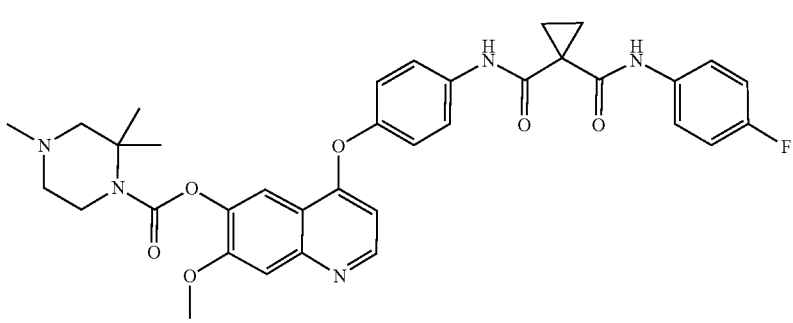 [SMILES: COc1cc2nccc(Oc3ccc(NC(=O)C4(C(=O)Nc5ccc(F)cc5)CC4)cc3)c2cc1OC(=O)N1CCN(C)CC1(C)C]
7-7

TABLE A-continued

Compound structures and their ID numbers
Compound Structure and ID Number 8-5

8-6

9-5

9-6

A hydrogen atom in any position of a subject compound may be replaced by a deuterium. In some embodiments, a subject compound contains a deuterium atom. In some embodiments, a subject compound contains multiple deuterium atoms.

A pharmaceutical composition comprising a subject compound may be adapted for oral, or parental, such as intravenous, intramuscular, topical, intraperitoneal, nasal, buccal, sublingual, or subcutaneous administration, or for administration via respiratory tract in the form of, for example, an aerosol or an air-suspended fine powder. The dosage of a subject compound may vary depending on the route of administration, body weight, age, the type and condition of the disease being treated. A pharmaceutical composition provided herein may optionally comprise two or more subject compounds without an additional therapeutic agent, or may comprise an additional therapeutic agent (i.e., a therapeutic agent other than a compound provided herein). For example, the compounds of the invention can be used in combination with at least one other therapeutic agent. Therapeutic agents include, but are not limited to antibiotics, antiemetic agents, antidepressants, and antifungal agents, anti-inflammatory agents, antiviral agents, and anticancer agents that are known in the art. The pharmaceutical composition may be used for the treatment of cancer, and other kinases associated disorders in patients. The term "patient" herein means a mammal (e.g., a human or an animal). In some embodiments, the patient has cancer.

The pharmaceutical composition described herein can be prepared by combining a subject compound with at least one pharmaceutical acceptable inert ingredient, such as a carrier, excipient, filler, lubricant, flavoring agent, buffer, etc., selected on the basis of the chosen route of administration and standard pharmaceutical practice as described, for example, in Remington's Pharmaceutical Sciences, 2005, the disclosure of which is hereby incorporated herein by reference, in its entirety. The relative proportions of active ingredient and carrier may be determined, for example, by the solubility and chemical nature of the subject compounds, chosen route of administration and standard pharmaceutical practice.

Some embodiments include a method of treating a disease or a disorder associated with kinases comprising administering a therapeutically effective amount of a subject compound or a pharmaceutical composition comprising a subject compound to a patient in need thereof. The term a "therapeutically effective amount" herein refers to an amount of a subject compound or a pharmaceutical composition of the present invention provided herein sufficient to be effective in inhibiting kinases and thus providing a benefit in the treatment of cancer, infectious diseases and other kinases associated disorders, to delay or minimize symptoms associated with cancer, infectious diseases and other kinases associated disorders, or to ameliorate a disease or infection or cause thereof. The term "treatment" refers to causing a therapeutically beneficial effect, such as ameliorating existing symptoms, ameliorating the underlying causes of symptoms, postponing, preventing the further development of a disorder, or reducing the severity of symptoms that are otherwise expected to develop without treatment.

Experimental Section:

Preparation of Compounds

The compounds of the disclosure can be made using procedures known in the art. The following reaction schemes show typical procedures, but those skilled in the art will recognize that other procedures can also be suitable for using to prepare these compounds. For examples in Formula I and II, wherein $R^1$ is not hydrogen, those skilled in the art will recognize that changes to the requisite reagents can be made at the appropriate steps in the synthetic methods outlined below. Reactions may involve monitoring for consumption of starting materials, and there are many methods for the monitoring, including but not limited to thin layer chromatography (TLC) and liquid chromatography mass spectrometry (LCMS). Those skilled in the art will recognize that any synthetic method specified in the examples shown below can be substituted by other non-limiting methods when suitable.

Some of the techniques, solvents, and reagents can be referred to by their abbreviations as follows:
Acetonitrile: MeCN or ACN
Aqueous: aq.
Benzyl: Bn
N,O-Bis(trimethylsilyl)acetamide: BSA
4,5-Bis(diphenylphosphino)-9,9-dimethylxanthene: xantphos
Compound: compd
Dichloromethane: DCM
Diisopropylethylamine: DIPEA, DIEA or iPr$_2$NEt
1,2-Dimethoxyethane: DME
Dimethylformamide: DMF
Dimethylsulfoxide: DMSO
Equivalents: equiv.
Ether or diethyl ether: Et$_2$O
Ethyl acetate: AcOEt or EtOAc
Example: Ex. or ex.
Formic acid: FA
Grams: g
High performance liquid chromatography: HPLC
Inhibition: Inh.
Liquid chromatography mass spectrometry: LCMS or LC-MS
Methanol: MeOH
Microliter: L
Micrometer: m
Milligram: mg
Milliliter: mL
Millimole: mmol
Nuclear magnetic resonance spectroscopy: NMR
Phosphoryl chloride: POCl$_3$
Preparative HPLC: Prep-HPLC
Preparative TLC: Prep-TLC
Retention time: t$_R$
Room temperature (ambient, ~25° C.): rt or RT
Potassium tert-butoxide: t-BuOK
Preparative HPLC: Prep-HPLC
Preparative TLC: Prep-TLC
Sodium methoxide: NaOMe
Supercritical Fluid Chromatography: SFC
Temperature: temp.
Tetrahydrofuran: THE
Thin layer chromatography: TLC
Tris(dibenzylideneacetone)dipalladium: Pd$_2$(dba)$_3$
Triethylamine: Et$_3$N or TEA
Trifluoroacetic acid: TFA
Trifluoromethanesulfonic anhydride: Tf$_2$O
Triphosgene: Bis(trichloromethyl) carbonate In the synthetic schemes described below, unless otherwise indicated all temperatures are set forth in degrees Celsius and all parts and percentages are by weight. Reagents and solvents were purchased from commercial suppliers such as Aldrich Chemical Company and were used without further purification unless otherwise indicated. Tetrahydrofuran (THF) and N,N-dimethylformamide (DMF) were purchased from commercial sources in Sure Seal bottles and used as received.

The reactions set forth below were done generally under a positive pressure of argon or nitrogen at an ambient temperature (unless otherwise stated) in anhydrous solvents. Glassware was oven dried and/or heat dried. The reactions were assayed by TLC and/or analyzed by LC-MS and terminated as judged by the consumption of starting material. Analytical thin layer chromatography (TLC) was performed on glass plates pre-coated with silica gel 60 F254 0.25 mm plates (EM Science), and visualized with UV light (254 nm) and/or heating with commercial ethanolic phosphomolybdic acid. preparative thin layer chromatography (TLC) was performed on glass-plates pre-coated with silica gel 60 F254 0.5 mm plates (20×20 cm, from commercial sources) and visualized with UV light (254 nm).

Work-ups were typically done by doubling the reaction volume with the reaction solvent or extraction solvent and then washing with the indicated aqueous solutions using 25% by volume of the extraction volume unless otherwise indicated. Product solutions were dried over anhydrous $Na_2SO_4$ and/or $Mg_2SO_4$ prior to filtration and evaporation of the solvents under reduced pressure on a rotary evaporator and noted as solvents removed in vacuo. Column chromatography was completed under positive pressure using 230-400 mesh silica gel.

$^1$H-NMR spectra and $^{13}$C-NMR were recorded on a Varian Mercury-VX400 instrument operating at 400 MHZ. NMR spectra were obtained as $CDCl_3$ solutions (reported in ppm), using chloroform as the reference standard (7.27 ppm for the proton and 77.00 ppm for carbon), $CD_3OD$ (3.4 and 4.8 ppm for the protons and 49.3 ppm for carbon), DMSO-$d_6$ (2.49 ppm for proton), or internally tetramethylsilane (0.00 ppm) when appropriate. Other NMR solvents were used as needed.

Some of the typical synthetic methods are described in the examples shown below.

Method 1:

Example 1: Synthesis of 4-(4-(1-((-fluorophenyl)carbamoyl)cyclopropane-1-carboxamido)phenoxy)-6-methoxyquinolin-7-yl 4-methylpiperazine-1-carboxylate

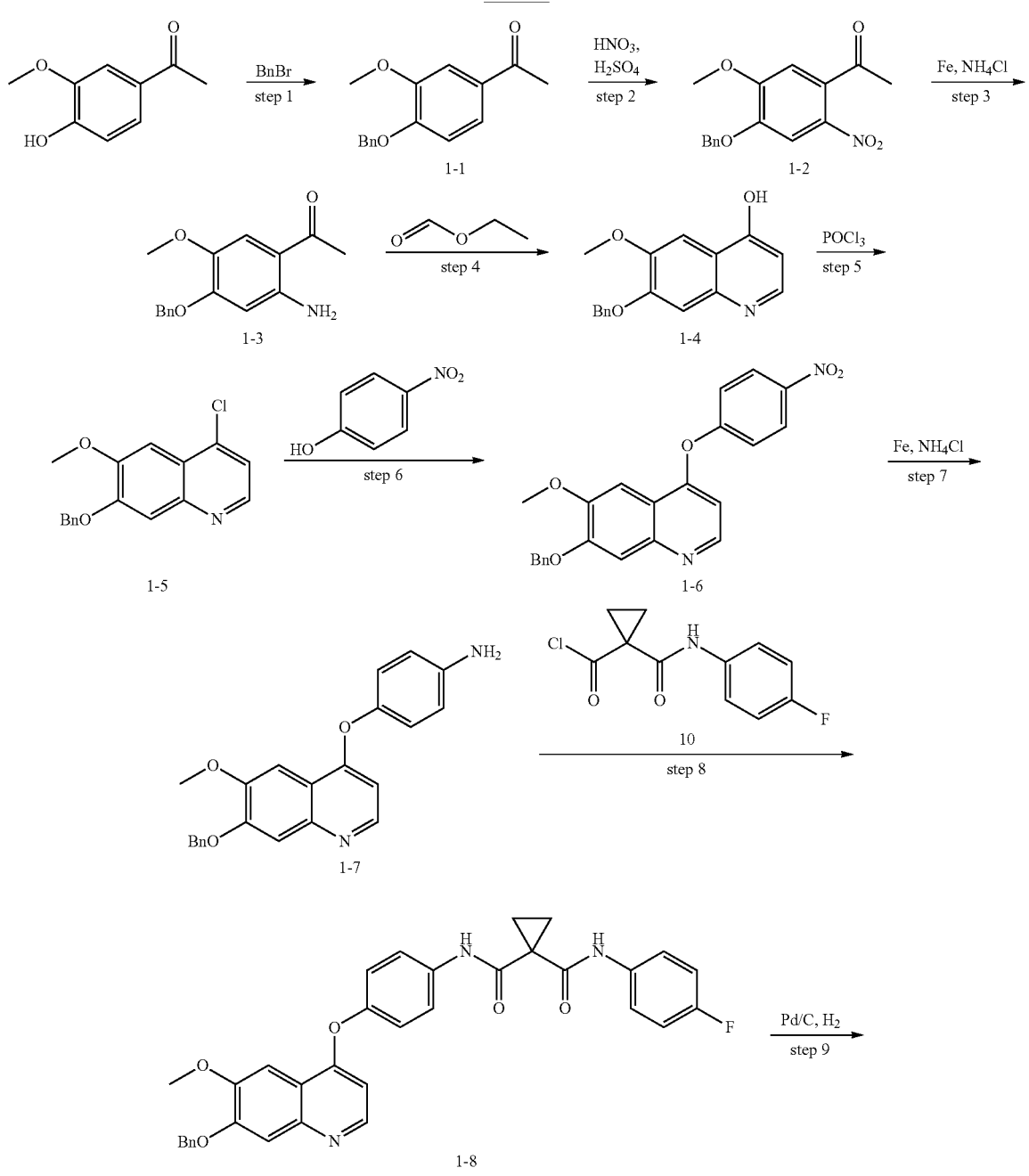

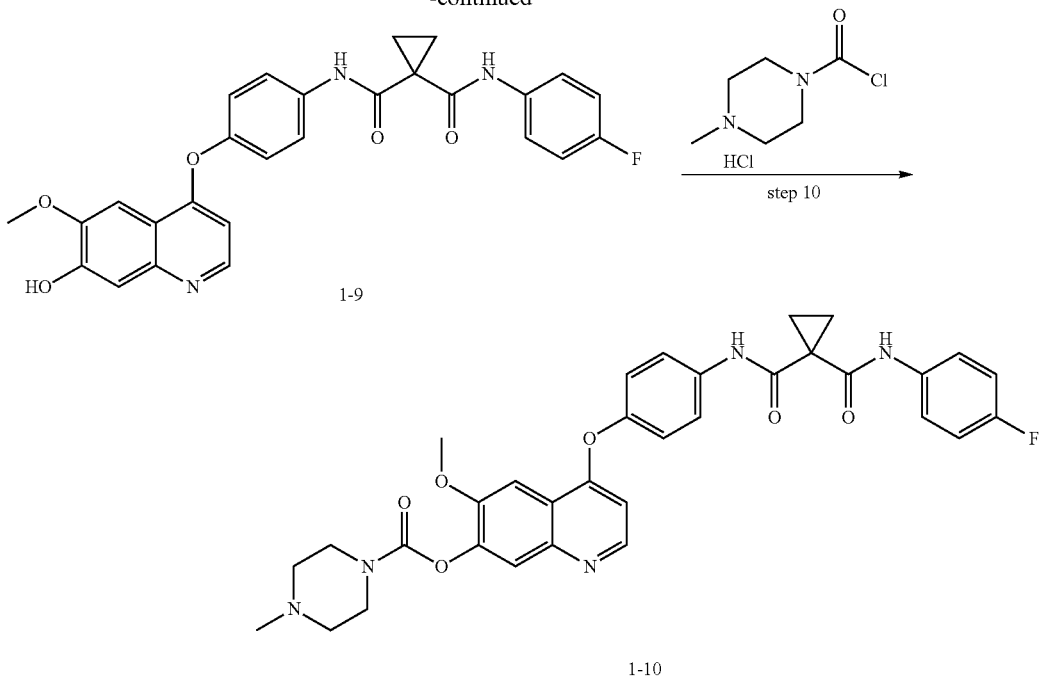

Step 1:
To a stirred solution of 10.0 g (60.2 mmol) of 1-(4-hydroxy-3-methoxyphenyl)ethan-1-one in 200 mL of DMF were added 12.5 g (90.5 mmol) of $K_2CO_3$ and 11.3 g (66.07 mmol) of benzyl bromide. The reaction mixture was stirred at 40° C. for 1 h under $N_2$ atmosphere. It was diluted with 500 mL of water, and filtered; the filter cake was washed with water to obtain compound 1-1, which was used in the next step without further purification. LC-MS: m/e=257 [M+H]$^+$.

Step 2:
To a stirred solution of 26.0 g (101.6 mmol) of compound 1-1 in 400 mL of dichloromethane was added 10.6 mL (238.1 mmol) of $HNO_3$ dropwise at 0° C. After 20 min, 8.2 mL (154.7 mmol) of $H_2SO_4$ was added dropwise at 0° C. The reaction mixture was stirred at 0° C. for 45 min, additional 7.25 mL (162.3 mmol) of $HNO_3$ was added dropwise at 0° C. The mixture was stirred at 0° C. for 2 h, and quenched by addition of 800 mL ice-water. It was extracted with three 500 mL portions of dichloromethane; the combined organic extracts were washed with brine, and dried over anhydrous $Na_2SO_4$. After filtration, the filtrate was concentrated to afford a residue, which was purified by trituration with 200 mL of methanol. After filtration, the filter cake was washed with methanol to obtain compound 1-2. LC-MS: m/e=302 [M+H]$^+$.

Step 3:
To a stirred solution of 24.5 g (81.32 mmol) of compound 1-2 in 375 mL of $H_2O$-EtOH (2:3) were added 17.4 g (325.3 mmol) of $NH_4Cl$ and 22.8 g (407.0 mmol) of iron powder at room temperature. The reaction mixture was stirred at 90° C. for 2 h under nitrogen atmosphere. The mixture was cooled to room temperature, diluted with 250 mL of ethyl acetate. The resulting mixture was filtered; the filtrate was washed with $H_2O$ and brine, then dried over $Na_2SO_4$. The filtrate was concentrated under vacuum to afford compound 1-3. LC-MS: m/e=272 [M+H]$^+$.

Step 4:
To a stirred solution of 13.7 g (50.5 mmol) of compound 1-3 in 350 mL of DME was added 20.3 mL (252.6 mmol) of ethyl formate and 45.0 g (30%, 251.8 mmol) of NaOMe at room temperature. The reaction mixture was stirred at room temperature overnight. It was adjusted to pH 7 with 1 N HCl and filtered; the filter cake was washed with water to obtain compound 1-4, which was used in the next step without further purification. LC-MS: m/e=282 [M+H]$^+$.

Step 5:
To a stirred solution of 13.0 g (46.3 mmol) of compound 1-4 in 200 mL of toluene was added 100 mL of $POCl_3$ at room temperature. The mixture was stirred at 100° C. for 2 h and concentrated under vacuum. The residue was adjusted to pH 8 with 1N NaOH and saturated $NaHCO_3$ solution, and extracted with three 400 mL portions of ethyl acetate. The combined organic extracts were washed with brine, and dried over anhydrous $Na_2SO_4$. After filtration, the filtrate was concentrated to afford a residue, which was purified by chromatography on silica gel column eluting with 0 to 22% gradient of ethyl acetate in petroleum ether to compound 1-5. LC-MS: m/e=300 [M+H]$^+$.

Step 6:
To a stirred solution of 3.7 g (12.34 mmol) of compound 1-5 in 7.4 mL of xylene was added 16.7 mL (100.74 mmol) of DIPEA and 2.4 g (17.25 mmol) of 4-nitrophenol at room temperature. The mixture was stirred at 140° C. overnight under $N_2$ atmosphere and cooled to room temperature. The mixture was diluted with 50 mL of ethanol; the solid was collected by filtration and washed with cold ethanol to afford compound 1-6. LC-MS: m/e=403 [M+H]$^+$.

Step 7:
To a stirred solution of 5.1 g (12.67 mmol) of compound 1-6 and 2.7 g (50.7 mmol) of $NH_4Cl$ in 100 mL of EtOH—$H_2O$ (3:2) was added 3.55 g (63.4 mmol) of iron powder at room temperature. The mixture was stirred at 90° C. for 2 h under $N_2$ atmosphere and filtered; the filter cake was washed with methanol. The filtrate was concentrated under reduced pressure to remove methanol; the aqueous solution was extracted with three 200 mL portions of ethyl acetate. The combined organic extracts were washed with brine, and dried over anhydrous $Na_2SO_4$. After filtration, the filtrate was concentrated to afford a residue, which was purified by chromatography on silica gel column eluting with 0 to 75% gradient of ethyl acetate in petroleum ether to afford compound 1-7. LC-MS: m/e=373 [M+H]+.

Step 8:

To a stirred solution of 2.6 g (7.0 mmol) of compound 1-7 in 80 mL of THF were added 2.7 g (20.9 mmol) of DIEA and 2.5 g (10.4 mmol) of intermediate 10-1 in 3 mL THF dropwise at 0° C. The mixture was stirred at 0° C. for 2 h under nitrogen atmosphere and diluted with 50 mL of water. It was extracted with three 50 mL portions of ethyl acetate; the combined organic extracts were washed with brine, and dried over anhydrous $Na_2SO_4$. After filtration, the filtrate was concentrated to afford a residue, which was purified by chromatography on silica gel column eluting with 0 to 60% gradient of ethyl acetate in petroleum ether to afford compound 1-8. LC-MS: m/e=578 [M+H]+.

Step 9:

To a stirred solution of 2.8 g (4.9 mmol) of compound 1-8 in 110 mL of EtOH was added 0.6 g of 10% Pd/C. The mixture was stirred at room temperature overnight under hydrogen atmosphere using a hydrogen balloon. The mixture was filtered; the filter cake was washed with methanol. The filtrate was concentrated under vacuum to afford compound 1-9. LC-MS: m/e=488 [M+H]+.

Step 10:

To a stirred solution of 60 mg (0.12 mmol) of compound 1-9 in 4 mL of pyridine was added 53.9 mg (0.27 mmol) of 4-methylpiperazine-1-carbonyl chloride hydrochloride. The mixture was stirred at 60° C. for 1 h under nitrogen atmosphere and then concentrated under vacuum. The residue was diluted with 15 mL of water, extracted with three 20 mL portions of DCM. The combined organic extracts were washed with brine, and dried over anhydrous $Na_2SO_4$. After filtration, the filtrate was concentrated to afford a residue, which was purified by Prep-HPLC [SHIMADZU: Column, XBridge Prep C18 OBD Column, 5 µm, 19*150 mm; mobile phase, A: Water (10 mmol/L $NH_4HCO_3$) and B: ACN, (Gradient: 41% Phase B up to 55% in 8 min); Flow rate: 20 mL/min, Rt: 6.68 min, Detector, 254 nm UV] to give compound 1-10. LC-MS: m/e=614 [M+H]+.

Using the procedure outlined in Method 1, step 10, the following analogs in Table 1 were made from compound 1-9 by employing the requisite carbonyl chloride (Those listed are prepared, others are commercially available).

TABLE 1

Synthesis of carbamate analogs

| Carbonyl chloride | Structure | LCMS [M + 1]+ |
|---|---|---|
| 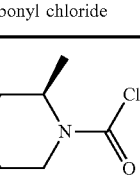 1 | 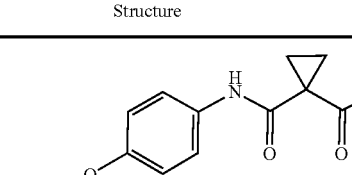 1-11 | 628 |
| 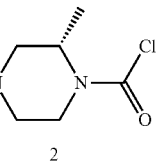 2 | 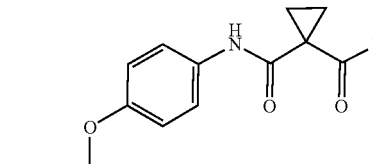 1-12 | 628 |

TABLE 1-continued
Synthesis of carbamate analogs
| Carbonyl chloride | Structure | LCMS [M + 1]+ |
|---|---|---|
| 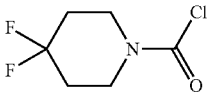 3 | 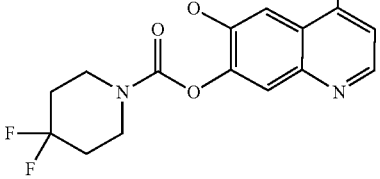 1-13 | 635 |
| | 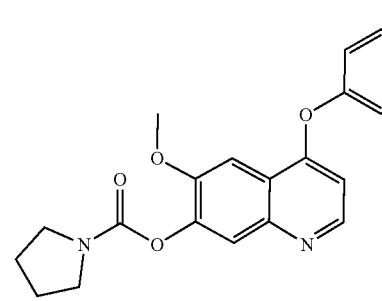 1-14 | 585 |
| | 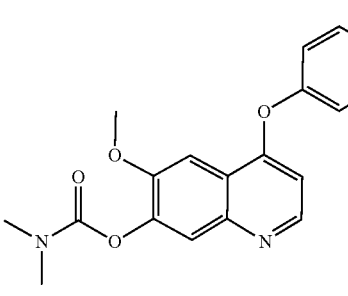 1-15 | 559 |
| 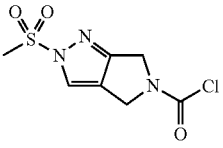 4 | 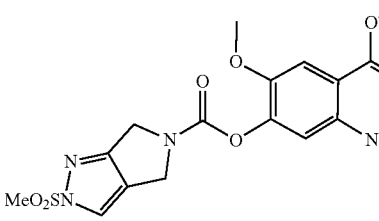 1-16 | 701 |

TABLE 1-continued
Synthesis of carbamate analogs
| Carbonyl chloride | Structure | LCMS [M + 1]+ |
|---|---|---|
| | 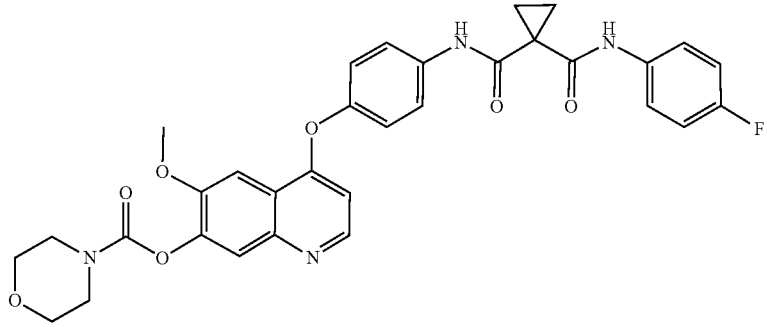<br>1-17 | 601 |
Method 2:
Example 2: Synthesis of 4-(4-(1-((-fluorophenyl)carbamoyl)cyclopropane-1-carboxamido)phenoxy)-6-methoxyquinolin-7-yl (R)-3,4-dimethylpiperazine-1-carboxylate
25
Scheme 2
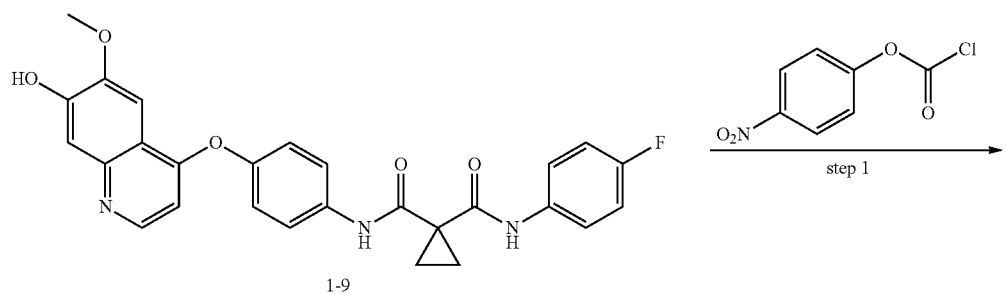
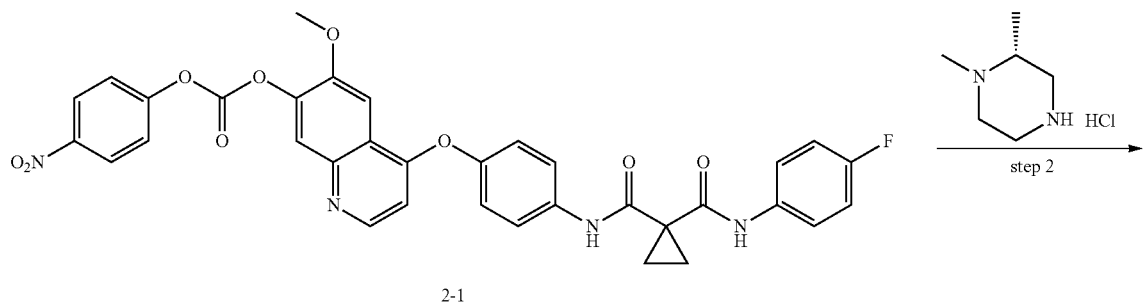

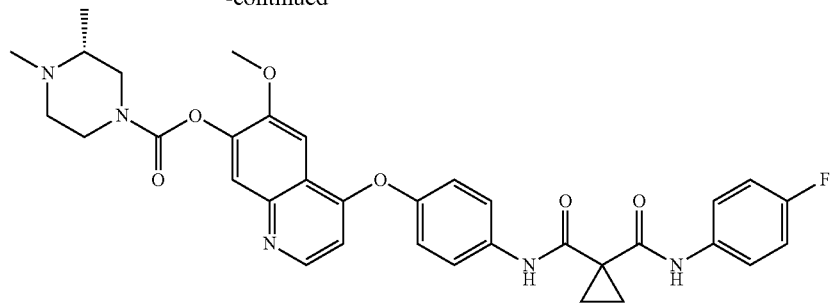

2-2

Step 1:

To a stirred solution of 1.0 g (2.1 mmol) of compound 1-9 in 30 mL of THF was added 0.40 g (3.1 mmol) of DIEA and 0.46 g (2.3 mmol) of 4-nitrophenyl carbonochloridate in 2 mL of THF at 0° C. The mixture was stirred at room temperature for 2 h and then quenched with water. It was extracted with three 50 mL portions of ethyl acetate; the combined organic extracts were washed with brine, and dried over anhydrous Na₂SO₄. After filtration, the filtrate was concentrated under vacuum to afford compound 2-1. LC-MS: m/e=653 [M+H]⁺.

Step 2:

To a stirred solution of 0.10 g (0.16 mmol) of compound 2-1 in 5 mL of THF was added 0.078 g (0.77 mmol) of Et₃N and 0.068 g (0.46 mmol) of (R)-1,2-dimethylpiperazine hydrochloride at room temperature. The mixture was stirred at rt for 3 h and extracted with three 15 mL portions of ethyl acetate. The combined organic extracts were washed with brine, and dried over anhydrous Na₂SO₄. After filtration, the filtrate was concentrated to afford a residue, which was purified by Prep-HPLC: [SHIMADZU: Column, XBridge Prep C18 OBD Column, 19*150 mm, 5 m; mobile phase, water (10 mmol/L NH₄HCO₃) and ACN (45% Phase B up to 53% in 8 min); Detector, 254 nm UV] to afford compound 2-2. LCMS: m/e=628 [M+H]⁺.

Using the procedure outlined in Method 2, step 2, the following analogs in Table 2 were made from compound 2-1 by employing the requisite amine.

TABLE 2

Synthesis of carbamate analogs (continued)

| Structure | LCMS [M + 1]+ |
|---|---|
| (2-3) | 628 |
| (2-4) | 601 |

TABLE 2-continued
Synthesis of carbamate analogs (continued)
| Structure | LCMS [M + 1]+ |
|---|---|
| 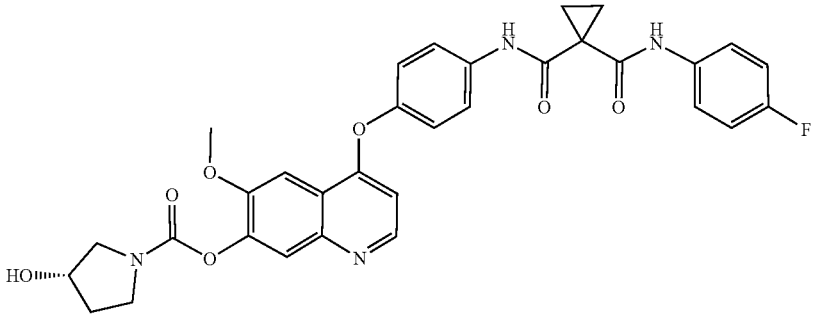 2-5 | 601 |
| 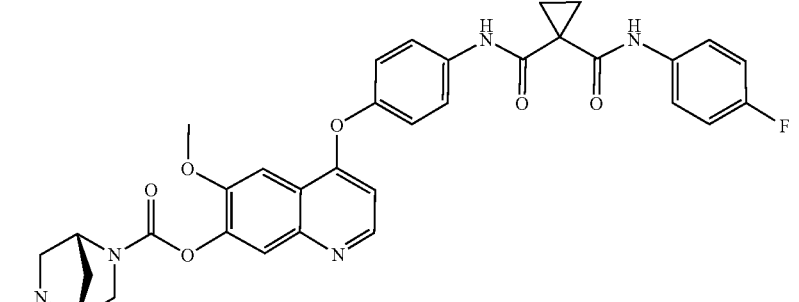 2-6 | 626 |
| 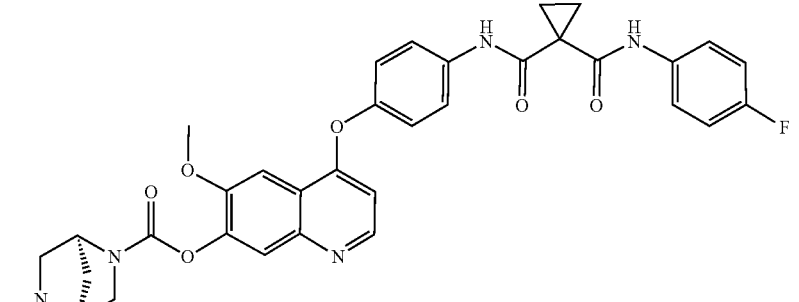 2-7 | 626 |

Method 3:

Example 3: Synthesis of 4-(2-fluoro-4-(1-((4-fluorophenyl)carbamoyl)cyclopropane-1-carboxamido)phenoxy)-6-methoxyquinolin-7-yl (R)-2,4-dimethylpiperazine-1-carboxylate Scheme 3

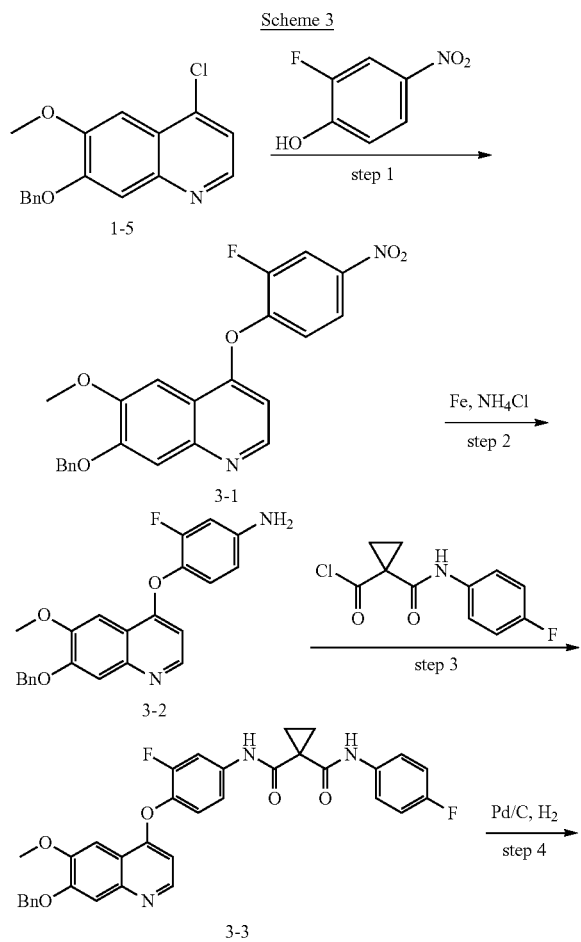

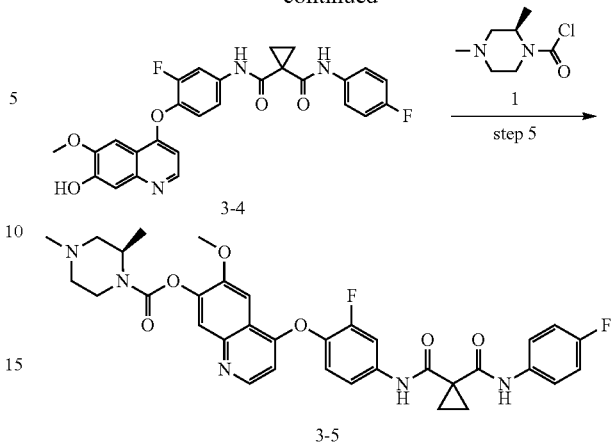

Step 1:
Compound 3-1 was prepared from intermediate 1-5, using the procedure described in Method 1, step 6, by employing 2-fluoro-4-nitrophenol as the coupling reagent. LC-MS: m/e=421 [M+H]$^+$.

Step 2:
Compound 3-2 was prepared from intermediate 3-1, using the procedure described in Method 1, step 7. LC-MS: m/e=391 [M+H]$^+$.

Step 3:
Compound 3-3 was prepared from intermediate 3-2, using the procedure described in Method 1, step 8. LC-MS: m/e=596 [M+H]$^+$.

Step 4:
Compound 3-4 was prepared from intermediate 3-3, using the procedure described in Method 1, step 9. LC-MS: m/e=506 [M+H]$^+$.

Step 5:
Compound 3-5 was prepared from intermediate 3-4, using the procedure described in Method 1, step 10. LC-MS: m/e=646 [M+H]$^+$.

Compound 3-6 was prepared from compound 3-4 coupling with intermediate 2 similarly.

TABLE 3

Synthesis of compound 3-6

| Carbonyl Chloride | Structure | LCMS [M + 1]+ |
|---|---|---|
| 2 | 3-6 | 646 |

Method 4:
Example 4: Synthesis of 4-(2-fluoro-4-(1-((4-fluorophenyl)carbamoyl)cyclopropane-1-carboxamido) phenoxy)-6-methoxyquinolin-7-yl (S)-3,4-dimethylpiperazine-1-carboxylate
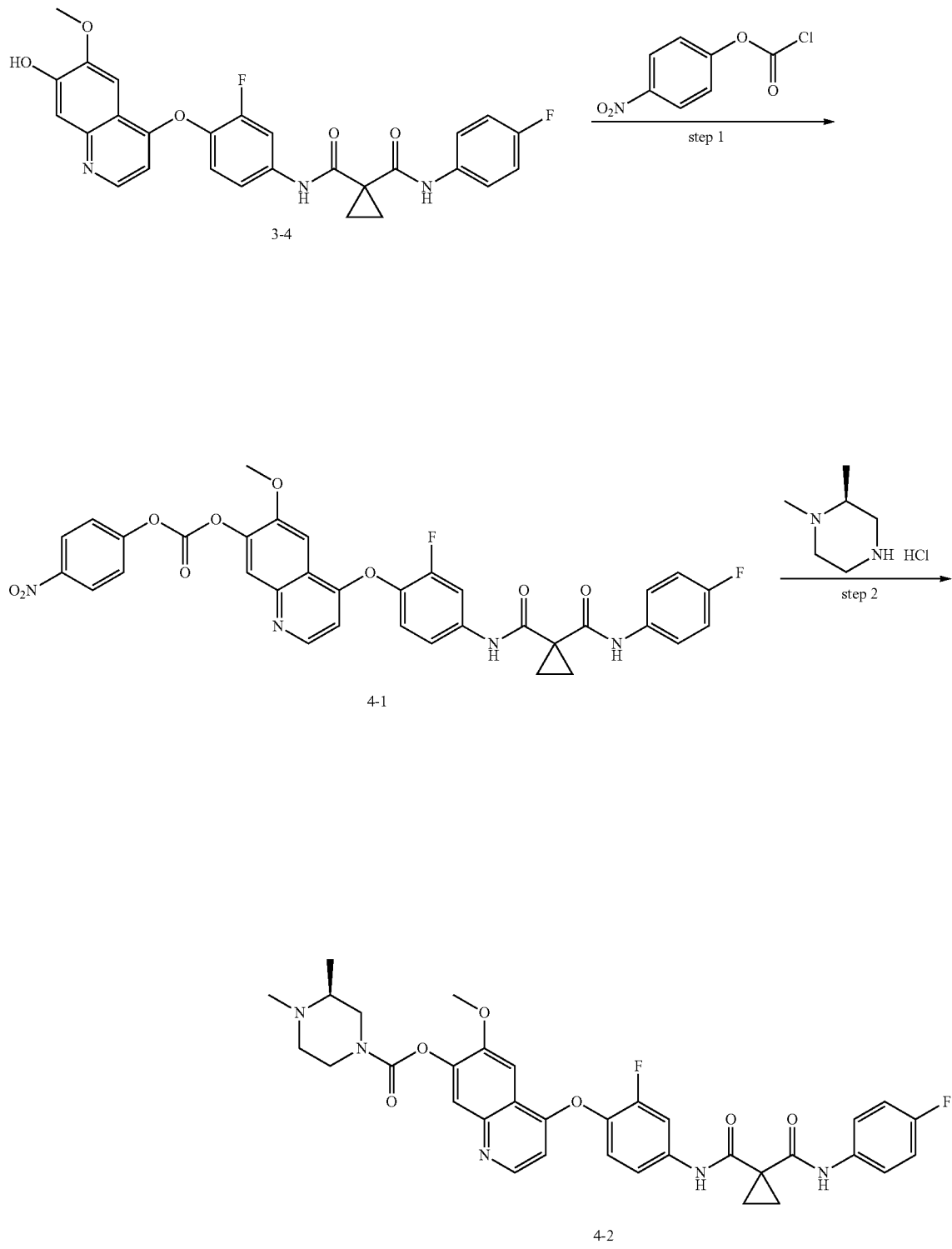

Step 1:
Following the procedure described in Method 2, step 1, compound 3-4 was converted to compound 4-1. LC-MS: m/e=671 [M+H]$^+$.

Step 2:
Following the procedure described in Method 2, step 2, compound 4-1 was converted to compound 4-2. LC-MS: m/e=646 [M+H]$^+$.

The following analogs in Table 4 were prepared similarly from compound 4-1 employing the requisite amine.

TABLE 4

Synthesis of heterocyclic analogs

| Structure | LCMS [M + 1]+ |
|---|---|
| 4-3 | 646 |
| 4-4 | 644 |
| 4-5 | 644 |

TABLE 4-continued
Synthesis of heterocyclic analogs
| Structure | LCMS [M + 1]+ |
|---|---|
| 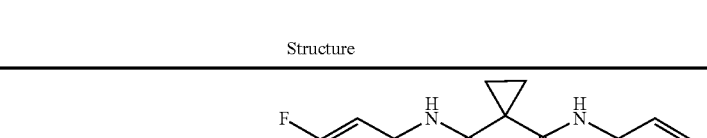 4-6 | 658 |
Method 5:
Example 5: Synthesis of 4-(4-(1-((-fluorophenyl)carbamoyl)cyclopropane-1-carboxamido)phenoxy)-7-methoxyquinolin-6-yl 4-methylpiperazine-1-carboxylate
Scheme 5
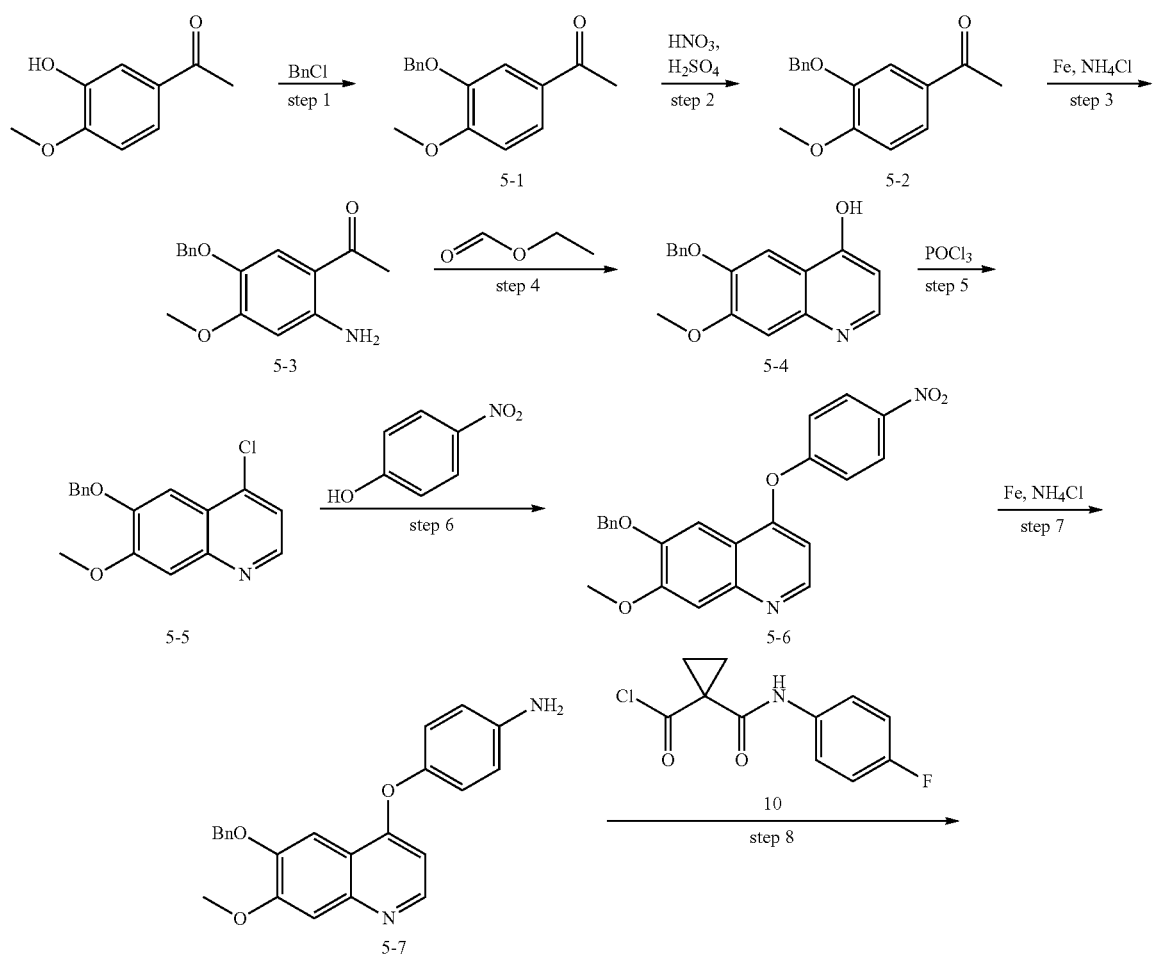

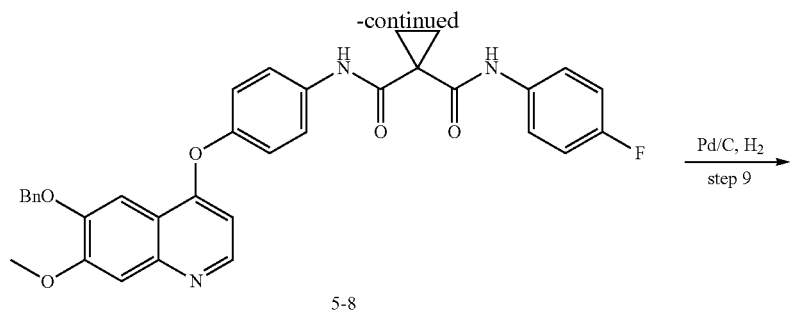

5-8

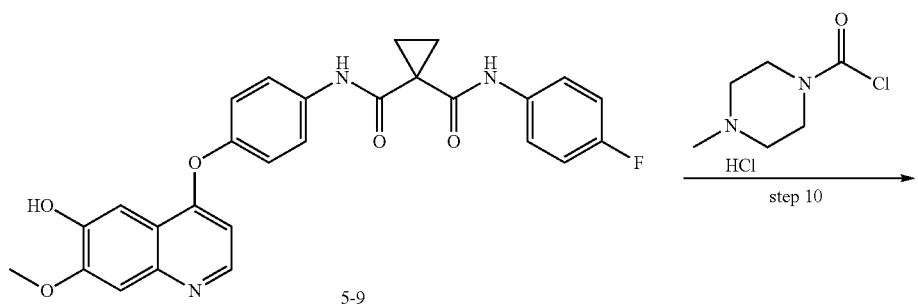

5-9

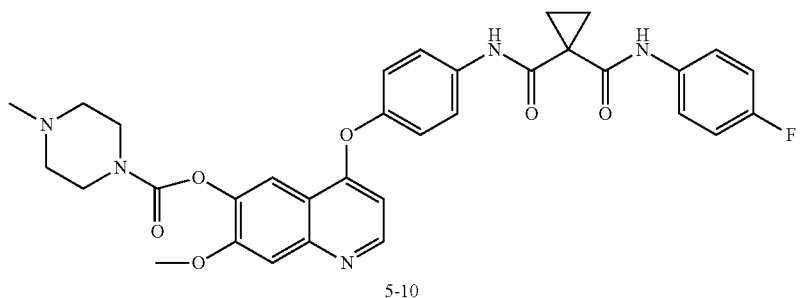 [SMILES: COc1cc2nccc(Oc3ccc(NC(=O)C4(C(=O)Nc5ccc(F)cc5)CC4)cc3)c2cc1OC(=O)N1CCN(C)CC1]

5-10

Step 1:
Following the procedure described in Method 1, step 1, compound 5-1 was prepared from 1-(3-hydroxy-4-methoxyphenyl)ethan-1-one similarly using benzyl chloride instead of benzyl bromide. LC-MS: m/e=257 [M+H]$^+$.

Step 2:
Following the procedure described in Method 1, step 2, compound 5-2 was prepared from compound 5-1 similarly. LC-MS: m/e=302 [M+H]$^+$.

Step 3:
Following the procedure described in Method 1, step 3, compound 5-3 was prepared from compound 5-2 similarly. LC-MS: m/e=272 [M+H]$^+$.

Step 4:
Following the procedure described in Method 1, step 4, compound 5-4 was prepared from compound 5-3 similarly. LC-MS: m/e=282 [M+H]$^+$.

Step 5:
Following the procedure described in Method 1, step 5, compound 5-5 was prepared from compound 5-4 similarly. LC-MS: m/e=300 [M+H]$^+$.

Step 6:
Following the procedure described in Method 1, step 6, compound 5-6 was prepared from compound 5-5 similarly. LC-MS: m/e=403 [M+H]$^+$.

Step 7:
Following the procedure described in Method 1, step 7, compound 5-7 was prepared from compound 5-6 similarly. LC-MS: m/e=373 [M+H]$^+$.

Step 8:
Following the procedure described in Method 1, step 8, compound 5-8 was prepared from compound 5-7 similarly. LC-MS: m/e=578 [M+H]$^+$.

Step 9:
Following the procedure described in Method 1, step 9, compound 5-9 was prepared from compound 5-8 similarly. LC-MS: m/e=488 [M+H]$^+$.

Step 10:
Following the procedure described in Method 1, step 10, compound 5-10 was prepared from compound 5-9 similarly. LC-MS: m/e=614 [M+H]$^+$.

Method 6:
Example 6: Synthesis of 4-(4-(1-((-fluorophenyl)carbamoyl)cyclopropane-1-carboxamido)phenoxy)-6-methoxyquinolin-7-yl 2,4,6-trimethylpiperazine-1-carboxylate
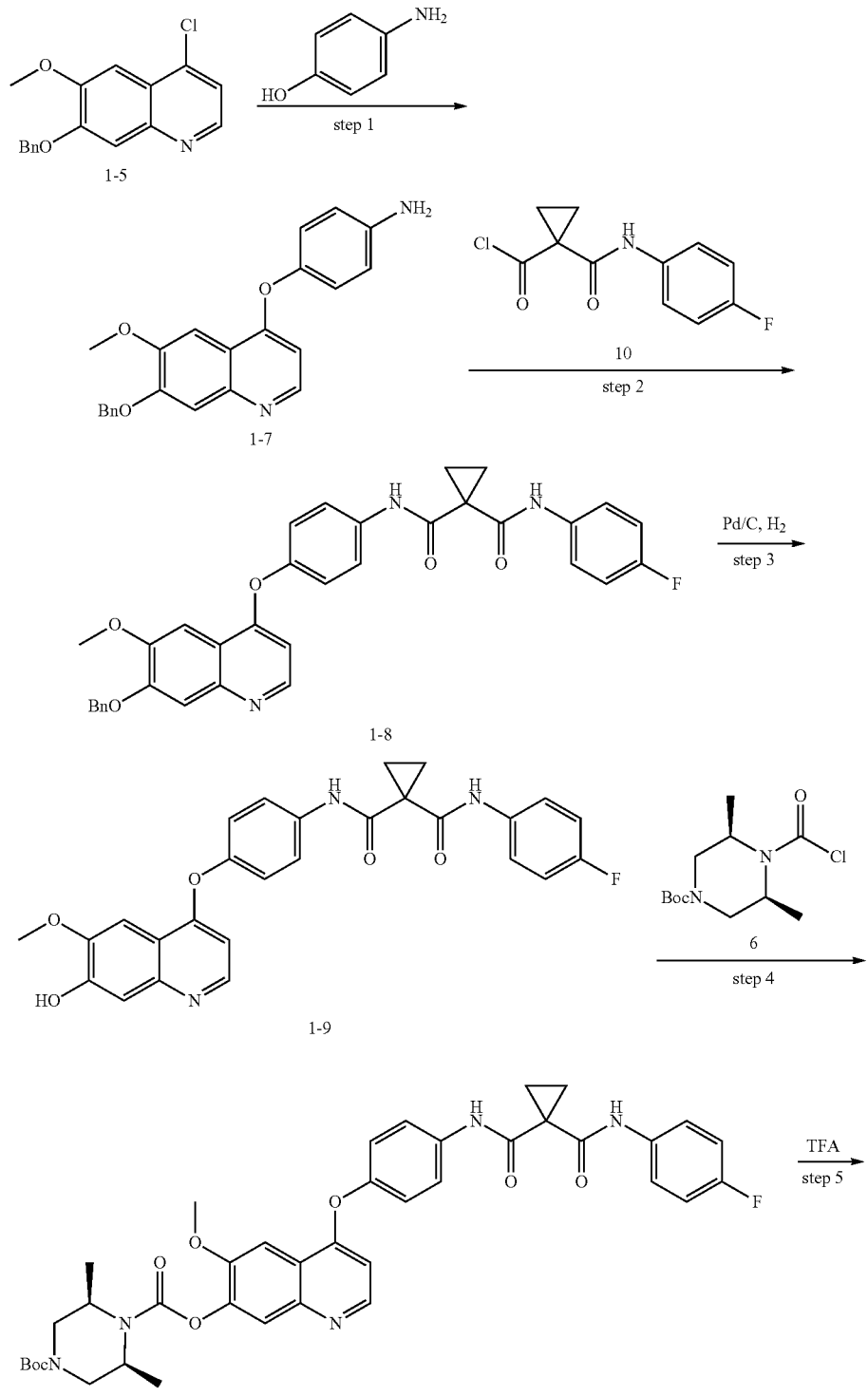
Scheme 6

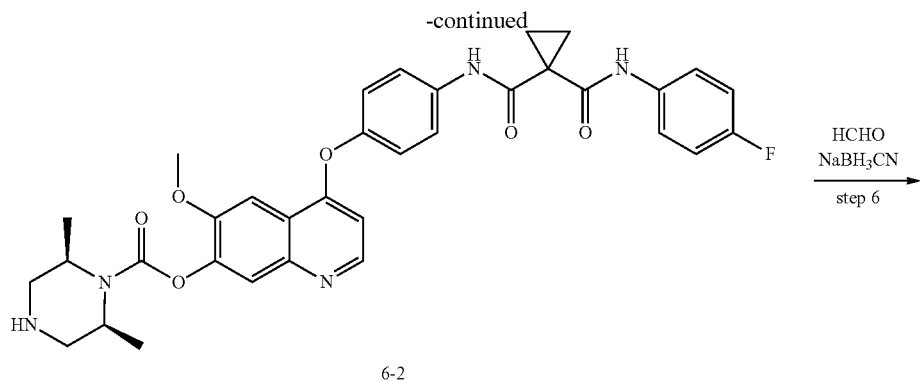

6-2

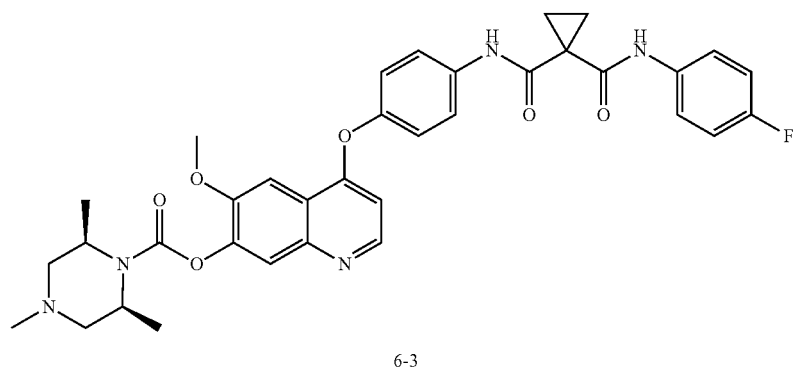 [SMILES: COc1cc2c(Oc3ccc(NC(=O)C4(C(=O)Nc5ccc(F)cc5)CC4)cc3)ccnc2cc1OC(=O)N1CCN(C)C[C@H]1C]

6-3

Step 1:

To a stirred solution of 10.0 g (33.4 mmol) of 7-(benzyloxy)-4-chloro-6-methoxyquinoline (compound 1-5) and 7.0 g (63.7 mmol) of sodium 2-methylbutan-2-olate in 110 mL of N,N-dimethylacetamide was added 7.0 g (64.1 mmol) of 4-aminophenol at RT. The mixture was stirred at 100° C. overnight under nitrogen atmosphere. It was cooled to RT and diluted with 330 mL of water. The mixture was filtered; the filter cake was washed with water (3×150 mL) and dried under reduced pressure to afford compound 1-7. LC-MS: m/e=373 [M+H]$^+$.

Step 2 & 3:

These two steps have been described in Method 1, step 8 and 9.

Step 4:

To a stirred solution of 120 mg (0.44 mmol) of tert-butyl (3R,5S)-4-(carboxy)-3,5-dimethylpiperazine-1-carboxylate in 6 mL of pyridine was added 106 mg (0.22 mmol) of compound 1-6. The mixture was stirred at 60° C. for 2 h and cooled to RT. The reaction was quenched by addition of 10 mL of water. It was extracted with three 30 mL portions of ethyl acetate; the combined organic extracts were washed with brine and dried over anhydrous Na$_2$SO$_4$. After filtration, the filtrate was concentrated under vacuum to give a residue, which was purified by Prep-TLC (EtOAc) to afford compound 6-1. LC-MS: m/e=728 [M+H]$^+$.

Step 5:

To a stirred solution of 50 mg (0.07 mmol) of compound 6-1 in 9 mL of DCM was added 1.8 mL of TFA. The mixture was stirred at RT for 2 h and concentrated. The mixture was basified to pH 7 with saturated aqueous NaHCO$_3$ and extracted with three 35 mL portions of ethyl acetate. The combined organic extracts were washed with brine and dried over anhydrous Na$_2$SO$_4$. After filtration, the filtrate was concentrated to afford a residue, which was purified by Prep-HPLC (XBridge Prep OBD C18 Column, 30*150 mm 5 mm; mobile phase, Water (10 mM NH$_4$HCO$_3$) and ACN (32% Phase B up to 52% in 8 min); Detector, 254 nm UV) to give compound 6-2. LC-MS: m/e=628 [M+H]$^+$.

Step 6:

To a stirred solution of 40 mg (0.06 mmol) of compound 6-2 in 10 mL of MeOH was added 2 mL of HCHO followed by 20 mg (0.32 mmol) of added 2 mL of aqueous HCHO followed by 20.0 mg (0.32 mmol) of NaBH$_3$CN at 0° C. The mixture was stirred at 0° C. for 1 h and quenched by addition of 10 mL of water. It was extracted with three 35 mL portions of ethyl acetate; the combined organic extracts were washed with brine and dried over anhydrous Na$_2$SO$_4$. After filtration, the filtrate was concentrated to afford a residue, which was purified by Prep-HPLC (XBridge Prep OBD C18 Column, 30*150 mm 5 mm; mobile phase, Water (10 mM NH$_4$HCO) and ACN (45% Phase B up to 60% in 8 min); Detector, 254 nm UV) to give compound 6-3. LC-MS: m/e=642 [M+H]$^+$.

Other analogs shown in Table 5 were prepared from compound 1-9 similarly.

TABLE 5

Synthesis of heterocyclic analogs

| Carbonyl Chloride | Structure | LCMS [M + 1]+ |
|---|---|---|
| 5 | 6-4 | 614 |
| | 1-11 | 628 |
| 7 | 6-5 | 628 |
| | 6-6 | 642 |

TABLE 5-continued
Synthesis of heterocyclic analogs
| Carbonyl Chloride | Structure | LCMS [M + 1]+ |
|---|---|---|
| 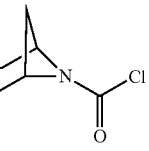<br>8 | 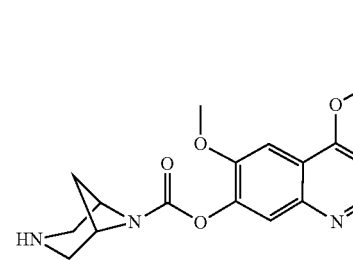<br>6-7 | 612 |
| | 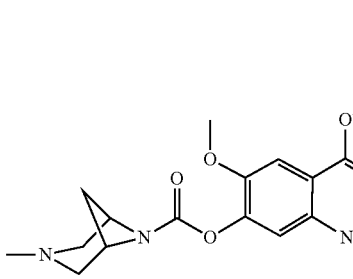<br>6-8 | 626 |
| 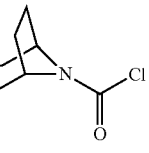<br>9 | 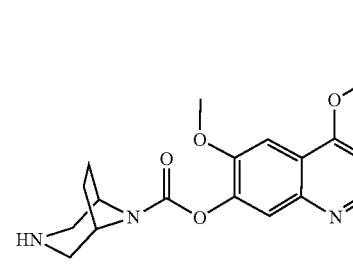<br>6-9 | 626 |
| | 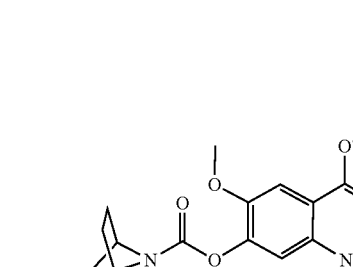<br>6-10 | 640 |

Method 7:
Example 7: Synthesis of 4-(4-(1-((-fluorophenyl)carbamoyl)cyclopropane-1-carboxamido)phenoxy)-7-methoxyquinolin-6-yl (R)-2,4-dimethylpiperazine-1-carboxylate
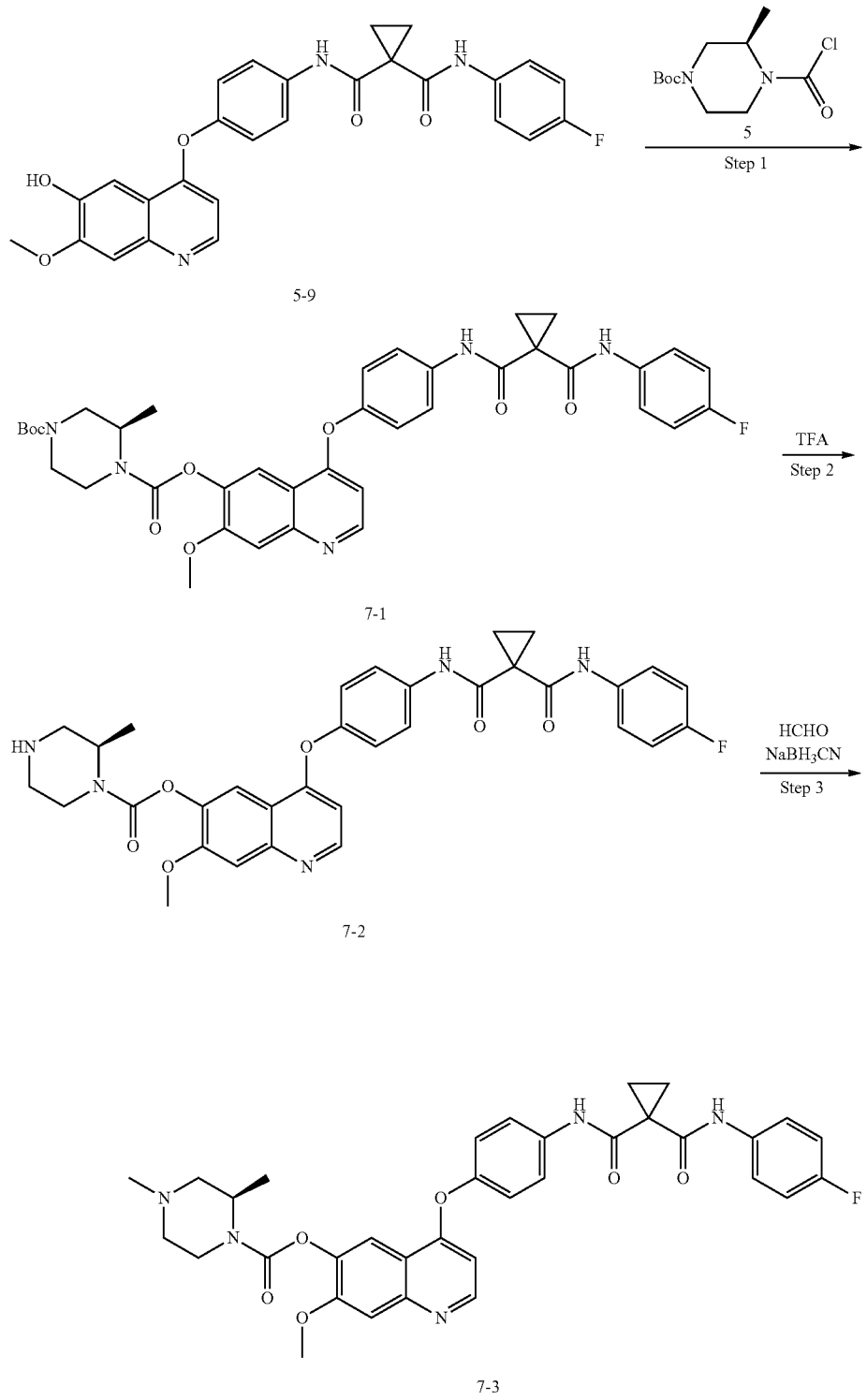

Step 1:
Following the procedure described in Method 6, step 4, compound 5-9 was converted to compound 7-1. LC-MS: m/e=714 [M+H]+.

Step 2:
Following the procedure described in Method 6, step 5, compound 7-1 was converted to compound 7-2. LC-MS: m/e=614 [M+H]+.

Step 3:
Following the procedure described in Method 6, step 6, compound 7-2 was converted to compound 7-3. LC-MS: m/e=628 [M+H]+.

Other analogs shown in Table 6 were prepared from compound 5-9 similarly.

TABLE 6

Synthesis of heterocyclic analogs

| Intermediate | Structure | LCMS [M + 1]+ |
|---|---|---|
| 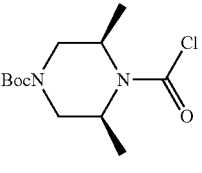 6 | 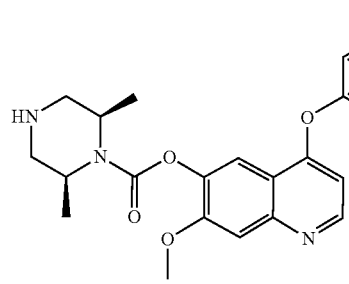 7-4 | 628 |
|  | 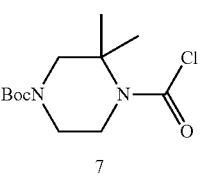 7-5 | 642 |
| 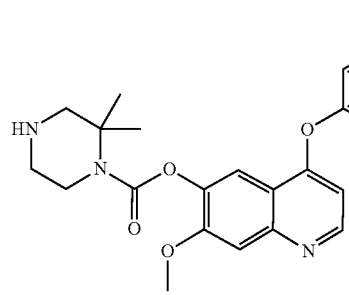 7 | 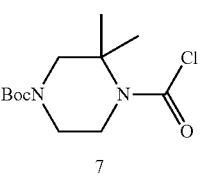 7-6 | 628 |

TABLE 6-continued
Synthesis of heterocyclic analogs
| Intermediate | Structure | LCMS [M + 1]+ |
|---|---|---|
| 7-7 | 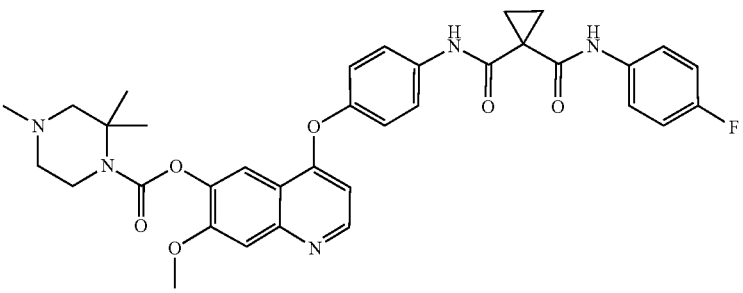 | 642 |
Method 8:
Example 8: Synthesis of 4-(4-(1-((4-fluorophenyl)carbamoyl)cyclopropane-1-carboxamido)phenoxy)-6-methoxyquinazolin-7-yl (R)-2,4-methylpiperazine-1-carboxylate
Scheme 8
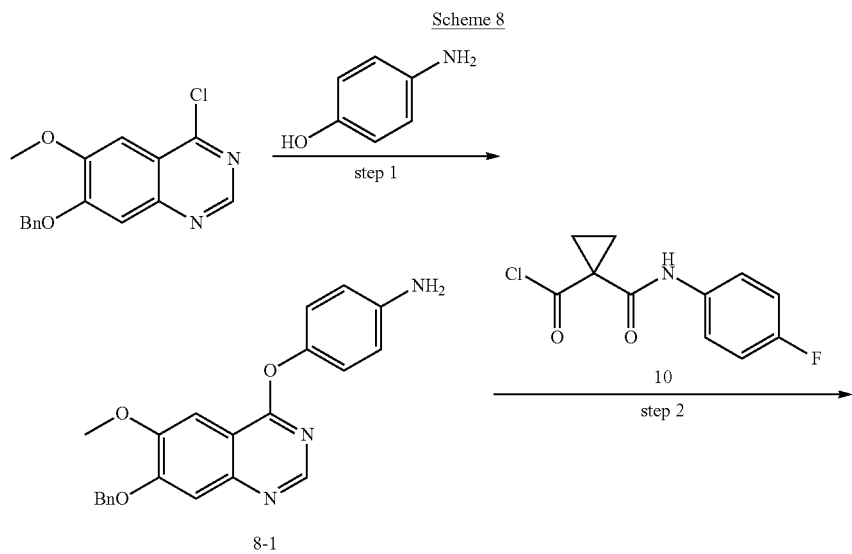
8-1
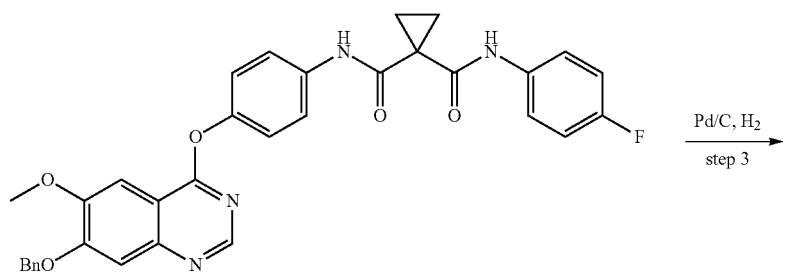
8-2

-continued
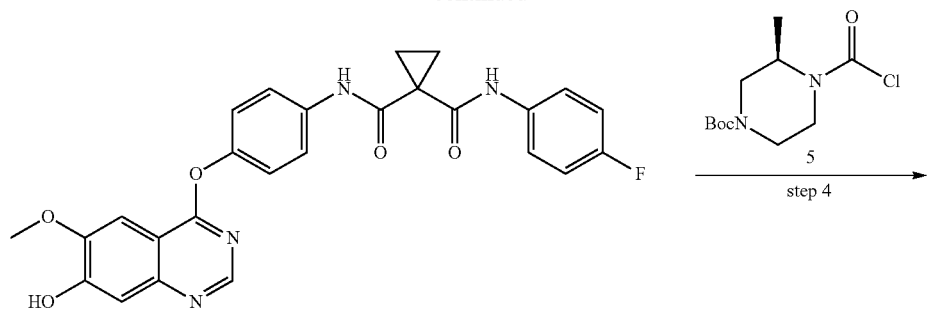
8-3
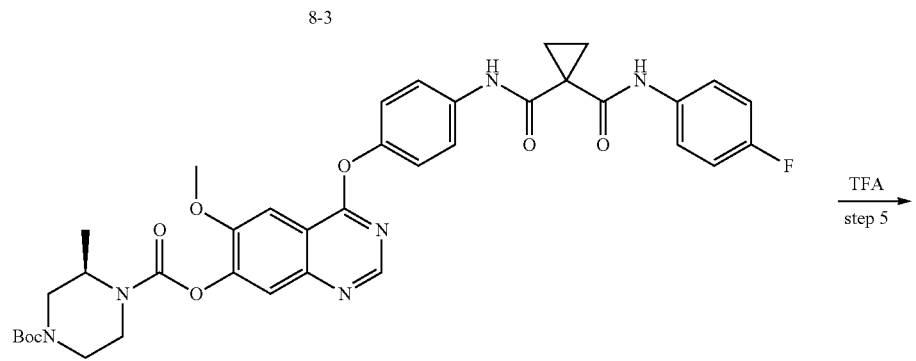
8-4
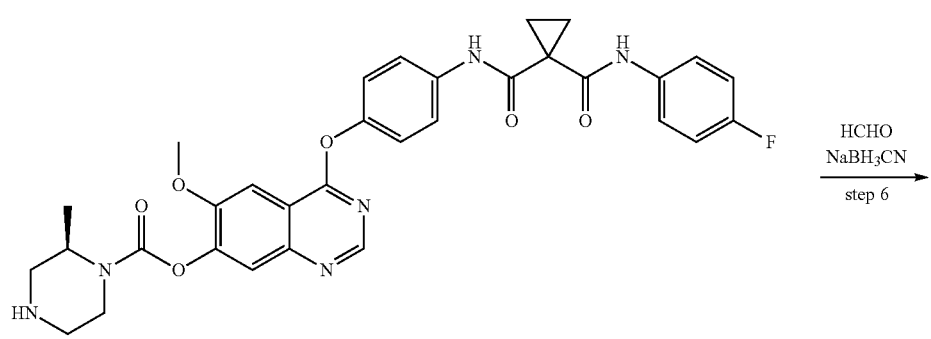
8-5
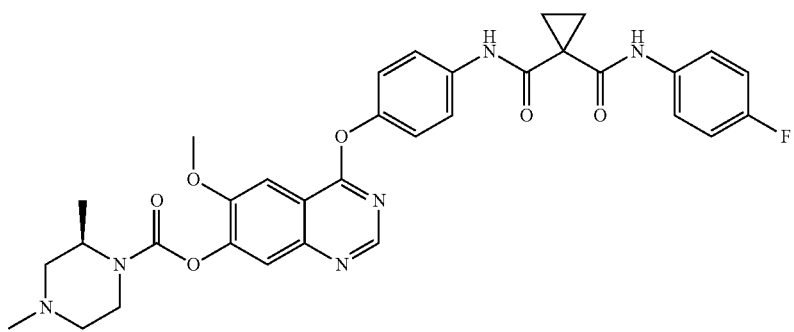
8-6

Step 1:
Following the procedure described in Method 6, step 1, compound 8-1 was prepared from 7-(benzyloxy)-4-chloro-6-methoxyquinazoline. LC-MS: m/e=374 [M+H]$^+$.

Step 2:
Following the procedure described in Method 1, step 8, compound 8-2 was prepared from compound 8-1. LC-MS: m/e=579 [M+H]$^+$.

Step 3:
Following the procedure described in Method 1, step 9, compound 8-3 was prepared from compound 8-2. LC-MS: m/e=489 [M+H]$^+$.

Step 4:
Following the procedure described in Method 6, step 4, compound 8-4 was prepared from compound 8-3. LC-MS: m/e=715 [M+H]$^+$.

Step 5:
Following the procedure described in Method 6, step 5, compound 8-5 was prepared from compound 8-4. LC-MS: m/e=615 [M+H]$^+$.

Step 6:
Following the procedure described in Method 6, step 6, compound 8-6 was prepared from compound 8-5. LC-MS: m/e=629 [M+H]$^+$.

Method 9:

Example 9: Synthesis of 4-(2-fluoro-4-(1-((4-fluorophenyl)carbamoyl)cyclopropane-1-carboxamido)phenoxy)-6-methoxyquinazolin-7-yl (R)-2,4-methylpiperazine-1-carboxylate

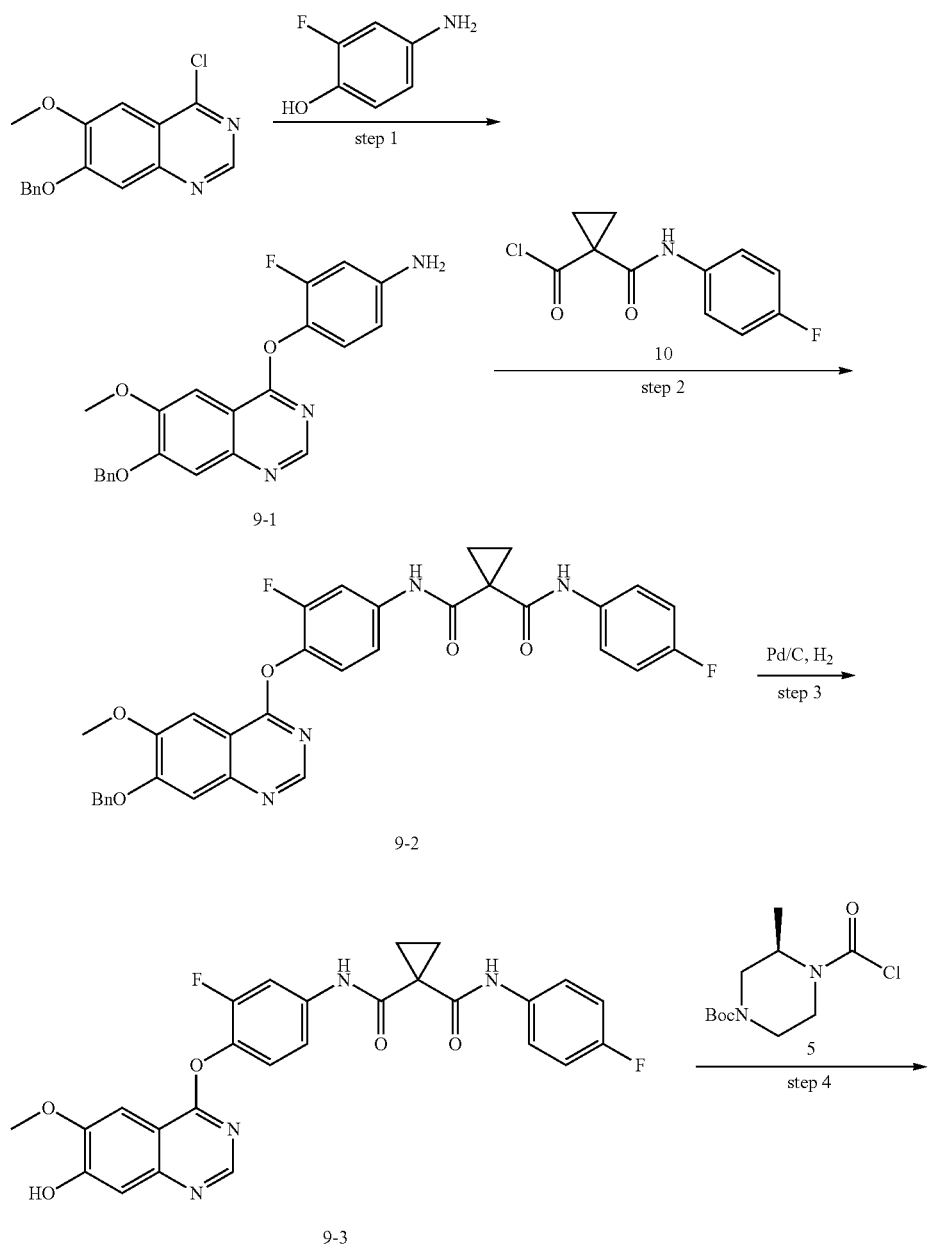

Scheme 9

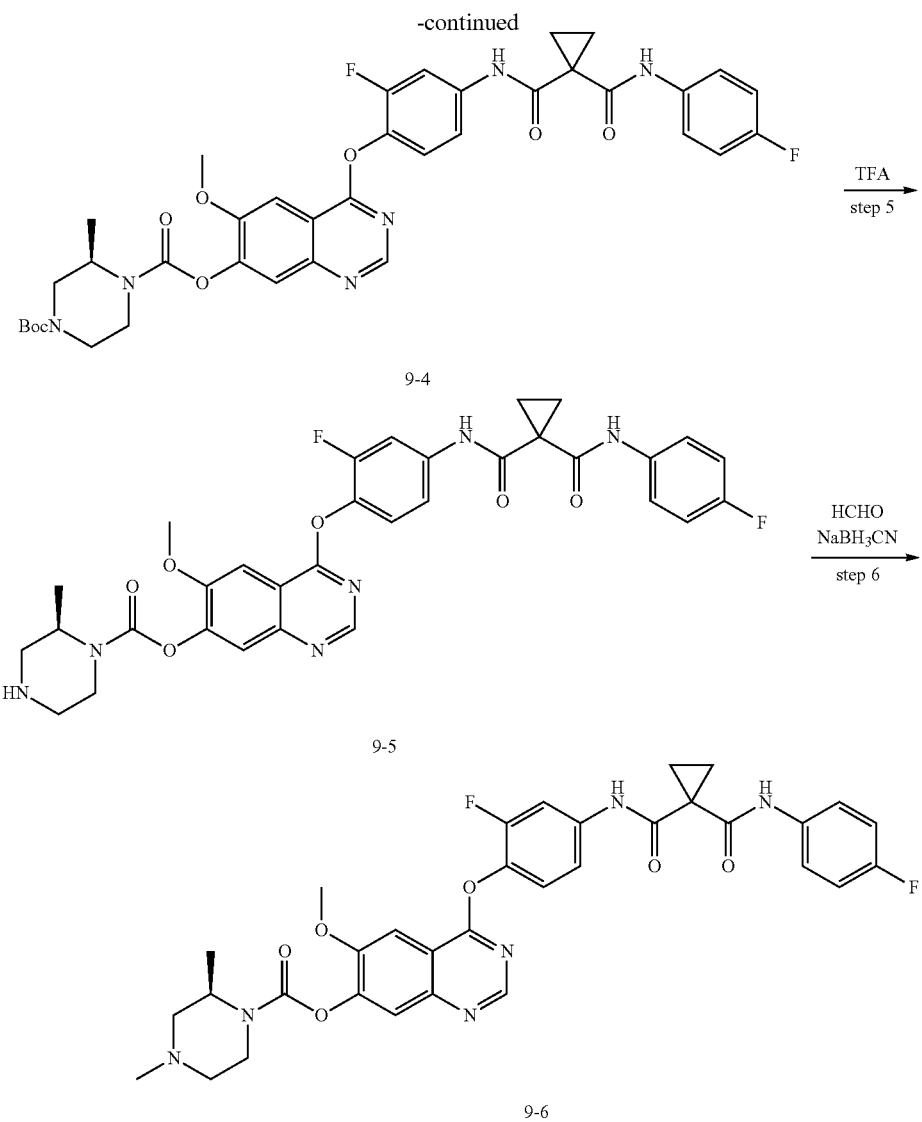

Step 1:
Following the procedure described in Method 6, step 1, compound 9-1 was prepared from 7-(benzyloxy)-4-chloro-6-methoxyquinazoline. LC-MS: m/e=392 [M+H]⁺.

Step 2:
Following the procedure described in Method 1, step 8, compound 9-2 was prepared from compound 9-1. LC-MS: m/e=597 [M+H]⁺.

Step 3:
Following the procedure described in Method 1, step 9, compound 9-3 was prepared from compound 9-2. LC-MS: m/e=507 [M+H]⁺.

Step 4:
Following the procedure described in Method 6, step 4, compound 9-4 was prepared from compound 9-3. LC-MS: m/e=733 [M+H]⁺.

Step 5:
Following the procedure described in Method 6, step 5, compound 9-5 was prepared from compound 9-4. LC-MS: m/e=633 [M+H]⁺.

Step 6:
Following the procedure described in Method 6, step 6, compound 9-6 was prepared from compound 9-5. LC-MS: m/e=647 [M+H]⁺.

Method 10:

Example 10: Synthesis of N-(4-fluorophenyl)-N-(4-((6-methoxy-7-(2-oxoimidazolidin-1-yl)quinoline-4-yl)oxy)phenyl)cyclopropane-1,1-dicarboxamide

101

-continued

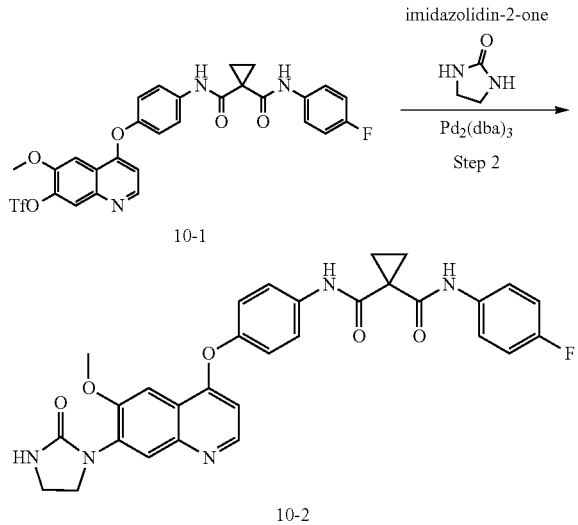

Step 1:
To a stirred solution of 150 mg (0.31 mmol) of compound 1-8 and 73 mg (0.92 mmol) of pyridine in 35 mL of DCM was added 130 mg (0.46 mmol) of Tf$_2$O dropwise at 0° C. The mixture was stirred at 0° C. for 1 h and at RT for additional 1 h. The reaction was quenched with 20 mL of water and extracted with three 30 mL portions of DCM. The combined organic extracts were washed with brine and dried over anhydrous Na$_2$SO$_4$. It was filtered and the filtrate was concentrated. The residue was purified by Prep-TLC (10% MeOH in DCM) to afford compound 10-1. LC-MS: m/e=620 [M+H]$^+$.

Step 2:
To a stirred solution of 120 mg (0.19 mmol) of compound 10-1 and 34 mg (0.39 mmol) of imidazoline-2-one in 4 mL of toluene was added 252 mg (0.77 mmol) of Cs$_2$CO$_3$, 18 mg (0.02 mmol) of Pd$_2$(dba)$_3$ and 22 mg (0.04 mmol) of xantphos in portions at RT under nitrogen atmosphere. The mixture was stirred at 100° C. for 1 h under nitrogen atmosphere. The reaction was cooled to RT and quenched by the addition of 10 mL of water. It was extracted with three 20 mL portions of EtOAc; the combined organic layers were washed with brine and dried over anhydrous Na$_2$SO$_4$. It was filtered and the filtrate was concentrated. The residue was purified by Prep-TLC (10% MeOH in DCM) to afford a residue, which was purified by Prep-HPLC (XBridge Prep OBD C18 Column 30*150 mm 5 m; Mobile Phase A: Water (10 mmol/L NH$_4$HCO), Mobile Phase B: ACN; (Gradient: 33% B to 50% B in 8 min); Flow rate: 60 mL/min; Rt: 7.83 min, Detector, 254 nm UV.) to afford compound 10-2. LC-MS: m/e=556 [M+H]$^+$.

Synthesis of Intermediates
1. Synthesis of Intermediate 1:

Scheme 11

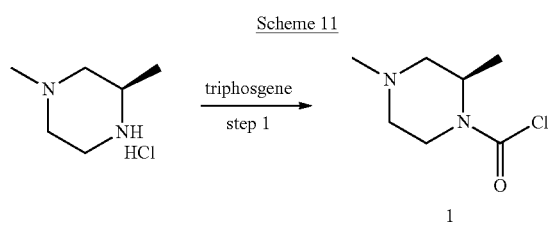

102

Step 1: Synthesis of (R)-2,4-dimethylpiperazine-1-carbonyl chloride

To a stirred solution of 0.39 g (1.33 mmol) of triphosgene in 5 mL of DCM was added 0.32 g (3.98 mmol) of pyridine dropwise at 0° C. In a second flask, to a stirred mixture of 0.20 g (1.33 mmol) of (3R)-1,3-dimethylpiperazine hydrochloride in 4 mL of DCM was added 0.32 g (3.98 mmol) of pyridine at room temperature. The mixture was stirred for 10 min at room temperature and added to the first flask. The whole mixture was stirred at rt for additional 2 h and concentrated under vacuum to obtain intermediate 1, which was used in the next step without further purification.

Following the above procedure, Intermediates shown in Table 7 were prepared similarly.

TABLE 7

Synthesis of intermediates 2-4.
Intermediate Structure

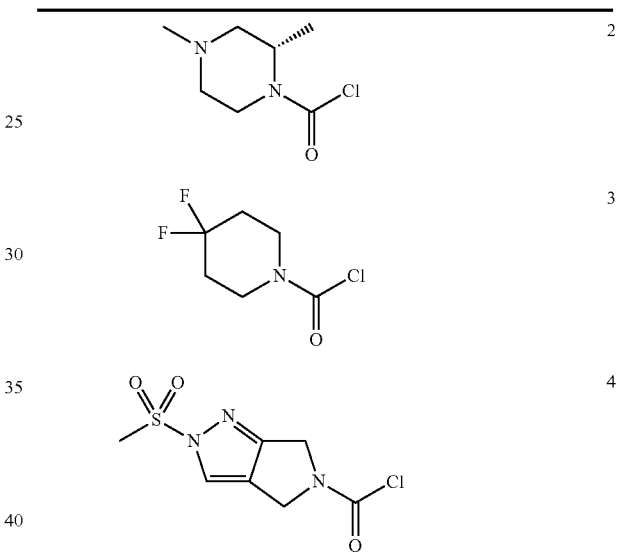

2. Synthesis of Intermediate 5:

Scheme 12

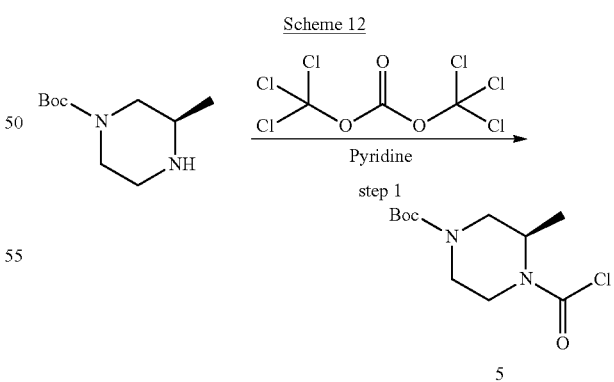

To a stirred solution of 26.7 g (89.9 mmol) of ditrichloromethyl carbonate in 500 mL of DCM was added 21.6 mL (273 mmol) of pyridine at 0° C. After 10 min, a solution of 18.0 g (89.9 mmol) of tert-butyl (3R)-3-methylpiperazine-1-carboxylate in DCM was added dropwise at 0° C. The mixture was stirred at 0° C. for 20 min and at RT overnight.

It was concentrated under reduced pressure to afford compound 5 without further purification.

The following intermediates in Table 8 were prepared similarly from the corresponding amines.

TABLE 8

Synthesis of intermediates 6-9
Intermediate Structure

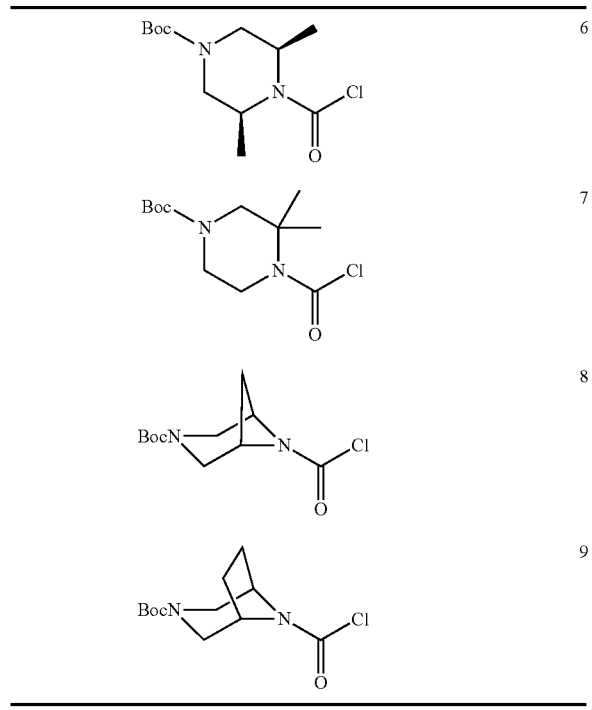

3. Synthesis of Intermediate 10:

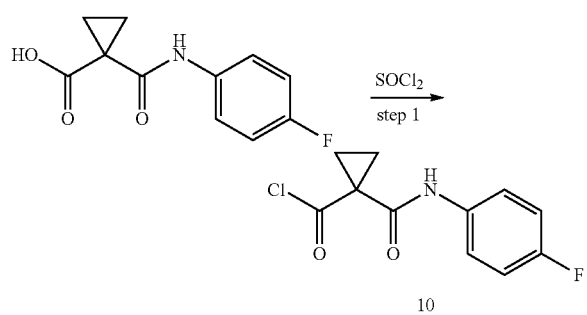

Step 1:

To a stirred solution of 80 mL sulfuryl dichloride was added 5.0 g (22.4 mmol) of 1-[(4-fluorophenyl)carbamoyl]cyclopropane-1-carboxylic acid in several portions at 0° C. The reaction mixture was stirred at RT overnight and concentrated under vacuum; the residue was co-evaporated with 10 mL of DCM and 10 mL of toluene to intermediate 10, which was used in the next step directly without further purification.

LC-MS Conditions Used in the Experimental Procedures Described Above:

Condition A: Shimadzu LC20ADXR/LCMS2020, Column: Kinextex XB-C18 (50*3.0 mm) 2.6 μm; Mobile phase: A: 0.1% Formic acid in Water, B: 0.1% Formic acid in Acetonitrile; Gradient: 90:10 to 0:100 (A:B) over 1.1 min, 0:100 (A:B) for 0.50 min, Flow Rate: 1.5 ml/min. UV detection: 190-400 nm.

Condition B: Shimadzu LC20AD/LCMS2020; Column: Shim-pack XR-ODS (50*3.0 mm) 2.2 μm; Mobile phase: A: 0.05% Trifluoroacetic acid in Water, B: 0.05% Trifluoroacetic acid in Acetonitrile; Gradient: 95:5 to 0:100 (A:B) over 1.1 min, 0:100 (A:B) for 0.55 min, Flow Rate: 1.2 ml/min; UV detection: 190-400 nm.

Condition C: Shimadzu LC30AD/LCMS2020, Column: Ascentis Express (50*3.0 mm) 2.7 μm; Mobile phase: A: 0.05% Trifluoroacetic acid in Water, B: 0.05% Trifluoroacetic acid in Acetonitrile; Gradient: 95:5 to 0:100 (A:B) over 1.2 min, 0:100 (A:B) for 0.50 min, Flow Rate: 1.5 ml/min. UV detection: 190-400 nm.

Condition D: Shimadzu LC20ADXR/LCMS2020, Column: Kinextex XB-C18 (50*3.0 mm) 2.6 μm; Mobile phase: A: 0.1% Formic acid in Water, B: 0.1% Formic acid in Acetonitrile; Gradient: 90:10 to 0:100 (A:B) over 1.1 min, 0:100 (A:B) for 0.50 min, Flow Rate: 1.5 ml/min. UV detection: 190-400 nm.

Condition E: Shimadzu LC20AD/LCMS2020; Column: Shim-pack XR-ODS (50*3.0 mm) 2.2 μm; Mobile phase: A: 0.05% Trifluoroacetic acid in Water, B: 0.05% Trifluoroacetic acid in Acetonitrile; Gradient: 95:5 to 0:100 (A:B) over 1.1 min, 0:100 (A:B) for 0.55 min, Flow Rate: 1.2 ml/min; UV detection: 190-400 nm.

Condition F: Shimadzu LC20ADXR/LCMS2020, Column: Poroshell HPH-C18 (50*3.0 mm) 2.7 μm; Mobile phase: A: 5 mmol/L Ammonium Bicarbonate in Water, B: Acetonitrile; Gradient: 90:10 to 5:95(A:B) over 2.1 min, 5:95(A:B) for 0.6 min, Flow Rate: 1.2 mL/min. UV detection: 190-400 nm.

Condition G: Shimadzu LC20ADXR/LCMS2020, Column: Poroshell HPH-C18 (50*3.0 mm) 2.7 μm; Mobile phase: A: 5 mmol/L Ammonium Bicarbonate in Water, B: Acetonitrile; Gradient: 90:10 to 5:95(A:B) over 2.1 min, 5:95(A:B) for 0.60 min; Flow Rate: 1.2 mL/min. UV detection: 190-400 nm.

Condition H: Shimadzu LC20ADXR/LCMS2020, Column: Kinextex EVO C18 (50*3.0 mm) 2.6 μm; Mobile phase: A: 5 mmol/L Ammonium Bicarbonate in Water, B: Acetonitrile; Gradient: 90:10 to 5:95(A:B) over 2.1 min, 5:95(A:B) for 0.6 min, Flow Rate: 1.2 mL/min. UV detection: 190-400 nm.

Condition I: Shimadzu LC20AD/LCMS2020; Column: Shim-pack XR-ODS (50*3.0 mm) 2.2 μm; Mobile phase: A: 0.05% Trifluoroacetic acid in Water, B: 0.05% Trifluoroacetic acid in Acetonitrile; Gradient: 95:5 to 0:100(A:B) over 2 min, 0:100 (A:B) for 0.7 min, Flow Rate: 1.2 mL/min; UV detection: 190-400 nm.

Condition J: Shimadzu LC20AD/LCMS2020, Column: Shim-pack XR-ODS (3.0*50 mm) 2.2 μm; Mobile phase: A: 0.05% Trifluoroacetic acid in water, B: 0.05% Trifluoroacetic in Acetonitrile; Gradient: 95:5 to 0:100 (A:B) over 2.0 min, 0:100 (A:B) for 0.70 min; Flow Rate: 1.2 mL/min. UV detection: 190-400 nm.

Condition K: Shimadzu LC20ADXR/LCMS2020, Column: Poroshell HPH-C18 (50*3.0 mm) 2.7 μm; Mobile phase: A: 5 mmol/L Ammonium Bicarbonate in Water, B: Acetonitrile; Gradient: 90:10 to 5:95 (A:B) over 2.1 min, 5:95(A:B) for 0.6 min, Flow Rate: 1.2 mL/min. UV detection: 190-400 nm.

Condition L: Shimadzu LC20ADXR/LCMS2020, Column: Poroshell HPH-C18 (50*3.0 mm) 2.7 μm; Mobile phase: A: 5 mmol/L Ammonium Bicarbonate in Water, B:

Acetonitrile; Gradient: 90:10 to 5:95 (A:B) over 2.1 min, 5:95(A:B) for 0.60 min, Flow Rate: 1.2 mL/min. UV detection: 190-400 nm.

Condition M: Shimadzu LC20ADXR/LCMS2020, Column: Kinextex EVO C18 (50*3.0 mm) 2.6 μm; Mobile phase: A: 5 mmol/L Ammonium Bicarbonate in Water, B: Acetonitrile; Gradient: 90:10 to 5:95 (A:B) over 2.1 min, 5:95(A:B) for 0.6 min, Flow Rate: 1.2 mL/min. UV detection: 190-400 nm.

Condition N: Shimadzu LC20ADXR/LCMS2020, Column: Kinextex EVO C18 (50*3.0 mm) 2.6 μm; Mobile phase: A: 0.04% NH$_4$OH B: Acetonitrile; Gradient: 90:10 to 5:95 (A:B) over 2.1 min, 5:95 (A:B) for 0.60 min, Flow Rate: 1.2 ml/min. UV detection: 190-400 nm.

Condition O: Shimadzu LC20ADXR/LCMS2020, Column: Kinextex EVO C18 (50*3.0 mm) 2.6 μm; Mobile phase: A: 0.04% NH$_4$OH in Water, B: Acetonitrile; Gradient: 90:10 to 5:95 (A:B) over 2.1 min, 5:95 (A:B) for 0.6 min, Flow Rate: 1.2 mL/min. UV detection: 190-400 nm.

Condition P: Shimadzu LC20ADXR/LCMS2020, Column: Poroshell HPH-C18 (50*3.0 mm) 2.7 μm; Mobile phase: A: 5 mmol/L Ammonium Bicarbonate in Water, B: Acetonitrile; Gradient: 90:10 to 5:95 (A:B) over 2.1 min, 5:95(A:B) for 0.60 min, Flow Rate: 1.2 mL/min. UV detection: 190-400 nm.

Condition Q: Shimadzu LC20ADXR/LCMS202, Column: Kinetex EVO C18, 3.0*50 mm, 2.6 μm; Mobile Phase A: 0.04% NH$_4$OH in water, B: Acetonitrile; Flow rate: 1.2 mL/min; Gradient: 90:10 to 5:95 (A:B) over 2.1 min, 5:95(A:B) for 0.6 min, Flow Rate: 1.2 mL/min. UV detection: 190-400 nm.

Condition R: Shimadzu LC20ADXR/LCMS2020, Column: Poroshell HPH-C18 (50*3.0 mm) 2.7 μm; Mobile phase: A: 5 mmol/L Ammonium Bicarbonate in Water, B: Acetonitrile; Gradient: 90:10 to 5:95 (A:B) over 2.1 min, 5:95(A:B) for 0.60 min; Flow Rate: 1.2 mL/min. UV detection: 190-400 nm.

ASSAYS

Protocols that may be used to determine the recited potency for the compounds of the disclosure are describe below.

HotSpot Kinase Assay

HotSpot assay platform (Reaction Biology) was used to measure kinase/inhibitor interactions as described previously (Anastassiadis et al., 2011). Table 7 listed the experimental details for each protein kinase. Specifically, for each reaction, kinase and substrate were mixed in a pH 7.5 buffer containing 20 mM HEPES, 10 mM MgCl$_2$, 1 mM EGTA [Ethylene glycol-bis(2-aminoethylether)-N,N,N',N'-tetraacetic acid], 0.02% Brij35, 0.02 mg/mL BSA (Bovine Serum Albumin), 0.1 mM Na$_3$VO$_4$, 2 mM DTT, and 1% DMSO. Compounds were then added to each reaction mixture. After a 20-min incubation, ATP (Sigma-Aldrich) and [γ-$^{33}$P] ATP (PerkinElmer) were added at a final total concentration of 100 μM. Reactions were carried out at room temperature for 2 hours and spotted onto P81 ion exchange cellulose chromatography paper (Whatman). Filter paper was washed in 0.75% phosphoric acid to remove unincorporated ATP. The percent remaining kinase activity relative to a vehicle-containing (DMSO) kinase reaction was calculated for each kinase/inhibitor pair. Outliers were identified and removed as described previously (Anastassiadis et al., 2011). IC$_{50}$ values were calculated using Prism 5 (GraphPad). The testing results for selected compounds are summarized in Table 9 and Table 10, wherein A represents the IC$_{50}$ value of <100 nM; B represents the IC$_{50}$ value of 100-1000 nM; and C represents the IC$_{50}$ value of >1000 nM.

TABLE 9

Multikinase Inhibitory Activity of Representative Examples

| Compd | AXL | c-Kit | c-MER | c-MET | DDR1 | EPHA2 | FMS | KDR/VEGFR2 | LOK/STK10 | TYRO3/SKY |
|---|---|---|---|---|---|---|---|---|---|---|
| Ref. 1* | A | B | A | C | A | B | A | B | — | A |
| 1-17 | B | A | A | A | A | B | B | B | B | C |
| 1-13 | B | B | B | A | A | C | C | C | C | C |
| 1-14 | B | B | B | A | A | C | C | C | C | C |
| 1-15 | B | B | B | B | A | C | B | C | B | C |
| 1-11 | A | A | A | A | A | B | A | C | B | B |
| 1-12 | A | A | A | A | A | B | B | B | B | B |
| 2-3 | A | A | A | A | A | B | A | B | B | B |
| 2-2 | A | A | A | A | A | B | A | B | B | B |
| 2-4 | A | A | A | A | A | B | B | C | B | C |
| 2-5 | A | A | A | A | A | B | B | C | B | C |
| 2-6 | A | A | A | A | A | A | A | B | B | B |
| 2-7 | A | A | A | A | A | A | A | B | B | B |
| 1-16 | B | B | B | A | A | C | C | C | C | C |
| 3-5 | A | A | A | A | A | A | B | A | B | B |
| 3-6 | A | B | A | A | A | A | B | B | B | B |
| 5-10 | A | A | A | A | A | A | A | A | B | A |
| 6-4 | A | A | A | A | A | B | A | B | B | B |
| 6-3 | A | A | A | B | A | B | B | B | B | B |
| 6-6 | A | A | A | B | A | B | B | B | B | B |
| 10-2 | A | A | A | A | A | B | A | B | B | B |
| 6-2 | A | A | B | B | A | B | B | B | B | B |
| 7-3 | A | A | A | A | A | B | A | A | B | A |
| 7-2 | A | A | A | A | A | A | A | A | A | A |
| 6-5 | A | A | A | A | A | B | B | C | B | B |
| 7-4 | A | A | A | A | A | B | A | A | B | B |
| 7-5 | A | A | A | A | A | B | A | A | B | B |
| 7-6 | A | A | A | A | A | B | B | A | B | A |
| 7-7 | A | A | A | A | A | B | B | B | C | B |
| 8-6 | B | B | B | B | A | C | B | C | C | B |

TABLE 9-continued

Multikinase Inhibitory Activity of Representative Examples

| Compd | AXL | c-Kit | c-MER | c-MET | DDR1 | EPHA2 | FMS | KDR/VEGFR2 | LOK/STK10 | TYRO3/SKY |
|---|---|---|---|---|---|---|---|---|---|---|
| 8-5 | B | A | B | B | A | C | B | C | C | B |
| 9-5 | A | B | B | A | A | B | B | B | B | B |
| 9-6 | A | B | A | A | A | B | B | B | C | B |

*Ref. 1: Staurosporin, CAS # [62996-74-1].

TABLE 10

Inhibitory Potencies of Compound 1-10 on Multikinases

| Potency* | Protein Kinases |
|---|---|
| A | DDR2, HPK4, DDR1, FLT3, BRK, C-MER, TRKA, C-MET, c-KIT, FMS, AXL, EPHA2 |
| B | RET, EPHB4, MNK2, TYROS, KDR, EPHA3, LOK, EPHB2, FLT1, LCK, EPHA4, EPHB1, FLT4, PDGFβ |
| C | TIE2/TEK, KHS/MAP4K5, BLK, PLK4/SAK, RON/MST1R, EPHA1, FRK/PTK5, MEK1, CDK7/cyclin H, MEK5, SLK/STK2 |

*Note:
A: <100 nM;
B: 100-1000 nM;
C: >1000 nM

TABLE 11

Experimental Conditions for the Determination of Inhibitory Potencies of Protein Kinases

| Kinase | Vendor | Cat # | Enzyme in reaction (nM) | Substrate | Vendor | Cat # | Substrate in reaction (μM) |
|---|---|---|---|---|---|---|---|
| AXL | BPS | 40180 | 30 | ABLtide | Genscript | 94851-7 | 20 |
| BLK | Invitrogen | PV3683 | 1.25 | pEY (mg/ml) | Sigma | P7244-250MG | 0.2 |
| BRK | Invitrogen | PR4375B | 100 | pEY (mg/ml) | Sigma | P7244-250MG | 0.02 |
| CDK7/cyclin H | Invitrogen | PV4186 | 200 | SC-MBP | SignalChem | M42-51N | 20 |
| c-Kit | Invitrogen | PV3589 | 250 | pEY (mg/ml) + Mn | Sigma | P7244-250MG | 0.2 |
| c-MER | Invitrogen | PR6317A | 2 | pEY (mg/ml) | Sigma | P7244-250MG | 0.2 |
| c-MET | Invitrogen | PV3143 | 16 | MBP | SignalChem | 102641 | 20 |
| DDR1 | Carna Biosciences | Carna 08-113 | 150 | IRS1tide | AnaSpec | 61764 | 20 |
| DDR2 | ProQinase | 0771-0000-1 | 10 | Axltide + Mn | Genscript | 45088-1 | 20 |
| EPHA1 | Invitrogen | PV3841 | 40 | pEY (mg/ml) + Mn | Sigma | P7244-250MG | 0.2 |
| EPHA2 | Invitrogen | PR7040A | 2 | pEY (mg/ml) | Sigma | P7244-250MG | 0.2 |
| EPHA3 | Invitrogen | PV3359 | 15 | pEY (mg/ml) + Mn | Sigma | P7244-250MG | 0.2 |
| EPHA4 | Invitrogen | PV3651 | 2.5 | pEY (mg/ml) + Mn | Sigma | P7244-250MG | 0.2 |
| EPHB1 | Invitrogen | PR6311B | 1 | pEY (mg/ml) | Sigma | P7244-250MG | 0.2 |
| EPHB2 | Invitrogen | PV3625 | 0.2 | pEY (mg/ml) + Mn | Sigma | P7244-250MG | 0.2 |

TABLE 11-continued

Experimental Conditions for the Determination of Inhibitory Potencies of Protein Kinases

| Kinase | Vendor | Cat # | Enzyme in reaction (nM) | Substrate | Vendor | Cat # | Substrate in reaction (μM) |
|---|---|---|---|---|---|---|---|
| EPHB4 | Invitrogen | PR4688B | 1 | pEY (mg/ml) | Sigma | P7244-250MG | 0.2 |
| FLT1/ VEGFR1 | Invitrogen | PV3666 | 15 | pEY (mg/ml) + Mn | Sigma | P7244-250MG | 0.2 |
| FLT3 | Invitrogen | PV3182 | 15 | ABLtide | Genscript | 94851-7 | 20 |
| FLT4/ VEGFR3 | Invitrogen | PV4129 | 1.5 | pEY (mg/ml) + Mn | Sigma | P7244-250MG | 0.2 |
| FMS | Invitrogen | PV3249 | 15 | pEY (mg/ml) + Mn | Sigma | P7244-250MG | 20 |
| FRK/ PTK5 | Invitrogen | PR7729A | 2 | pEY (mg/ml) + Mn | Sigma | P7244-250MG | 0.2 |
| HIPK4 | Invitrogen | PV3852 | 0.6 | MBP | Signal-Chem | 102641 | 20 |
| KDR/ VEGFR2 | Invitrogen | PR5992C | 1 | pEY (mg/ml) + Mn | Sigma | P7244-250MG | 0.2 |
| KHS/ MAP4K5 | Invitrogen | PR6671A | 0.6 | MBP | Signal-Chem | 102641 | 20 |
| LCK | Invitrogen | P3043 | 8 | pEY (mg/ml) + Mn | Sigma | P7244-250MG | 0.2 |
| LOK/ STK10 | Signal-Chem | S29-11G | 10 | LRRKtide | Signal-Chem | L10-58 | 20 |
| MEK1 | Invitrogen | PV3303 | 100 | ERK2 (K52R) | RBC | RBC-ERK2 (K52R) | 5 |
| MEK5 | Signal-Chem | M06-10G | 30 | ERK5 (K84R) | RBC | SUB-11-449 | 5 |
| MNK2 | Invitrogen | PR8046A | 50 | MBP | Signal-Chem | 102641 | 20 |
| PDGFRb | Invitrogen | P3082 | 15 | pEY (mg/ml) + Mn | Sigma | P7244-250MG | 0.2 |
| PLK4/ SAK | ProQinase | 0306-0000-1 | 160 | Casein | Signal-Chem | C03-54BN | 20 |
| RET | Invitrogen | PV3819 | 3 | CHKtide | Biomer Technology | 131018-1-RBC | 20 |
| RON/ MST1R | Invitrogen | PR7906A | 9 | Axltide + Mn | Genscript | 45088-1 | 20 |
| SLK/STK2 | Invitrogen | PR7465A | 50 | Histone H3.3 | RBC | HMT-11-134 | 20 |
| TIE2/ TEK | Invitrogen | PV3628 | 2.25 | pEY (mg/ml) + Mn | Sigma | P7244-250MG | 0.2 |
| TRKA | Invitrogen | PV3144 | 15 | pEY (mg/ml) + Mn | Sigma | P7244-250MG | 0.2 |
| TRKA (G595R) | Signal-Chem | N16-12CG | 80 | pEY (mg/ml) + Mn | Sigma | P7244-250MG | 0.2 |
| TRKA (G6670) | Signal-Chem | N16-12BG | 20 | pEY (mg/ml) + Mn | Sigma | P7244-250MG | 0.2 |
| TYRO3/ SKY | Invitrogen | PV3828 | 0.2 | pEY (mg/ml) + Mn | Sigma | P7244-250MG | 0.2 |

Unless otherwise indicated, all numbers expressing quantities of ingredients, properties such as molecular weight, reaction conditions, and etc. used in herein are to be understood as being modified in all instances by the term "about." Each numerical parameter should at least be construed in light of the number of reported significant digits and by applying ordinary rounding techniques. Accordingly, unless indicated to the contrary, the numerical parameters may be modified according to the desired properties sought to be achieved, and should, therefore, be considered as part of the disclosure. At the very least, the examples shown herein are for illustration only, not as an attempt to limit the scope of the disclosure.

The terms "a," "an," "the" and similar referents used in the context of describing embodiments of the present disclosure (especially in the context of the following claims) are to be construed to cover both the singular and the plural, unless otherwise indicated herein or clearly contradicted by context. All methods described herein may be performed in any suitable order unless otherwise indicated herein or otherwise clearly contradicted by context. The use of any and all examples, or exemplary language (e.g., "such as") provided herein is intended merely to better illustrate embodiments of the present disclosure and does not pose a limitation on the scope of any claim. No language in the specification should be construed as indicating any non-claimed element essential to the practice of the embodiments of the present disclosure.

Groupings of alternative elements or embodiments disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability.

Certain embodiments are described herein, including the best mode known to the inventors for carrying out the embodiments. Of course, variations on these described embodiments will become apparent to those of ordinary skill in the art upon reading the foregoing description. The inventor expects skilled artisans to employ such variations as appropriate, and the inventors intend for the embodiments of the present disclosure to be practiced otherwise than specifically described herein. Accordingly, the claims include all modifications and equivalents of the subject matter recited in the claims as permitted by applicable law. Moreover, any combination of the above-described elements in all possible variations thereof is contemplated unless otherwise indicated herein or otherwise clearly contradicted by context.

In closing, it is to be understood that the embodiments disclosed herein are illustrative of the principles of the claims. Other modifications that may be employed are within the scope of the claims. Thus, by way of example, but not of limitation, alternative embodiments may be utilized in accordance with the teachings herein. Accordingly, the claims are not limited to embodiments precisely as shown and described.

What is claimed is:

1. A compound represented by a formula:

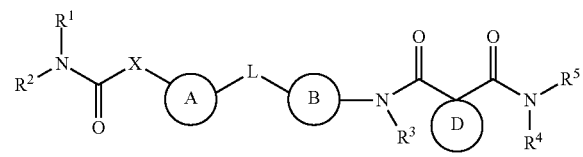

or a pharmaceutically acceptable salt thereof;

wherein Ring A is:

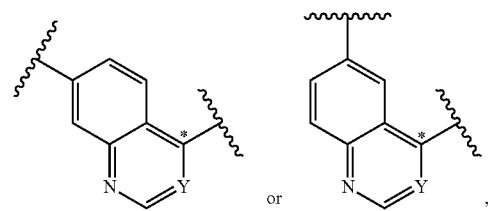

wherein the structure is optionally substituted with 0, 1, 2, 3, 4, or 5 substituents and each substituent is independently F, Cl, Br, I, —$NR^A R^B$, $C_{1-6}$ hydrocarbyl, —OH, —CN, or —O—$C_{1-6}$ alkyl; wherein Y is N or CH; and wherein the asterisk indicates the point of attachment of C atom to L;

Ring B is 6-membered arylene that is optionally substituted with 0, 1, 2, 3, or 4 substituents and each substituent is independently F, Cl, Br, I, —$NR^A R^B$, $C_{1-6}$ hydrocarbyl, —OH, —CN, or —O—$C_{1-6}$ alkyl;

Ring D is 3-membered carbocycle that is optionally substituted with 0, 1, 2, 3, or 4 substituents and each substituent is independently F, Cl, Br, —$NR^A R^B$, $C_{1-6}$ hydrocarbyl, —OH, —CN, or —O—$C_{1-6}$ alkyl;

L is —O—;

X is —O—, or —$N(R^B)$—;

$R^A$ and $R^B$ are independently H or $C_{1-6}$ hydrocarbyl;

$R^3$ and $R^4$ are H;

$R^1$ and $R^2$ are independently H, $C_{1-12}$ alkyl, $C_{6-10}$ aryl, heteroaryl containing 3 to 9 ring carbon atoms and one or more ring heteroatoms independently selected from N, O, and S having 0 to 4 ring nitrogen atoms, 0 to 1 ring oxygen atoms, and 0 to 1 ring sulfur atoms, or $C_{3-6}$ cycloalkyl, wherein $R^1$ and $R^2$, together with the N atom to which they are attached, may form a heterocyclic ring system, wherein the heterocyclic ring system is a monocyclic ring having 2 to 6 ring carbon atoms, 1 to 2 ring nitrogen atoms, 0 to 1 ring oxygen atoms, and 0 to 1 ring sulfur atoms, or a bicyclic ring system that is a fused, spiro, or bridged ring system having 5 to 11 ring carbon atoms, 1 to 3 ring nitrogen atoms, 0 to 1 ring oxygen atoms, and 0 to 1 ring sulfur atoms, wherein the heterocyclic ring system is saturated or partially saturated; and when X is —$N(R^B)$—, $R^1$ and $R^B$ may be linked, and together with the N atom to which $R^1$ is attached and the carbonyl group to which X is attached, may form a monocyclic heterocyclic ring having 2 to 6 ring carbon atoms, 1 to 2 ring nitrogen atoms, 0 to 1 ring oxygen atoms, and 0 to 1 ring sulfur atoms, wherein the heterocyclic ring is saturated or partially saturated, and wherein $R^1$, $R^2$ and $R^B$ are independently optionally substituted and each substituent is independently F, Cl, Br, I, —$NR^A R^B$, $C_{1-6}$ hydrocarbyl, —OH, —CN, or —O—$C_{1-6}$ alkyl; and $R^5$ is an optionally substituted phenyl with 0, 1, 2, 3, 4, or 5 substituents and each substituent is independently F, Cl, Br, I, —$NR^A R^B$, $C_{1-6}$ hydrocarbyl, —OH, —CN, or —O—$C_{1-6}$ alkyl.

2. The compound of claim 1, represented by formula I or II:

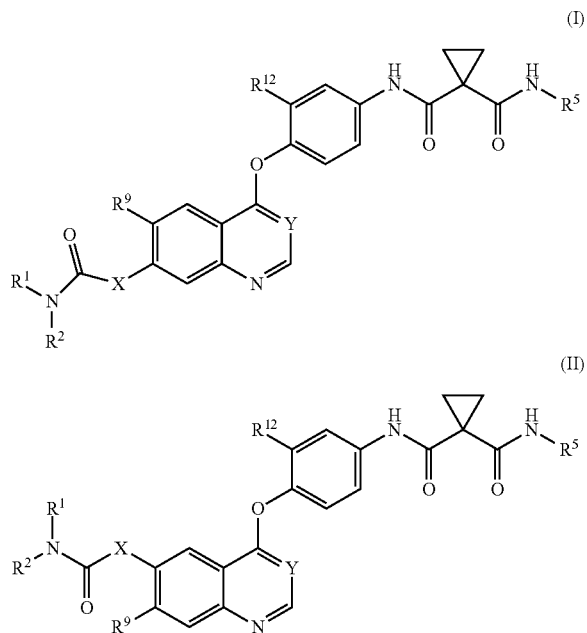

or a pharmaceutically acceptable salt thereof, wherein each structure is independently optionally substituted and each substituent is independently F, Cl, Br, I, —$NR^A R^B$, $C_{1-6}$ hydrocarbyl, —OH, —CN, or —O—$C_{1-6}$ alkyl;

$R^9$ is —O—$C_{1-6}$ alkyl; and each $R^{12}$ is H, F, Cl, $C_{1-3}$ hydrocarbyl.

3. The compound of claim 2, wherein $R^9$ is —O—$C_{1-3}$ alkyl.

4. The compound of claim 2, wherein $R^9$ is methoxy.

5. The compound of claim 2, wherein Y is CH.

6. The compound of claim 1, wherein Y is N.

7. The compound of claim 1, wherein Ring D is an unsubstituted cyclopropane-1,1-di-yl.

8. The compound of claim 2, wherein $R^{12}$ is F.

9. The compound of claim 2, wherein $R^{12}$ is H.

10. The compound of claim 1, wherein —$N(R^1)(R^2)$ is optionally substituted (R)-2,4-dimethylpiperazin-1-yl.

11. The compound of claim 1, wherein —$N(R^1)(R^2)$ is optionally substituted (S)-2,4-dimethylpiperazin-1-yl.

12. The compound of claim 1, wherein —$N(R^1)(R^2)$ is optionally substituted 4-methylpiperazin-1-yl.

13. The compound of claim 1, wherein —$N(R^1)(R^2)$ is optionally substituted (R)-2-methylpiperazin-1-yl.

14. The compound of claim 1, wherein —$N(R^1)(R^2)$ is optionally substituted 2-oxoimidazolidin-1-yl.

15. The compound of claim 1, wherein $R^5$ is unsubstituted phenyl.

16. The compound of claim 1, wherein $R^5$ is 4-fluorophenyl.

17. The compound of claim 1, or a pharmaceutically acceptable salt thereof, wherein the compound is:
   optionally substituted 4-(4-(1-(phenylcarbamoyl)cyclopropane-1-carboxamido)phenoxy)quinolin-7-yl piperazine-1-carboxylate,
   optionally substituted 4-(4-(1-(phenylcarbamoyl)cyclopropane-1-carboxamido)phenoxy)quinolin-7-yl piperidine-1-carboxylate,
   optionally substituted 4-(4-(1-(phenylcarbamoyl)cyclopropane-1-carboxamido)phenoxy)quinolin-7-yl pyrrolidine-1-carboxylate,
   optionally substituted 4-(4-(1-(phenylcarbamoyl)cyclopropane-1-carboxamido)phenoxy)quinolin-7-yl carbamate,
   optionally substituted 4-(4-(1-(phenylcarbamoyl)cyclopropane-1-carboxamido)phenoxy)quinolin-7-yl 2,6-dihydropyrrolo[3,4-c]pyrazole-5(4H)-carboxylate,
   optionally substituted 4-(4-(1-(phenylcarbamoyl)cyclopropane-1-carboxamido)phenoxy)quinolin-7-yl morpholine-4-carboxylate,
   optionally substituted 4-(4-(1-(phenylcarbamoyl)cyclopropane-1-carboxamido)phenoxy)quinolin-7-yl (1R, 4R)-2,5-diazabicyclo[2.2.1]heptane-2-carboxylate,
   optionally substituted 4-(4-(1-(phenylcarbamoyl)cyclopropane-1-carboxamido)phenoxy)quinolin-7-yl (1S, 4S)-2,5-diazabicyclo[2.2.1]heptane-2-carboxylate,
   optionally substituted N-(4-((7-(2-oxoimidazolidin-1-yl)quinolin-4-yl)oxy)phenyl)-N-phenylcyclopropane-1,1-dicarboxamide,
   optionally substituted 4-(4-(1-(phenylcarbamoyl)cyclopropane-1-carboxamido)phenoxy)quinolin-7-yl (1R, 5S)-3,8-diazabicyclo[3.2.1]octane-8-carboxylate,
   optionally substituted 4-(4-(1-(phenylcarbamoyl)cyclopropane-1-carboxamido)phenoxy)quinolin-6-yl piperazine-1-carboxylate,
   optionally substituted 4-(4-(1-(phenylcarbamoyl)cyclopropane-1-carboxamido)phenoxy)quinazolin-7-yl piperazine-1-carboxylate, or
   optionally substituted 4-(4-(1-(phenylcarbamoyl)cyclopropane-1-carboxamido)phenoxy)quinolin-7-yl (1R, 5S)-3,6-diazabicyclo[3.1.1]heptane-6-carboxylate.

18. The compound of claim 1, wherein the compound is deuterated.

19. The compound of claim 1, or a pharmaceutically acceptable salt thereof, wherein the compound is:

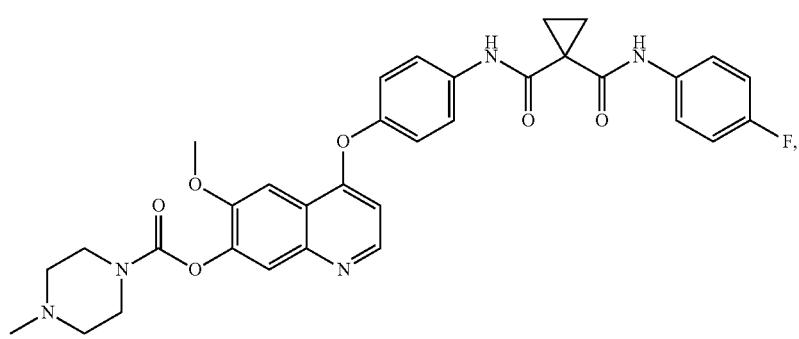

-continued
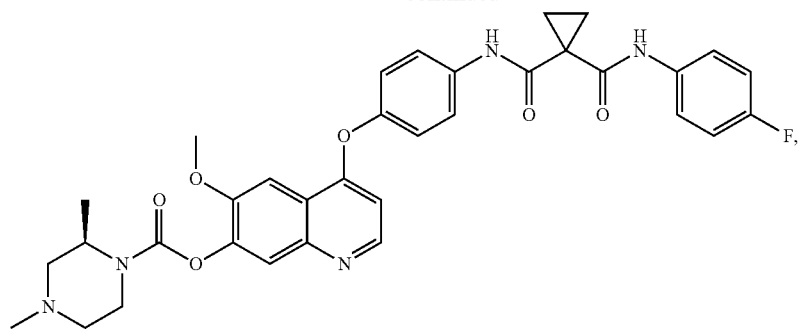
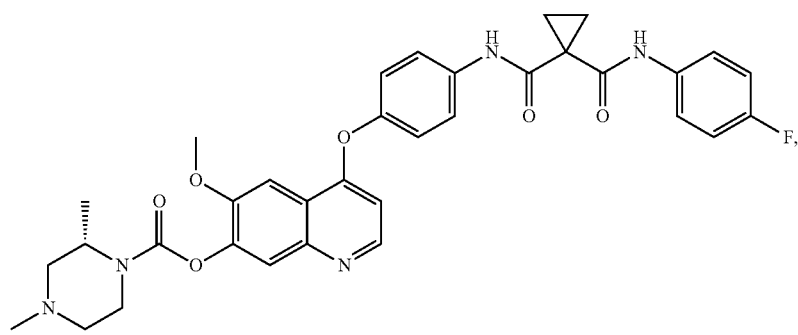
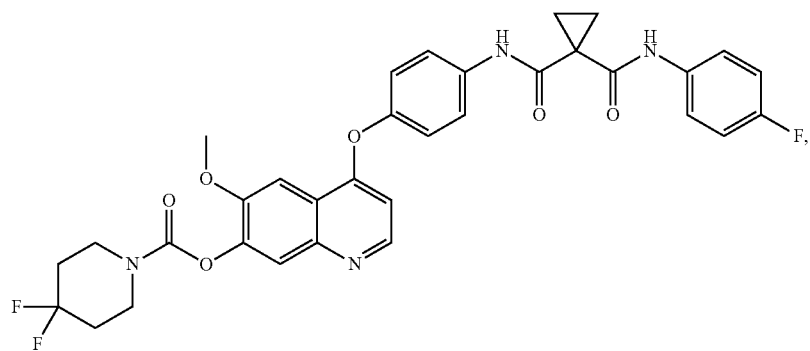
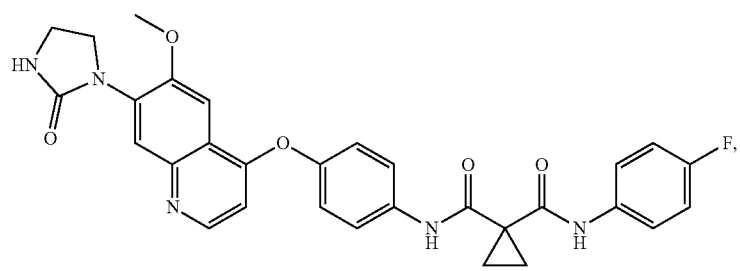
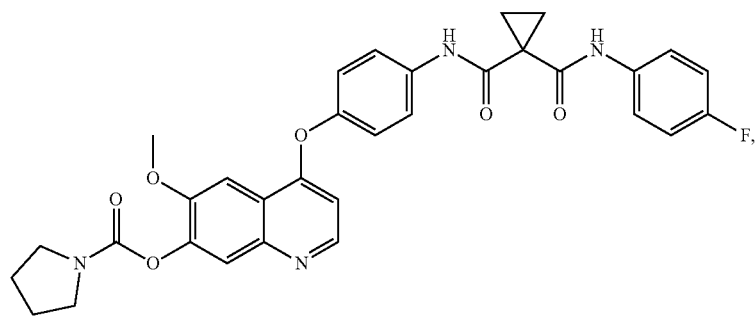

-continued
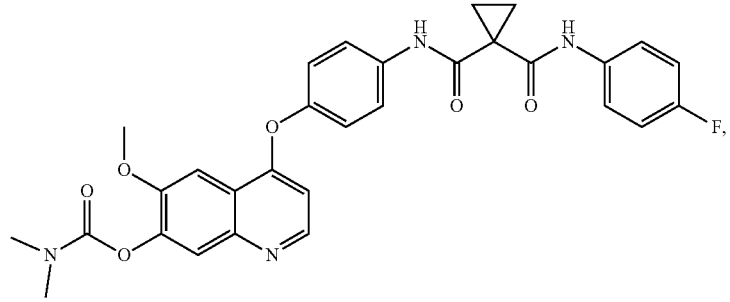
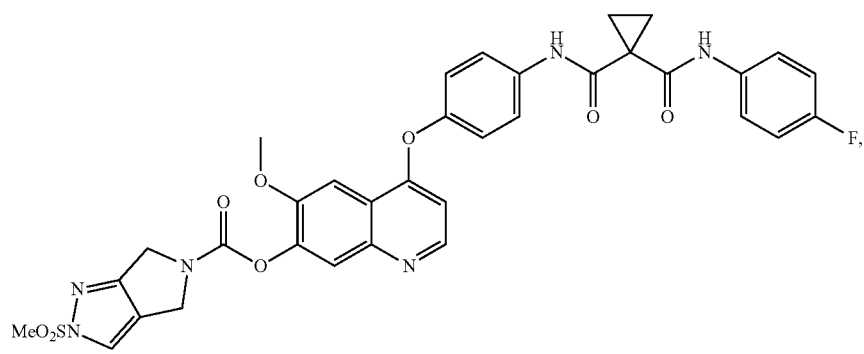
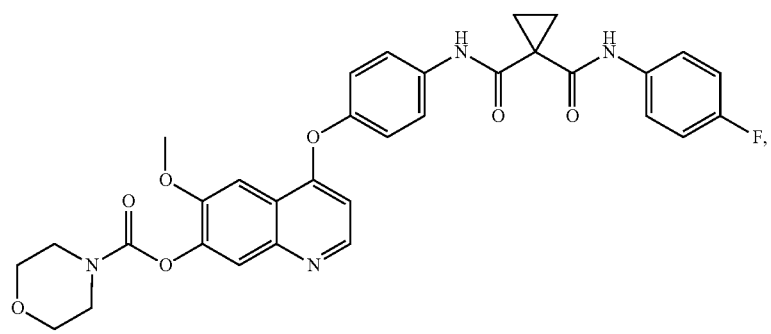
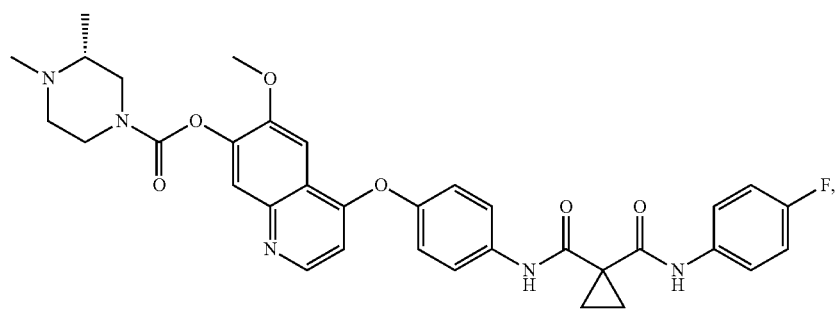
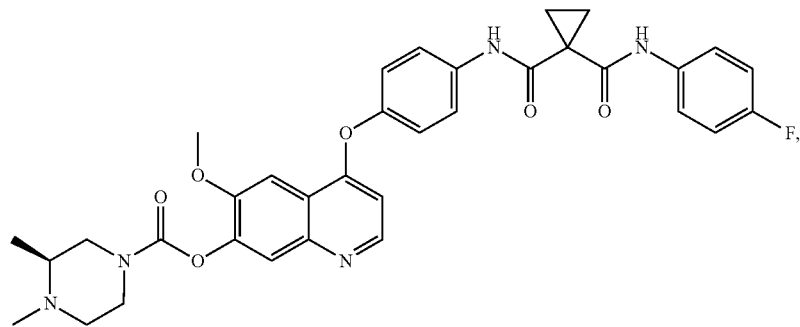

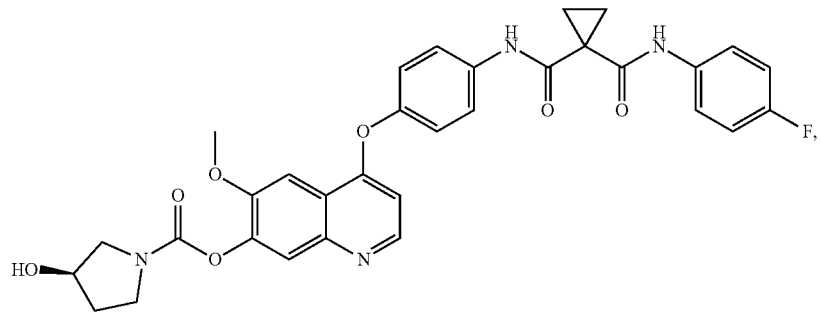
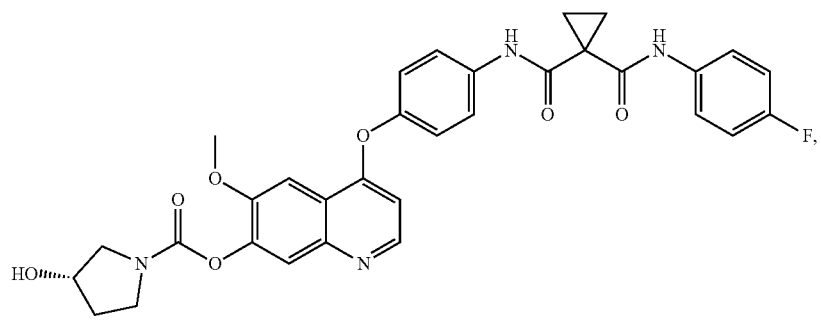
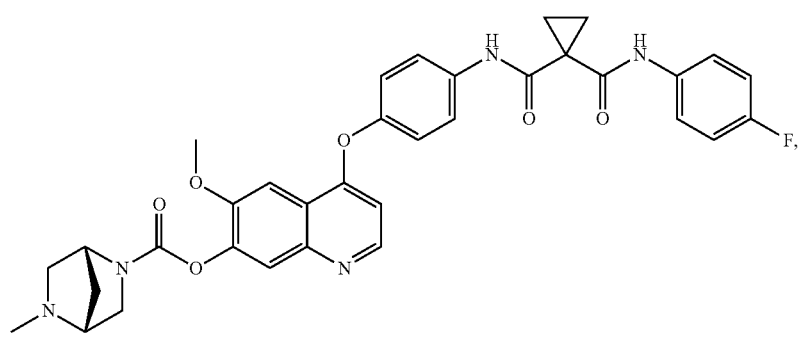
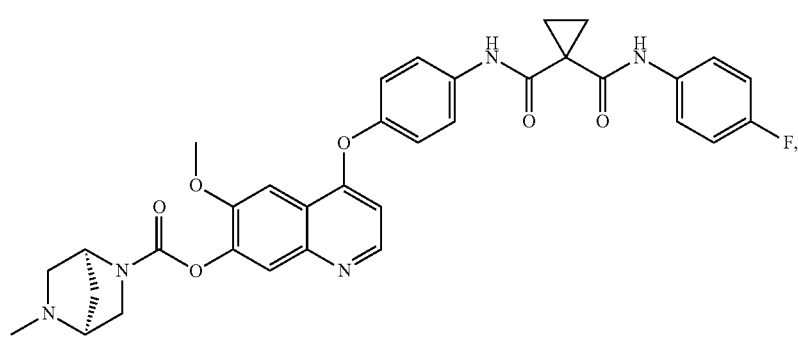
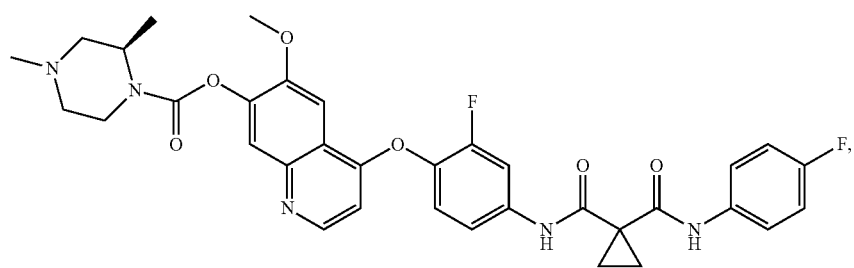

-continued
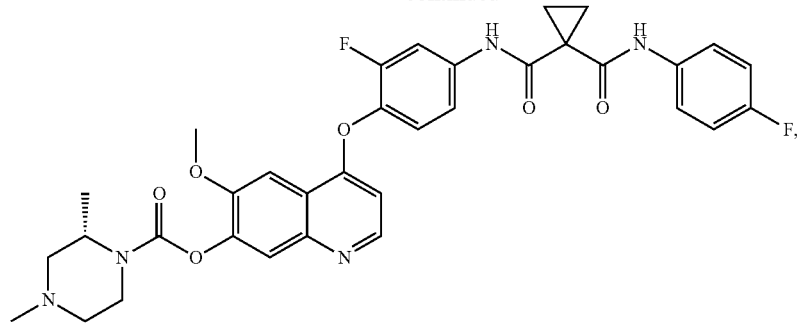
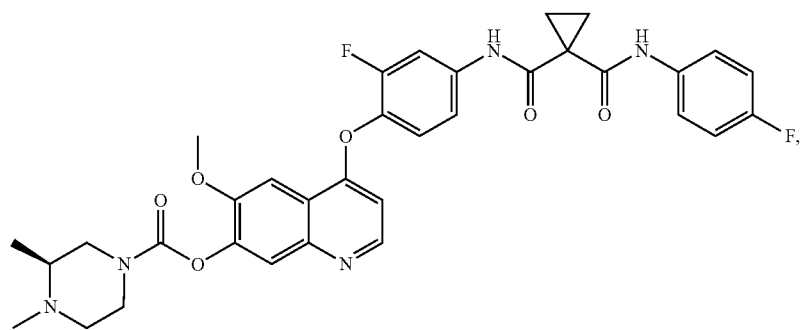
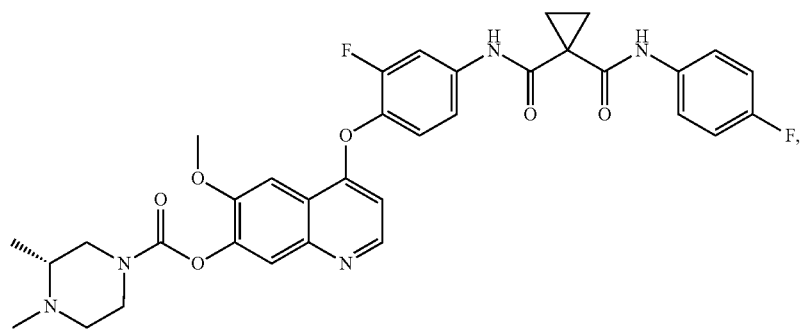
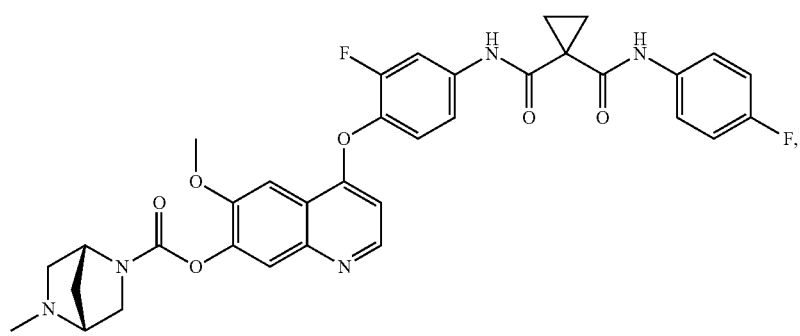
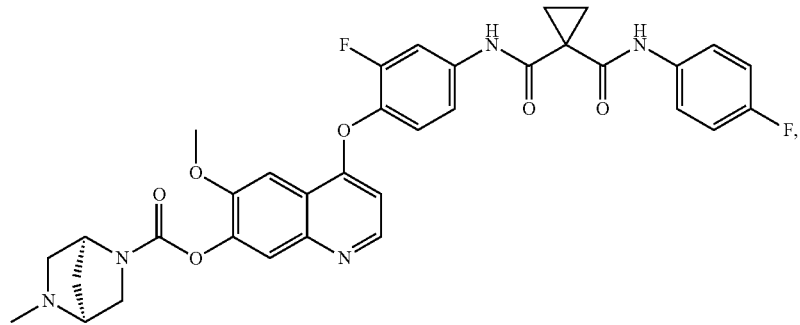

-continued
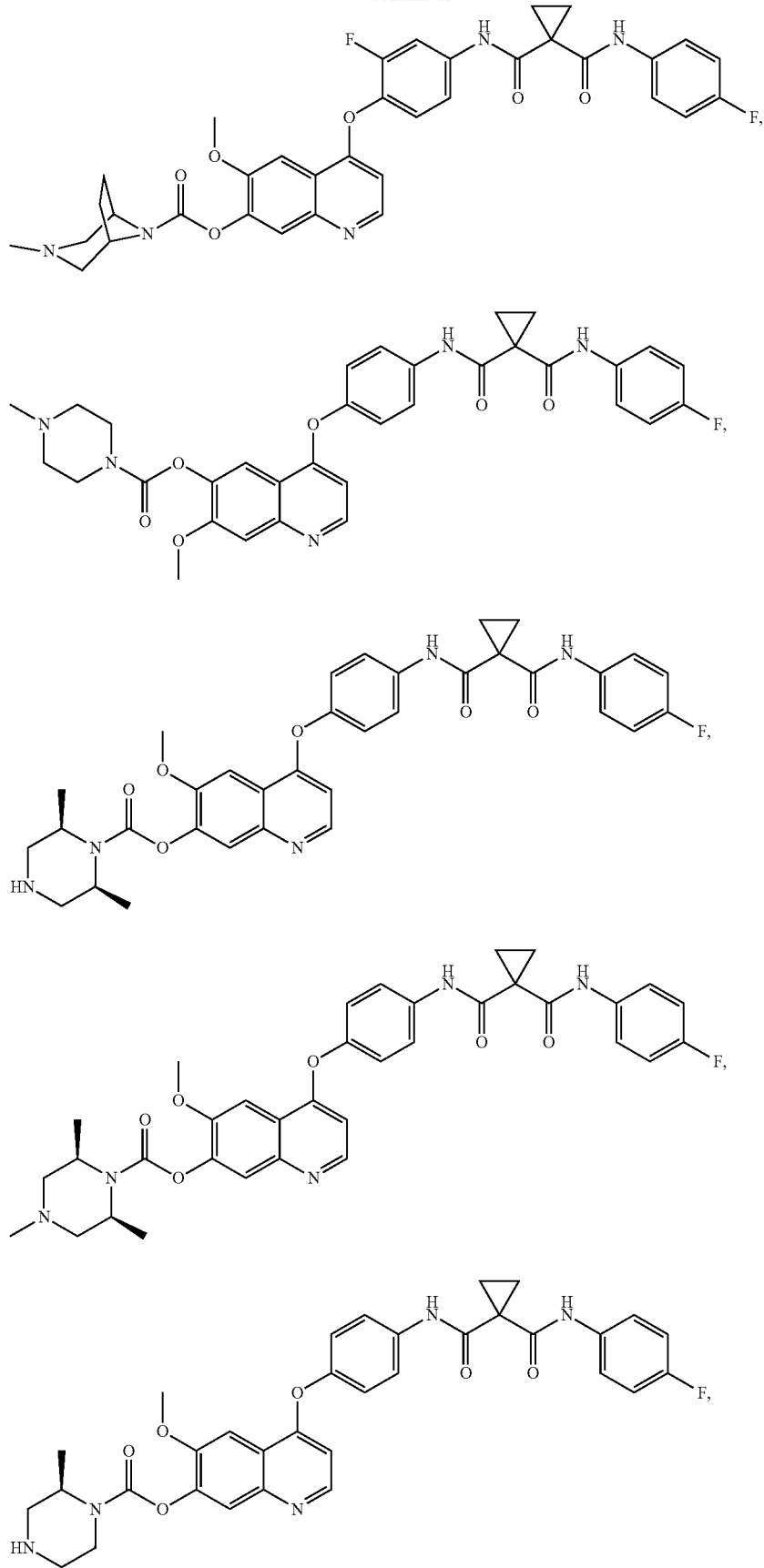

-continued
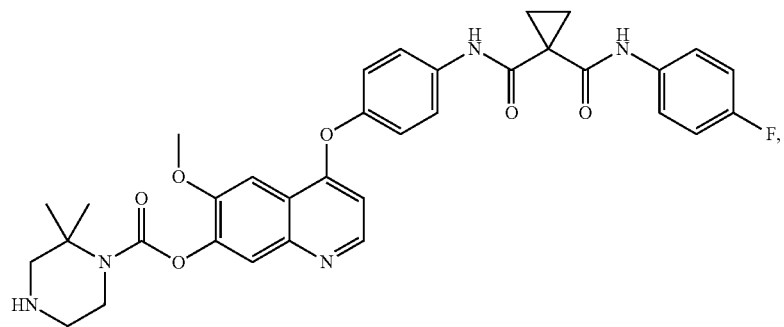
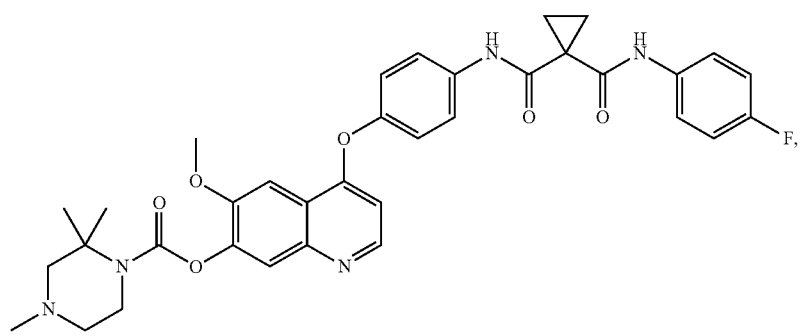
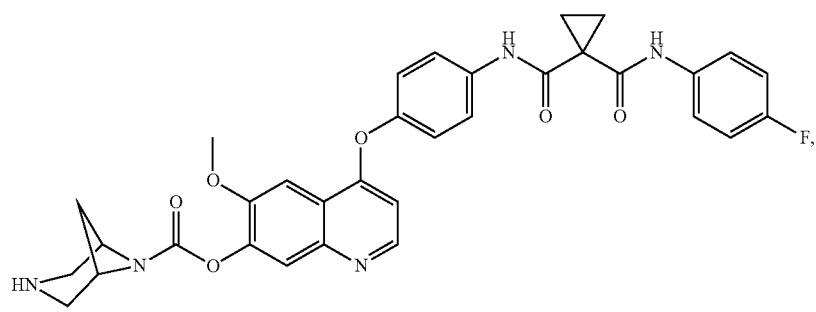
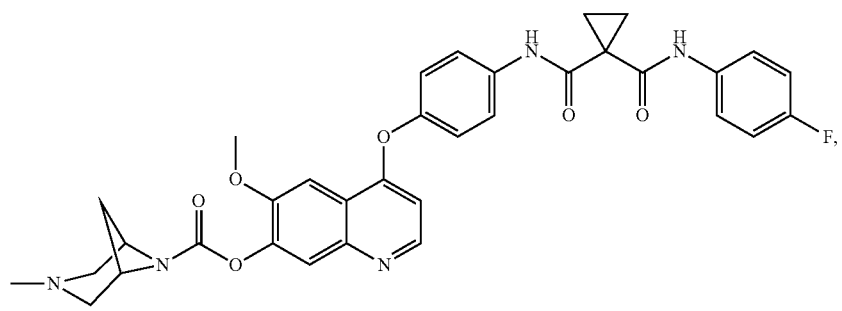
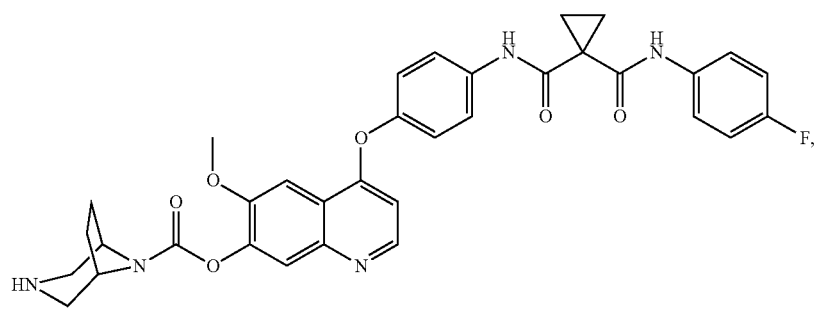

-continued
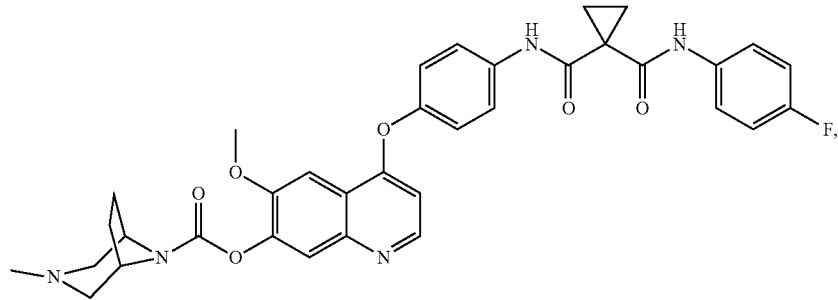
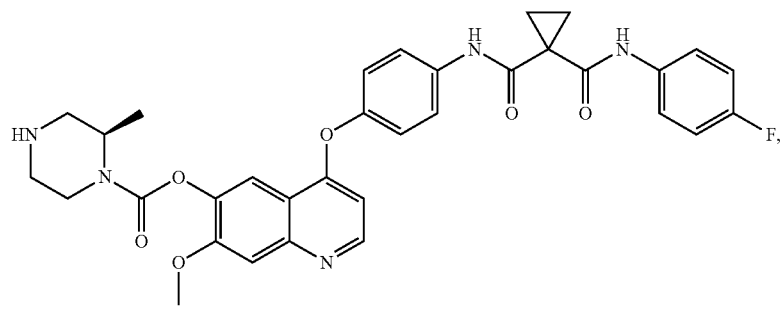
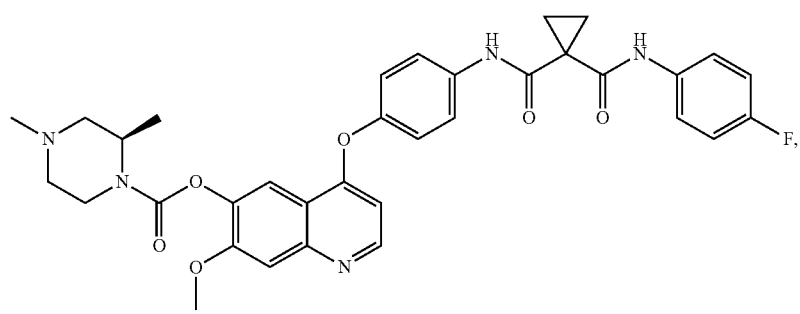
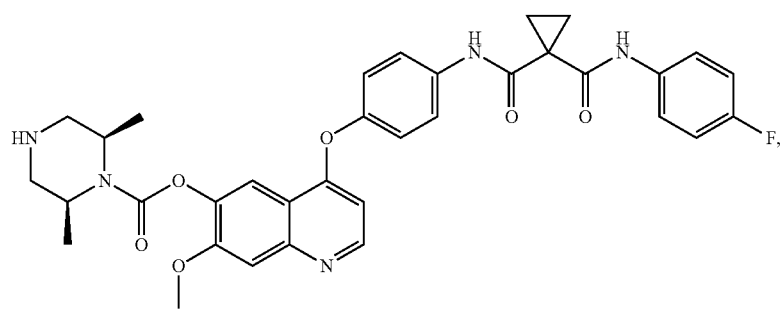
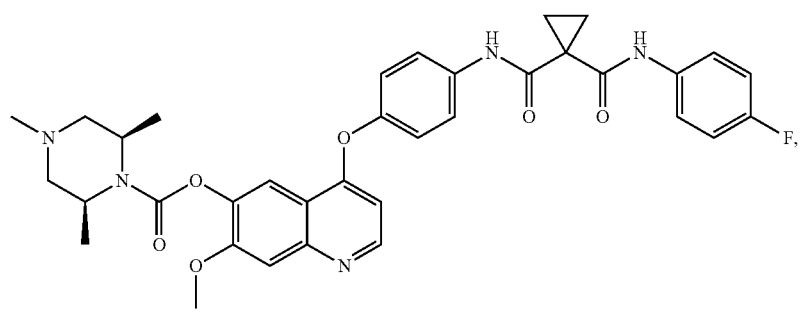

-continued
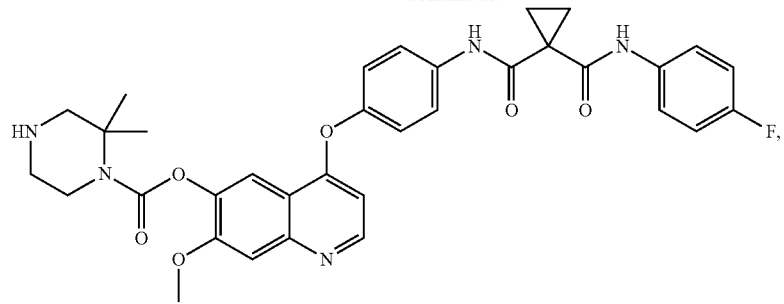
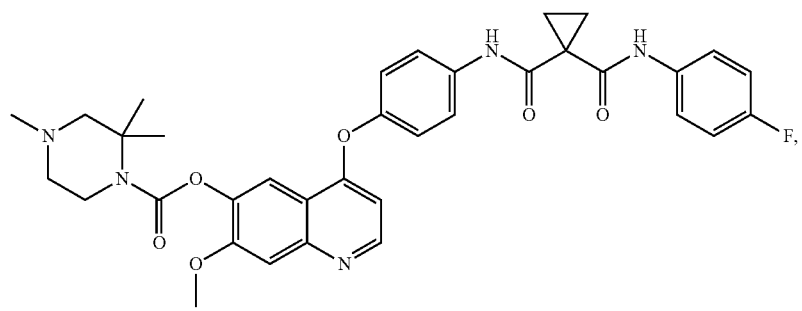
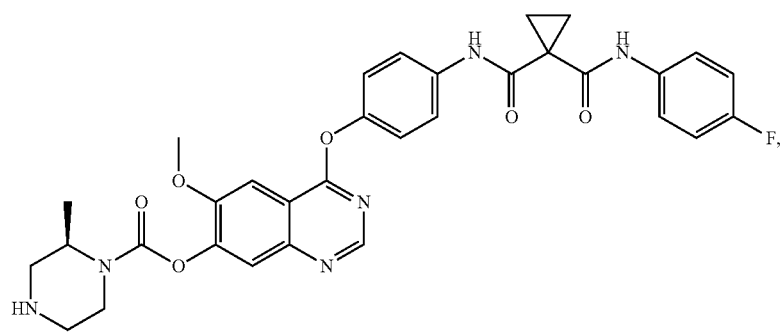
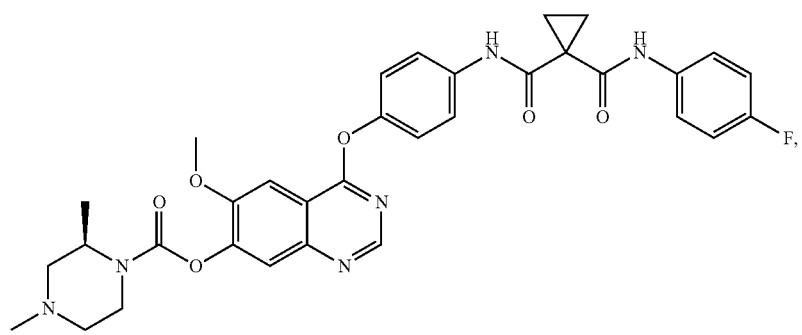
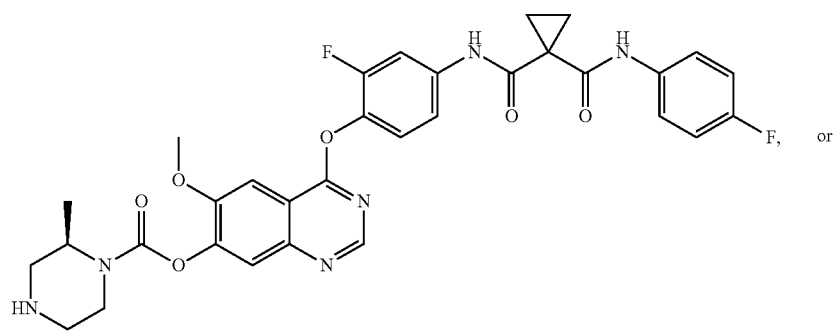
or

-continued
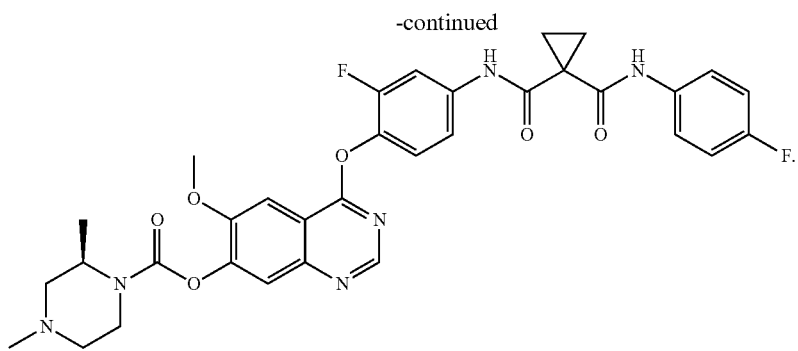
15
20. A pharmaceutical composition comprising a compound of claim 1 or a pharmaceutically acceptable salt thereof, and at least one pharmaceutically acceptable carrier.
* * * * *